(12) United States Patent
McDaniel

(10) Patent No.: US 8,651,111 B2
(45) Date of Patent: Feb. 18, 2014

(54) PHOTOMODULATION METHODS AND DEVICES FOR REGULATING CELL PROLIFERATION AND GENE EXPRESSION

(76) Inventor: David H. McDaniel, Virginia Beach, VA (US)

( * ) Notice: Subject to any disclaimer, the term of this patent is extended or adjusted under 35 U.S.C. 154(b) by 0 days.

(21) Appl. No.: 11/116,434

(22) Filed: Apr. 28, 2005

(65) Prior Publication Data

US 2005/0283211 A1  Dec. 22, 2005

Related U.S. Application Data

(63) Continuation of application No. 10/821,193, filed on Apr. 9, 2004, now abandoned.

(60) Provisional application No. 60/461,412, filed on Apr. 10, 2003.

(51) Int. Cl.
*A61B 19/00* (2006.01)

(52) U.S. Cl.
USPC ............................................. 128/898; 607/88

(58) Field of Classification Search
USPC .............................. 128/898; 606/9; 607/88–94
See application file for complete search history.

(56) References Cited

U.S. PATENT DOCUMENTS

| | | |
|---|---|---|
| 3,499,437 A | 3/1970 | Balamuth |
| 3,876,907 A | 4/1975 | Widmayer |
| 3,930,335 A | 1/1976 | Widmayer |
| 4,069,823 A | 1/1978 | Isakov et al. |
| 4,309,989 A | 1/1982 | Fahim |
| 4,458,678 A | 7/1984 | Yannas et al. |
| 4,558,700 A | 12/1985 | Mutshas |
| 4,603,496 A | 8/1986 | Latz et al. |

(Continued)

FOREIGN PATENT DOCUMENTS

| | | |
|---|---|---|
| EP | 0159446 | 10/1985 |
| EP | 0298661 | 1/1989 |

(Continued)

OTHER PUBLICATIONS

International Search Report mailed Apr. 12, 2005.

(Continued)

*Primary Examiner* — Ahmed Farah
(74) *Attorney, Agent, or Firm* — Nelson Mullins Riley & Scarborough LLP

(57) ABSTRACT

Human and mammalian skin undergoes a variety of changes associated with chronological aging. Various environmental factors, disease states and genetic disorders may accelerate both the appearance of aging skin and also the structural and functional changes associated with aging skin. Ultraviolet radiation from the sun is one of the classic known and well-defined means of accelerating or worsening the aging of the skin and this is frequently termed photoaging. Other environmental factors, such as oxidative stress, free radicals, environmental toxins such as ozone and cultural customs or habits such as tobacco smoking are other known probe accelerators in photo aging skin. A wide variety of other factors known and unknown contribute to accelerated or premature aging of the skin. This invention discusses methods where electromagnetic radiation, in particular, light, can be used to photobiomodulate the activity of living cells to delay, diminish, retard or even reverse the structural and functional effects of aging of the skin and other living cells and tissues. In particular methods described for improving the appearance, structure, function of aging skin, including up and down regulating the genotypic markers for the phenotype of aging skin.

7 Claims, 19 Drawing Sheets

(56) References Cited

U.S. PATENT DOCUMENTS

| | | | |
|---|---|---|---|
| 4,621,287 A | 11/1986 | Reitmeier et al. | |
| 4,628,442 A | 12/1986 | Edward | |
| 4,629,363 A | 12/1986 | Dearden et al. | |
| 4,646,743 A | 3/1987 | Parris | |
| 4,753,958 A | 6/1988 | Weinstein et al. | |
| 4,764,379 A | 8/1988 | Sanders et al. | |
| 4,767,402 A | 8/1988 | Kost et al. | |
| 4,781,924 A | 11/1988 | Lee et al. | |
| 4,822,335 A | 4/1989 | Kawai et al. | |
| 4,836,203 A | 6/1989 | Muller et al. | |
| 4,837,027 A | 6/1989 | Lee et al. | |
| 4,880,001 A | 11/1989 | Weinberg | |
| 4,888,354 A | 12/1989 | Chang et al. | |
| 4,907,132 A | 3/1990 | Parker | |
| 4,930,504 A | 6/1990 | Diamtopulos et al. | |
| 4,932,934 A | 6/1990 | Dougherty et al. | |
| 4,935,665 A | 6/1990 | Murata | |
| 4,969,912 A | 11/1990 | Kelman et al. | |
| 5,001,556 A | 3/1991 | Nakamura | |
| 5,012,609 A | 5/1991 | Ignatius et al. | |
| 5,016,615 A | 5/1991 | Driller et al. | |
| 5,021,452 A | 6/1991 | Labbe et al. | |
| 5,034,613 A | 7/1991 | Denk et al. | |
| 5,037,432 A | 8/1991 | Molinari | |
| 5,071,416 A | 12/1991 | Heller et al. | |
| 5,147,349 A | 9/1992 | Johnson | |
| 5,150,704 A | 9/1992 | Tatebayashi et al. | |
| 5,171,215 A | 12/1992 | Flanagan | |
| 5,198,645 A | 3/1993 | Dioguardi | |
| 5,226,907 A | 7/1993 | Tankovich | |
| 5,231,975 A | 8/1993 | Bommannan et al. | |
| 5,257,173 A | 10/1993 | Ohmamyuda et al. | |
| 5,259,380 A * | 11/1993 | Mendes et al. | 607/115 |
| 5,262,401 A | 11/1993 | Vogel et al. | |
| 5,266,480 A | 11/1993 | Naughton et al. | |
| 5,278,432 A | 1/1994 | Ignatius et al. | |
| 5,332,802 A | 7/1994 | Kelman et al. | |
| 5,344,434 A | 9/1994 | Talmore | |
| 5,358,503 A | 10/1994 | Bertwell et al. | |
| 5,360,824 A | 11/1994 | Barker | |
| 5,366,498 A | 11/1994 | Brannan et al. | |
| 5,397,352 A | 3/1995 | Burres | |
| 5,399,583 A | 3/1995 | Levy et al. | |
| 5,421,816 A | 6/1995 | Lipkovker | |
| 5,423,803 A | 6/1995 | Tankovich et al. | |
| 5,425,728 A | 6/1995 | Tankovich | |
| 5,445,143 A | 8/1995 | Bellenger | |
| 5,445,146 A | 8/1995 | Bellinger | |
| 5,445,608 A | 8/1995 | Chen et al. | |
| 5,445,611 A | 8/1995 | Eppstein et al. | |
| 5,445,634 A | 8/1995 | Keller | |
| 5,460,939 A | 10/1995 | Hansbrough et al. | |
| 5,474,528 A | 12/1995 | Meserol | |
| 5,492,135 A | 2/1996 | Devore | |
| 5,500,009 A | 3/1996 | Mendes et al. | |
| 5,549,660 A | 8/1996 | Mendes et al. | |
| 5,591,444 A | 1/1997 | Boss, Jr. | |
| 5,616,140 A * | 4/1997 | Prescott | 606/10 |
| 5,618,275 A | 4/1997 | Bock | |
| 5,620,478 A | 4/1997 | Eckhouse | |
| 5,634,711 A | 6/1997 | Kennedy et al. | |
| 5,636,632 A | 6/1997 | Bommannan et al. | |
| 5,643,334 A | 7/1997 | Eckhouse et al. | |
| 5,647,866 A | 7/1997 | Zaias et al. | |
| 5,658,323 A | 8/1997 | Miller | |
| 5,660,461 A | 8/1997 | Ignatius et al. | |
| 5,660,836 A | 8/1997 | Knowlton | |
| 5,660,850 A | 8/1997 | Boss, Jr. | |
| 5,662,644 A | 9/1997 | Swor | |
| 5,665,053 A | 9/1997 | Jacobs | |
| 5,665,372 A | 9/1997 | Boss, Jr. | |
| 5,669,916 A | 9/1997 | Anderson | |
| 5,683,380 A | 11/1997 | Eckhouse et al. | |
| 5,686,112 A | 11/1997 | Liedtke | |
| 5,698,866 A | 12/1997 | Doiron et al. | |
| 5,707,401 A | 1/1998 | Talmore | |
| 5,728,090 A | 3/1998 | Martin et al. | |
| 5,752,948 A | 5/1998 | Tankovich et al. | |
| 5,752,949 A | 5/1998 | Tankovich et al. | |
| 5,755,752 A | 5/1998 | Segal | |
| 5,766,214 A | 6/1998 | Mehl, Sr. et al. | |
| 5,766,233 A | 6/1998 | Thiberg | |
| 5,766,234 A | 6/1998 | Chen et al. | |
| 5,773,609 A | 6/1998 | Robinson et al. | |
| 5,800,478 A | 9/1998 | Chen et al. | |
| 5,800,479 A | 9/1998 | Thiberg | |
| 5,810,801 A | 9/1998 | Anderson et al. | |
| 5,814,599 A | 9/1998 | Mitragotri et al. | |
| 5,817,089 A | 10/1998 | Tankovich et al. | |
| 5,829,448 A | 11/1998 | Fisher et al. | |
| 5,836,999 A | 11/1998 | Eckhouse et al. | |
| 5,837,224 A | 11/1998 | Voorhees et al. | |
| 5,843,072 A | 12/1998 | Furmoto et al. | |
| 5,849,029 A | 12/1998 | Eckhouse et al. | |
| 5,871,480 A | 2/1999 | Tankovich | |
| 5,904,659 A | 5/1999 | Duarte et al. | |
| 5,913,883 A * | 6/1999 | Alexander et al. | 607/88 |
| 5,932,240 A | 8/1999 | D'Angelo et al. | |
| 5,947,921 A | 9/1999 | Johnson et al. | |
| 5,951,596 A | 9/1999 | Bellinger | |
| 5,954,675 A | 9/1999 | Dellagatta | |
| 5,968,034 A | 10/1999 | Fulmer et al. | |
| 5,997,569 A | 12/1999 | Chen et al. | |
| 6,024,717 A | 2/2000 | Ball et al. | |
| 6,030,374 A | 2/2000 | McDaniel | |
| 6,048,301 A | 4/2000 | Sabuda | |
| 6,050,990 A | 4/2000 | Tankovich et al. | |
| 6,063,108 A * | 5/2000 | Salansky et al. | 607/89 |
| 6,074,382 A | 6/2000 | Asah et al. | |
| 6,096,066 A | 8/2000 | Chen | |
| 6,099,522 A | 8/2000 | Knopp | |
| 6,110,106 A | 8/2000 | MacKinnon et al. | |
| 6,113,559 A | 9/2000 | Klopotek | |
| 6,120,497 A | 9/2000 | Anderson et al. | |
| 6,130,254 A | 10/2000 | Fisher et al. | |
| 6,143,287 A | 11/2000 | Ben-Hur et al. | |
| 6,162,211 A | 12/2000 | Tankovich et al. | |
| 6,171,331 B1 * | 1/2001 | Bagraev et al. | 607/88 |
| 6,171,332 B1 | 1/2001 | Whitehurst | |
| 6,174,325 B1 | 1/2001 | Eckhouse | |
| 6,183,773 B1 | 2/2001 | Anderson | |
| 6,187,029 B1 | 2/2001 | Shapiro et al. | |
| 6,190,315 B1 | 2/2001 | Kost et al. | |
| 6,190,376 B1 | 2/2001 | Asah | |
| 6,214,034 B1 * | 4/2001 | Azar | 607/89 |
| 6,221,095 B1 | 4/2001 | Van Zuylen et al. | |
| 6,223,071 B1 | 4/2001 | Lundahl et al. | |
| 6,231,528 B1 | 5/2001 | Kaufman et al. | |
| 6,238,424 B1 | 5/2001 | Thiberg | |
| 6,251,127 B1 | 6/2001 | Biel | |
| 6,267,779 B1 | 7/2001 | Gerdes | |
| 6,273,884 B1 * | 8/2001 | Altshuler et al. | 606/9 |
| 6,283,956 B1 | 9/2001 | McDaniel | |
| 6,290,713 B1 * | 9/2001 | Russell | 607/88 |
| 6,302,874 B1 | 10/2001 | Zhang et al. | |
| 6,312,450 B1 * | 11/2001 | Yavitz et al. | 607/88 |
| 6,387,089 B1 * | 5/2002 | Kreindel et al. | 606/9 |
| 6,398,753 B2 | 6/2002 | McDaniel | |
| 6,413,268 B1 | 7/2002 | Hartman | |
| 6,436,127 B1 | 8/2002 | Anderson et al. | |
| 6,443,946 B2 | 9/2002 | Clement et al. | |
| 6,443,978 B1 * | 9/2002 | Zharov | 607/91 |
| 6,459,087 B1 | 10/2002 | Kaas | |
| 6,461,866 B1 * | 10/2002 | Whitehurst | 435/325 |
| 6,471,716 B1 * | 10/2002 | Pecukonis | 607/89 |
| 6,497,719 B2 | 12/2002 | Pearl et al. | |
| 6,524,330 B1 | 2/2003 | Khoobehi et al. | |
| 6,602,275 B1 * | 8/2003 | Sullivan | 607/88 |
| 6,629,971 B2 | 10/2003 | McDaniel | |
| 6,630,516 B2 | 10/2003 | Varani et al. | |
| 6,645,230 B2 | 11/2003 | Whitehurst | |
| 6,663,659 B2 | 12/2003 | McDaniel | |
| 6,664,217 B1 | 12/2003 | Puvvada et al. | |
| 6,676,655 B2 | 1/2004 | McDaniel | |

(56) References Cited

U.S. PATENT DOCUMENTS

| | | | |
|---|---|---|---|
| 6,709,866 B2 | 3/2004 | Robertson et al. | |
| 6,723,698 B2 | 4/2004 | Rueger et al. | |
| 6,723,798 B1 | 4/2004 | Yoo et al. | |
| 6,746,444 B2 | 6/2004 | Key | |
| 6,835,306 B2 | 12/2004 | Caldwell | |
| 6,866,678 B2 * | 3/2005 | Shenderova et al. | 607/88 |
| 6,881,212 B1 * | 4/2005 | Clement et al. | 606/9 |
| 6,887,260 B1 | 5/2005 | McDaniel | |
| 6,936,044 B2 | 8/2005 | McDaniel | |
| 7,004,933 B2 | 2/2006 | McDaniel | |
| 7,033,381 B1 | 4/2006 | Larsen | |
| 7,081,128 B2 * | 7/2006 | Hart et al. | 607/89 |
| 7,115,120 B2 | 10/2006 | Lin | |
| 7,147,863 B2 | 12/2006 | Fisher | |
| 7,195,755 B2 | 3/2007 | Nguyen et al. | |
| 7,201,765 B2 | 4/2007 | McDaniel | |
| 7,204,832 B2 | 4/2007 | Altshuler et al. | |
| 7,258,695 B2 | 8/2007 | Carullo, Jr. et al. | |
| 7,264,629 B2 | 9/2007 | Simkin et al. | |
| 7,267,673 B2 | 9/2007 | Pilcher et al. | |
| 7,309,335 B2 | 12/2007 | Altshuler et al. | |
| 7,331,952 B2 | 2/2008 | Walneck et al. | |
| 7,354,432 B2 | 4/2008 | Eells et al. | |
| 7,438,719 B2 | 10/2008 | Chung et al. | |
| 7,470,270 B2 | 12/2008 | Azar et al. | |
| 7,494,503 B2 | 2/2009 | McDaniel | |
| 7,511,031 B2 | 3/2009 | Chen | |
| 7,559,944 B2 | 7/2009 | Whang | |
| 7,597,708 B2 | 10/2009 | Carullo, Jr. et al. | |
| 7,618,414 B2 | 11/2009 | Connors et al. | |
| 8,188,074 B2 | 5/2012 | Brown et al. | |
| 8,372,433 B2 | 2/2013 | Shinoka et al. | |
| 2001/0013349 A1 * | 8/2001 | Clement et al. | 128/898 |
| 2001/0023363 A1 * | 9/2001 | Harth et al. | 607/90 |
| 2001/0053347 A1 | 12/2001 | Varani et al. | |
| 2002/0028185 A1 | 3/2002 | Fisher et al. | |
| 2002/0029071 A1 * | 3/2002 | Whitehurst | 607/88 |
| 2002/0123746 A1 | 9/2002 | McDaniel | |
| 2002/0161357 A1 | 10/2002 | Anderson et al. | |
| 2002/0173833 A1 | 11/2002 | Korman et al. | |
| 2002/0183724 A1 | 12/2002 | Neev | |
| 2002/0198575 A1 | 12/2002 | Sullivan | |
| 2003/0004499 A1 | 1/2003 | McDaniel | |
| 2003/0004556 A1 | 1/2003 | McDaniel | |
| 2003/0060811 A1 | 3/2003 | McDaniel | |
| 2003/0129154 A1 | 7/2003 | McDaniel | |
| 2004/0039378 A1 | 2/2004 | Lin | |
| 2004/0215293 A1 | 10/2004 | Eells et al. | |
| 2005/0090877 A1 | 4/2005 | Harth et al. | |
| 2006/0129209 A1 | 6/2006 | McDaniel | |
| 2006/0184214 A1 | 8/2006 | McDaniel | |
| 2006/0200213 A1 | 9/2006 | McDaniel | |
| 2006/0212025 A1 | 9/2006 | McDaniel | |
| 2006/0265030 A1 | 11/2006 | McDaniel | |
| 2007/0073276 A1 | 3/2007 | Wilkens et al. | |
| 2007/0128576 A1 | 6/2007 | Boutoussov | |
| 2007/0129613 A1 | 6/2007 | Rochester et al. | |
| 2007/0129711 A1 | 6/2007 | Altshuler | |
| 2007/0129776 A1 | 6/2007 | Robins et al. | |
| 2007/0129778 A1 | 6/2007 | Dougal | |
| 2007/0149900 A1 | 6/2007 | Lin | |
| 2007/0149901 A1 | 6/2007 | Gordon et al. | |
| 2007/0150030 A1 | 6/2007 | Pearl | |
| 2007/0156208 A1 | 7/2007 | Havell | |
| 2007/0167999 A1 | 7/2007 | Breden et al. | |
| 2007/0168000 A1 | 7/2007 | Happawana | |
| 2007/0173912 A1 | 7/2007 | Amornsiripanitch | |
| 2007/0173913 A1 | 7/2007 | Anderson et al. | |
| 2007/0179482 A1 | 8/2007 | Anderson | |
| 2007/0179574 A1 | 8/2007 | Elliott | |
| 2007/0198004 A1 | 8/2007 | Altshuler et al. | |
| 2007/0208326 A1 | 9/2007 | Connors | |
| 2007/0208328 A1 | 9/2007 | Boutoussov | |
| 2007/0208395 A1 | 9/2007 | Leclerc | |
| 2007/0208396 A1 | 9/2007 | Whatcott | |
| 2007/0208400 A1 | 9/2007 | Nadkarni | |
| 2007/0213696 A1 | 9/2007 | Altshuler et al. | |
| 2007/0219604 A1 | 9/2007 | Yaroslavsky et al. | |
| 2007/0219605 A1 | 9/2007 | Yaroslavsky et al. | |
| 2007/0231255 A1 | 10/2007 | Barolet et al. | |
| 2007/0239142 A1 | 10/2007 | Altshuler et al. | |
| 2007/0239147 A1 | 10/2007 | Manstein et al. | |
| 2007/0299486 A1 | 12/2007 | Hoenig et al. | |
| 2008/0009923 A1 | 1/2008 | Paithankar | |
| 2008/0015555 A1 | 1/2008 | Manstein et al. | |
| 2008/0021528 A1 | 1/2008 | Carullo | |
| 2008/0031833 A1 | 2/2008 | Oblong | |
| 2008/0031924 A1 | 2/2008 | Gilson | |
| 2008/0033516 A1 | 2/2008 | Altshuler et al. | |
| 2008/0035864 A1 | 2/2008 | Fiset | |
| 2008/0039906 A1 | 2/2008 | Huang et al. | |
| 2008/0045933 A1 | 2/2008 | Perl | |
| 2008/0051856 A1 | 2/2008 | Vizethum | |
| 2008/0058783 A1 | 3/2008 | Altshuler et al. | |
| 2008/0058784 A1 | 3/2008 | Manstein et al. | |
| 2008/0058905 A1 | 3/2008 | Wagner | |
| 2008/0065056 A1 | 3/2008 | Powell et al. | |
| 2008/0065175 A1 | 3/2008 | Redmond | |
| 2008/0077199 A1 | 3/2008 | Shefi | |
| 2008/0082148 A1 | 4/2008 | Bernstein | |
| 2008/0082149 A1 | 4/2008 | Bernstein | |
| 2008/0091179 A1 | 4/2008 | Durkin et al. | |
| 2008/0097278 A1 | 4/2008 | Cole | |
| 2008/0097419 A1 | 4/2008 | MacFarland | |
| 2008/0103560 A1 | 5/2008 | Powell et al. | |
| 2008/0106896 A1 | 5/2008 | Liu et al. | |
| 2008/0139901 A1 | 6/2008 | Altshuler et al. | |
| 2008/0147054 A1 | 6/2008 | Altshuler et al. | |
| 2008/0147148 A1 | 6/2008 | Baldacchini | |
| 2008/0172112 A1 | 7/2008 | Gourgouliatos et al. | |
| 2008/0172114 A1 | 7/2008 | Gourgouliatos et al. | |
| 2008/0177255 A1 | 7/2008 | Bernardini | |
| 2008/0183161 A1 | 7/2008 | Walneck et al. | |
| 2008/0200908 A1 | 8/2008 | Domankevitz | |
| 2008/0203280 A1 | 8/2008 | Rizoiu | |
| 2008/0208294 A1 | 8/2008 | Pierce | |
| 2008/0208295 A1 | 8/2008 | Cumbie | |
| 2008/0234669 A1 | 9/2008 | Kauvar | |
| 2008/0234786 A1 | 9/2008 | Cumbie | |
| 2008/0255640 A1 | 10/2008 | Kipp | |
| 2008/0262394 A1 | 10/2008 | Pryor | |
| 2008/0262482 A1 | 10/2008 | Hantash et al. | |
| 2008/0262576 A1 | 10/2008 | Creamer | |
| 2008/0267814 A1 | 10/2008 | Bornstein | |
| 2008/0269732 A1 | 10/2008 | Pyun | |
| 2008/0269733 A1 | 10/2008 | Anderson | |
| 2008/0269844 A1 | 10/2008 | Logslett | |
| 2008/0269848 A1 | 10/2008 | Birmingham et al. | |
| 2008/0269849 A1 | 10/2008 | Lewis | |
| 2008/0275532 A1 | 11/2008 | Yamazaki | |
| 2008/0281307 A1 | 11/2008 | Donahue | |
| 2008/0294151 A1 | 11/2008 | Whitaker et al. | |
| 2008/0294152 A1 | 11/2008 | Altshuler et al. | |
| 2009/0012508 A1 | 1/2009 | Dougal | |
| 2009/0018621 A1 | 1/2009 | Vogler et al. | |
| 2009/0018622 A1 | 1/2009 | Asvadi et al. | |
| 2009/0024116 A1 | 1/2009 | Mulhauser et al. | |
| 2009/0043293 A1 | 2/2009 | Pankratov et al. | |
| 2009/0062889 A1 | 3/2009 | Kiessl | |
| 2009/0082836 A1 | 3/2009 | Schell | |
| 2009/0088824 A1 | 4/2009 | Marchese | |
| 2009/0105791 A1 | 4/2009 | McGinnis | |
| 2009/0112192 A1 | 4/2009 | Barolet | |
| 2009/0112294 A1 | 4/2009 | Huang | |
| 2009/0149843 A1 | 6/2009 | Smits et al. | |
| 2009/0177190 A1 | 7/2009 | Lee | |
| 2009/0177253 A1 | 7/2009 | Darm et al. | |
| 2009/0177256 A1 | 7/2009 | Ripper et al. | |
| 2009/0187169 A1 | 7/2009 | Durkin et al. | |
| 2009/0198173 A1 | 8/2009 | Samuel et al. | |
| 2009/0227996 A1 | 9/2009 | Powell et al. | |
| 2009/0234253 A1 | 9/2009 | Vandenbelt | |
| 2009/0234337 A1 | 9/2009 | Ely et al. | |
| 2009/0234341 A1 | 9/2009 | Roth et al. | |

(56) References Cited

U.S. PATENT DOCUMENTS

| | | |
|---|---|---|
| 2009/0234342 A1 | 9/2009 | Ely et al. |
| 2009/0247932 A1 | 10/2009 | Barolet |
| 2009/0251057 A1 | 10/2009 | Son et al. |
| 2009/0254154 A1 | 10/2009 | De Taboada |
| 2009/0254156 A1 | 10/2009 | Powell et al. |
| 2009/0270845 A1 | 10/2009 | Birmingham et al. |
| 2009/0270946 A1 | 10/2009 | Spivak |
| 2009/0270953 A1 | 10/2009 | Ecker |
| 2010/0121254 A1 | 5/2010 | McDaniel |
| 2010/0256550 A1 | 10/2010 | McDaniel |

FOREIGN PATENT DOCUMENTS

| | | |
|---|---|---|
| EP | 0320080 | 6/1989 |
| EP | 1839705 A1 | 3/2007 |
| EP | 1818077 A1 | 8/2007 |
| EP | 1837050 A1 | 9/2007 |
| EP | 1839704 A1 | 10/2007 |
| EP | 1842571 A2 | 10/2007 |
| EP | 1857145 A1 | 11/2007 |
| EP | 1878466 A1 | 1/2008 |
| EP | 1916016 A1 | 4/2008 |
| EP | 1920798 A1 | 5/2008 |
| EP | 1935452 A1 | 6/2008 |
| EP | 1958662 A1 | 8/2008 |
| EP | 1964590 A1 | 9/2008 |
| EP | 2044901 | 4/2009 |
| EP | 2044973 | 4/2009 |
| EP | 2044974 | 4/2009 |
| EP | 2055349 | 5/2009 |
| EP | 2106198 | 9/2009 |
| EP | 2106780 | 10/2009 |
| EP | 2106824 | 10/2009 |
| EP | 2110159 | 10/2009 |
| GB | 2262043 | 6/1993 |
| GB | 2360461 | 9/2001 |
| GB | 2360641 | 9/2001 |
| JP | H01-136668 | 5/1989 |
| JP | 07-016304 | 1/1995 |
| JP | H07-100219 | 4/1995 |
| JP | H07505614 | 6/1995 |
| JP | H08308943 | 11/1996 |
| JP | H09-508031 | 8/1997 |
| JP | H10-503109 | 3/1998 |
| JP | 2000-202044 | 7/2000 |
| JP | 2002522110 | 7/2002 |
| JP | 2002535101 | 10/2002 |
| JP | 2005503388 | 2/2005 |
| JP | 2010047590 | 3/2010 |
| RU | SU1724269 | 4/1992 |
| WO | 93/09847 | 5/1993 |
| WO | 93/09874 | 5/1993 |
| WO | 93/21842 | 11/1993 |
| WO | 95/19809 | 7/1995 |
| WO | 96/11723 | 4/1996 |
| WO | 96/24406 | 8/1996 |
| WO | 97/46279 | 12/1997 |
| WO | 98/11723 | 3/1998 |
| WO | 98/14453 | 4/1998 |
| WO | 98/50034 | 11/1998 |
| WO | 99/04628 | 2/1999 |
| WO | 99/19024 | 4/1999 |
| WO | 99/20336 | 4/1999 |
| WO | 99/39763 | 8/1999 |
| WO | 00/02491 | 1/2000 |
| WO | 00/02497 | 1/2000 |
| WO | 00/07514 | 2/2000 |
| WO | 00/32121 | 6/2000 |
| WO | 00/40266 | 7/2000 |
| WO | 00/44441 | 8/2000 |
| WO | 00/57804 | 10/2000 |
| WO | 00/74782 | 12/2000 |
| WO | WO0074782 A1 | 12/2000 |
| WO | 01/14012 | 3/2001 |
| WO | 01/40232 | 6/2001 |
| WO | 02/057811 | 7/2002 |
| WO | 03/001984 | 1/2003 |
| WO | 03/002187 | 1/2003 |
| WO | WO03005883 A2 | 1/2003 |
| WO | 03/017824 | 3/2003 |
| WO | 03/086215 | 10/2003 |
| WO | 2004/075985 | 9/2004 |
| WO | WO2004092335 A2 | 10/2004 |
| WO | 2005/011606 | 2/2005 |
| WO | 2005/077452 | 8/2005 |
| WO | 2005/089039 | 9/2005 |
| WO | 2005/096766 | 10/2005 |
| WO | 2005/115263 A1 | 12/2005 |
| WO | 2006/013390 | 2/2006 |
| WO | 2006/013390 A1 | 2/2006 |
| WO | 2006/099413 A2 | 9/2006 |
| WO | 2006/107387 A2 | 10/2006 |
| WO | 2006/116141 A1 | 11/2006 |
| WO | 2006/125231 A2 | 11/2006 |
| WO | 2007/013110 A1 | 2/2007 |
| WO | 2007/036002 A1 | 4/2007 |
| WO | 2007/044840 A2 | 4/2007 |
| WO | 2007/066657 A1 | 6/2007 |
| WO | 2007/087374 A2 | 8/2007 |
| WO | 2007/092349 | 8/2007 |
| WO | 2007/096344 A1 | 8/2007 |
| WO | 2007/103132 A2 | 9/2007 |
| WO | 2007/106339 A2 | 9/2007 |
| WO | 2007/106856 A2 | 9/2007 |
| WO | 2007/118303 A2 | 10/2007 |
| WO | 2007/125336 A1 | 11/2007 |
| WO | 2007/126339 A1 | 11/2007 |
| WO | 2007/146101 A2 | 12/2007 |
| WO | 2008/008971 A1 | 1/2008 |
| WO | 2008/012519 A1 | 1/2008 |
| WO | 2008/017975 A1 | 2/2008 |
| WO | 2008/078750 A1 | 7/2008 |
| WO | 2008/084764 A1 | 7/2008 |
| WO | 2008/097062 A1 | 8/2008 |
| WO | 2008/128175 A1 | 10/2008 |
| WO | 2008/129740 A1 | 10/2008 |
| WO | 2008/129741 A1 | 10/2008 |
| WO | 2008/131079 A1 | 10/2008 |
| WO | 2008/131343 A1 | 10/2008 |
| WO | 2008/135548 A1 | 11/2008 |
| WO | 2008/135658 A2 | 11/2008 |
| WO | 2008/137489 A1 | 11/2008 |
| WO | 2008/146219 A1 | 12/2008 |
| WO | 2008/146220 A2 | 12/2008 |
| WO | 2008/146255 A2 | 12/2008 |
| WO | 2009/003295 A1 | 1/2009 |
| WO | 2009/008967 | 1/2009 |
| WO | 2009/014034 | 1/2009 |
| WO | 2009/016598 | 2/2009 |
| WO | 2009/016963 | 2/2009 |
| WO | 2009/023568 | 2/2009 |
| WO | 2009/023968 | 2/2009 |
| WO | 2009/038720 | 3/2009 |
| WO | 2009/056838 | 5/2009 |
| WO | 2009/059270 | 5/2009 |
| WO | 2009/064034 | 5/2009 |
| WO | 2009/089177 | 7/2009 |
| WO | 2009/107095 | 9/2009 |
| WO | 2009/117323 | 9/2009 |
| WO | 2009/118617 | 10/2009 |
| WO | 2009/121158 | 10/2009 |
| WO | 2009/123196 | 10/2009 |
| WO | 2009/125338 | 10/2009 |
| WO | 2009/132585 | 11/2009 |
| WO | 2009/137612 | 11/2009 |
| ZA | 9707751 | 3/1998 |

OTHER PUBLICATIONS

International Search Report mailed Apr. 12, 2005 in related PCT Application No. PCT/US1004/010915.
European Search Report dated Jun. 10, 2010 in related EP Application No. 04759316.5.

(56) References Cited

OTHER PUBLICATIONS

Israeli Office Action dated Nov. 19, 2009 in related Israeli Patent Application No. 171311.
Response dated Oct. 13, 2010 responding to Israeli Office Action dated Nov. 19, 2009 for Israeli Patent Application No. 171311.
Chinese Notice of Reexamination dated Jul. 27, 2010 in related Chinese Patent Application No. 2004/80012575.X.
Response dated Jul. 27, 2010 responding to Chinese Notice of Reexamination dated Jul. 27, 2010 in related Chinese Patent Application No. 2004/80012575.X.
EP Office Action dated Feb. 2, 2011 in related EP Patent Application No. 04 759316.5.
Office Action dated Nov. 19, 2001 issued in Israeli Patent Application No. 171311.
Response to Office Action dated Nov. 19, 2001 issued in Israeli Patent Application No. 171311.
Office Action dated Dec. 2, 2010 issued in Japanese Patent Application 2006-509834.
Response to Office Action dated Dec. 2, 2010 issued in Japanese Patent Application 2006-509834.
Office Action dated May 11, 2010 issued in Japanese Patent Application 2006-509834.
Response to Office Action dated May 11, 2010 issued in Japanese Patent Application 2006-509834.
Non-Final Rejection dated Feb. 19, 2003 for U.S. Appl. No. 09/819,083.
Amendment to Non-Final Rejection dated Feb. 19, 2003 for U.S. Appl. No. 09/819,083.
Preliminary Amendment filed May 2, 2005 for U.S. Appl. No. 11/119,378.
Non-Final Rejection dated Jun. 5, 2006 for U.S. Appl. No. 11/119,378.
Amendment to Non-Final Rejection dated Jun. 5, 2006 for U.S. Appl. No. 11/119,378.
Preliminary Amendment filed Aug. 29, 2005 for U.S. Appl. No. 11/212,916.
Non-Final Rejection dated Sep. 25, 2007 for U.S. Appl. No. 11/212,916.
Amendment to Non-Final Rejection dated Sep. 25, 2007 for U.S. Appl. No. 11/212,916.
Final Rejection dated Mar. 25, 2008 for U.S. Appl. No. 11/212,916.
Non-Final Rejection dated Jun. 19, 2008 for U.S. Appl. No. 11/332,517.
Non-Final Rejection dated Dec. 19, 2002 for U.S. Appl. No. 09/986,367.
Amendment to Non-Final Rejection dated Dec. 19, 2002 for U.S. Appl. No. 09/986,367.
Final Rejection dated Aug. 12, 2003 for U.S. Appl. No. 09/986,367.
Amendment to Final Office Action dated Aug. 12, 2003 for U.S. Appl. No. 09/986,367.
Advisory Action dated Mar. 8, 2004 for U.S. Appl. No. 09/986,367.
Non-Final Rejection dated Sep. 22, 2004 for U.S. Appl. No. 09/986,367.
Amendment to Non-Final Rejection dated Sep. 22, 2004 for U.S. Appl. No. 09/986,367.
Non-Final Rejection dated Jun. 26, 2008 for U.S. Appl. No. 11/366,811.
Office Action dated Jul. 21, 2011 for U.S. Appl. No. 12/583,578.
Response to Office Action dated Jul. 21, 2011 for U.S. Appl. No. 12/583,578.
Final Office Action dated Apr. 11, 2012 for U.S. Appl. No. 12/583,578.
Response to Final Office Action dated Apr. 11, 2012 for U.S. Appl. No. 12/583,578.
U.S. Office Action dated May 10, 2011 for U.S. Appl. No. 12/550,749.
Response to Office Action dated May 10, 2011 for U.S. Appl. No. 12/550,749.
Final Office Action dated Jan. 18, 2012 for U.S. Appl. No. 12/550,749.
Response to Final Office Action dated Jan. 18, 2012 for U.S. Appl. No. 12/550,749.
Office Action dated May 11, 2011 for U.S. Appl. No. 12/550,799.
Response to Office Action dated May 11, 2011 for U.S. Appl. No. 12/550,799.
Final Office Action dated Dec. 3, 2012 for U.S. Appl. No. 12/550,799.
Office Action dated Mar. 30, 2011 for U.S. Appl. No. 12/550,464.
Response to Office Action dated Mar. 30, 2011 for U.S. Appl. No. 12/550,464.
Office Action dated Oct. 28, 2011 for U.S. Appl. No. 12/550,464.
Response to Office Action dated Oct. 28, 2011 for U.S. Appl. No. 12/550,464.
Final Office Action dated May 29, 2012 for U.S. Appl. No. 12/550,464.
Response to Final Office Action dated May 29, 2012 for U.S. Appl. No. 12/550,464.
Office Action dated May 25, 2011 for U.S. Appl. No. 12/753,207.
Response to Office Action dated May 25, 2011 for U.S. Appl. No. 12/753,207.
Non-Final Office Action dated Jun. 25, 2008 for U.S. Appl. No. 11/346,622.
Response to Non-Final Office Action dated Jun. 25, 2008 for U.S. Appl. No. 11/346,622.
Final Office Action dated Jan. 6, 2010 for U.S. Appl. No. 11/346,622.
Response to Final Office Action dated Jan. 6, 2010 for U.S. Appl. No. 11/346,622.
Advisory Action dated Mar. 12, 2010 for U.S. Appl. No. 11/346,622.
Non-Final Office Action dated Sep. 30, 2010 for U.S. Appl. No. 11/346,622.
Response to Non-Final Office Action dated Sep. 30, 2010 for U.S. Appl. No. 11/346,622.
Final Office Action dated Jun. 13, 2011 for U.S. Appl. No. 11/346,622.
Response to Final Office Action dated Jun. 13, 2011 for U.S. Appl. No. 11/346,622.
Amendment to Non-Final Rejection filed Sep. 26, 2005 for U.S. Appl. No. 09/876,157.
Miscellaneous Action regarding Drawing Inconsistency dated Aug. 24, 2005 for U.S. Appl. No. 09/876,157.
Amendment to Non-Final Rejection dated Apr. 8, 2004 for U.S. Appl. No. 09/876,157.
Non-Final Rejection dated Apr. 8, 2004 for U.S. Appl. No. 09/876,157.
Response to Restriction Requirement dated Jul. 22, 2003 for U.S. Appl. No. 09/876,157.
Requirement for Restriction/Election dated Jul. 22, 2003 for U.S. Appl. No. 09/876,157.
Preliminary Amendment filed Jan. 7, 2002 for U.S. Appl. No. 09/876,157.
Amendment to Final Office Action dated Jan. 25, 2008 for U.S. Appl. No. 11/783,538.
Final Rejection dated Jan. 25, 2008 for U.S. Appl. No. 11/783,538.
Amendment to Non-Final Rejection dated Aug. 22, 2007 for U.S. Appl. No. 11/783,538.
Non-Final Rejection dated Aug. 22, 2007 for U.S. Appl. No. 11/783,538.
Non-Final Rejection dated Dec. 30, 2005 for U.S. Appl. No. 09/819,082.
Preliminary Amendment filed Feb. 15, 2001 for U.S. Appl. No. 09/819,082.
Amendment After Notice of Allowance filed Aug. 1, 2008 for U.S. Appl. No. 09/819,083.
Amendment to Final Office Action dated Jan. 24, 2008 for U.S. Appl. No. 09/819,083.
Final Rejection dated Jan. 24, 2008 for U.S. Appl. No. 09/819,083.
Amendment to Non-Final Rejection dated May 15, 2007 for U.S. Appl. No. 09/819,083.
Non-Final Rejection dated May 15, 2007 for U.S. Appl. No. 09/819,083.
Amendment to Final Office Action dated Dec. 22, 2006 for U.S. Appl. No. 09/819,083.
Final Rejection dated Dec. 22, 2006 for U.S. Appl. No. 09/819,083.

(56) References Cited

OTHER PUBLICATIONS

Amendment to Non-Final Rejection dated Mar. 24, 2006 for U.S. Appl. No. 09/819,083.
Non-Final Rejection dated Mar. 24, 2006 for U.S. Appl. No. 09/819,083.
Advisory Action dated Dec. 1, 2005 for U.S. Appl. No. 09/819,083.
Amendment to Final Office Action dated Sep. 1, 2005 for U.S. Appl. No. 09/819,083.
Final Rejection dated Sep. 1, 2005 for U.S. Appl. No. 09/819,083.
Amendment to Non-Final Rejection dated Dec. 15, 2004 for U.S. Appl. No. 09/819,083.
Non-Final Rejection dated Dec. 15, 2004 for U.S. Appl. No. 09/819,083.
Amendment to Non-Final Rejection dated Jan. 14, 2004 for U.S. Appl. No. 09/819,083.
Non-Final Rejection dated Jan. 14, 2004 for U.S. Appl. No. 09/819,083.
Illel, Brigette, et al. (1991), "Follicles Play an Important Role in Percutaneous Absorption," Journal of Pharmaceutical Sciences 80(5).
Finlay, A., et al., "A Fluorescence Photographic Photomeric Technique to assess Stratum Corneum Turnover Rate and Barrier Function in Vivo", British Journal of Dermatology, 1982, 107, 35-42.
Burgess, "Researchers Identify Key to Phototropism", Biophotonics International, Nov./Dec. 1999, pp. 22-23.
Green, C., et al. (1988), "311 nm UVB Phototherapy: an Effective Treatment for Psoriasis", Br J Dermatol. 119, pp. 694-696.
Callaghan et al. (1996), "Reactive Oxygen Species Inducible by Low-intensity Laser Irradiation Alter DNA Synthesis in the Hemopoietic Cell Line", U937, Lasers Surg. Med. 19(2):201-206.
Castro (Sep. 1983), "Effects of the Nd:YAG Laser on DNA Synthesis and Collagen Production in Human Skin Fibroblast Cultures", Annals of Plastic Surgery 11, pp. 3.
Ceccherelli et al. (1989), "Diode Laser in Cervical Myofascial Pain: A Double-blind Study Versus Placebo," The Clinical Journal of Pain 5:301-304.
Chung et al. (1996), "Histological Responses of Port Wine Stains in Brown Skin After 578 nm Copper Vapor Laser Treatment", Lasers Surg. Med. 18(4):358-366.
Roden, Dan, MD, "Electrophysiology, Pacing and Arrhythmia", Clin. Cardiol, 20, 285-290 (1997).
Bruer, Miklos M., "Ultrasonic Radiation for Hair Treatments", Cosmetics & Toiletries, vol. 113, pp. 67-75, Jun. 1998.
Webster, D. F, et al., "The Role of Ultrasound-Induced Cavitation in the 'In Vitro' Stimulation of Collagen Synthesis in Human Fibroblasts," Ultrasonics, pp. 33-37 (1980).
Castro, D. J., et al. (Dec. 1987), "Biostimulative Effects of Nd:YAG Q-Switch Dye on Normal Human Fibroblast Cultures: Study of a New Chemosensitizing Agent for the Nd: YAG Laser", Laryngoscope, 97(12), pp. 1454-1459.
Database WPI Week 200046 Derwent Publications Ltd., London, GB; AN 2000-511628; XP002373743 & JP 2000 202044 A (Yamana Co Ltd.) Jul. 25, 2000.
Draper, David, et al. (1995), "Temperature Changes in Deep Muscles of Humans During Ice and Ultrasound Therapies: an in Vivo Study", JOSPT 12(3).
Karu et al. (1996), "Effects of Monochromatic Low-intensity Light and Laser Irradiation on Adhesion of the HeLa Cells in Vitro", Lasers Surg. Med. 18(2):171-177.
Tachibana, Katsuro (1992), "Transdermal Delivery of Insulin to Allosxan-Diabetic Rabbits by Ultrasound Exposure", Pharmaceutical Research 9(7).
Edwards, (May 2001) "Keeping Up with the LEDs," Photonics Spectra.
Gann, Nancy, "Ultrasound: Current Concepts", Electrotherapy, vol. 11, No. 4, Jul./Aug. 1991.
Tur, Ethel, et al. (1991), "Percutaneous Penetration of Methy Nicotinate at Three Anatomic Sites: Evidence for an Appendagael Contribution to Transport?", Skin Pharmacol 4, pp. 230-234.
Heuber, F., et al. (1994), "Percutaneous Absorption of Estradiol and Progesterone in Normal and Appendage-Free Skin of the Hairless Rat: Lack of Importance of Nutritional Blood Flow", Skin Pharmacol 7, pp. 245-256.
Freeman et al. (2004), "NGF Deprivation-induced Gene Expression: After Ten Years, Where Do We Stand?," Chapter 8 in Progress in Brain Research 146, Elsevier B.V., 111-126.
Reddy, G. Kesave, et al. (1998), "Laser Photostimulation of Collagen Production in Healing Rabbit Achilles Tendons", Lasers in Surgery and Medicine, 22, pp. 281-287.
Nicolau, G., et al. (1987), "Deposition of Viprostol (a Synthetic PGE2 Vasodilator) in the Skin Following Topical Administration to Laboratory Animals", Xenobiotica 17(9), pp. 1113-1120.
Gao et al. (Jul. 13, 2004), "Induction of Phase 2 Genes by Sulforaphane Protects Retinal Pigment Epithelial Cells Against Photooxidative Damage", PNAS 101(28:10446-10451).
Giamundo (May 2001), "A Little Enlightenment," Photonics Spectra.
Menon, Gopinathan K., et al. (1994), "High-Frequency Sonophoresis: Permeation Pathways and Structural Basis for Enhanced Permeability", Skin Pharmacol. 7, pp. 130-139.
Gupta et al. (1998), "The Use of Low Energy Photon Therapy (LEPT) in Venous Leg Ulcers: A Double-Blind, Placebo-Controlled Study", Dermatol. Surg. 24, pp. 1383-1386.
Gupta, A. K, et al. (1997) "The Use of Low Energy Photon Therapy in the Treatment of Leg Ulcers-A Preliminary Study," Journal of Dermatological Treatment 8(2), pp. 103-108.
Van Weelden, H., et al. (1990), "Comparison of Narrow band UV-B Phototherapy and PUVA Photochemotherapy in the Treatment of Psoriasis", Acta Dermatol Venereol (Stockh) 70, pp. 212-215.
Schaefer, Hans, et al. (1996), "Skin Barrier Principles of Percutaneous Absorption", pp. 153 and 175.
Benson, Heather A., et al, (1991), "Influence of Ultrasound on the Percutaneous Absorption of Nicotinate Esters," Pharmaceutical Research 8(2), pp. 204-209.
Benson, Heather A., et al. (1988), "Transmission of Ultrasound Energy Through Topical Pharmaceutical Products", Physiotherapy 74(11), pp. 587-589.
Huang et al. (Aug. 2004), "Downregulation of ATP Synthase Subunit-6, Cytochrome c Oxidase-III, and NADH Dehydrogenase-3 by Bright Cyclic Light in the Rat Retina". Investigative Ophthalmology & Visual Science 45(8):2489-2496.
Omura, T., "Hemoprotein H-450 Identified as a Form of Cytocherome P-450 Having an Endorgenous Ligand at the 6th Coordination Position of the Heme (Abstract)", J. Biochem (Tokyo), Nov. 1984; 96(5)1491-1500.
Kao, Jr., et al. (1988), "In Vitro Percutaneous Absorption in Mouse Skin: Influence of Skin Appendages", Toxicology and Applied Pharmacology 94, pp. 93-103.
Ferry, James, et al. (1990), "Relationship Between Contact Time of Applied Dose and Percutaneous Absorption of Minoxidil from a Topical Solution". Journal of Pharmaceutical Sciences 79(6), pp. 483-486.
Kumar, Saran, et al. (1992), "Studies of In Vitro Skin Permeation and Retention of a Leukotriene Antagonist from Topical Vehicles with a Hairless Guinea Pig Model", Journal of Pharmaceutical Sciences, vol. 81, No. 7.
Mitragotri, Samir, et al. (Jun. 1995), "A Mechanistic Study of Ultrasonically-Enhanced Transdermal Drug Delivery," Journal of Pharmaceutical Sciences, vol. 84, No. 6.
Egbaria, Kamel, et al. (1992), "Absorption of Fluorescein Dyes on Albumin Microspheres", Pharmaceutical Research 9, pp. 629-635.
Final Office Action dated Dec. 9, 2011 for U.S. Appl. No. 12/753,207.
Response to Final Office Action dated Dec. 9, 2011 for U.S. Appl. No. 12/753,207.
Response to Final Office Action dated Dec. 3, 2012 for U.S. Appl. No. 12/550,799.
Notice of Restriction dated Mar. 29, 2006 for U.S. Appl. No. 10/665,390.
Response to Restriction dated Mar. 29, 2006 for U.S. Appl. No. 10/665,390.
Non Final Rejection dated Aug. 21, 2006 for U.S. Appl. No. 10/665,390.

(56) References Cited

OTHER PUBLICATIONS

Non Final Rejection dated Jan. 5, 2006 for U.S. Appl. No. 10/903,483.
Amendment to Non-Final Rejection dated Jan. 5, 2006 for U.S. Appl. No. 10/903,483.
Non Final Rejection dated Sep. 25, 2006 for U.S. Appl. No. 10/903,483.
Amendment to Non-Final Rejection dated Sep. 25, 2006 for U.S. Appl. No. 10/903,483.
Appeal Brief filed Jan. 28, 2008 for U.S. Appl. No. 10/903,483.
Non Final Rejection dated May 22, 2008 directed towards U.S. Appl. No. 10/903,483.
Non Final Rejection dated Jul. 18, 2007 for U.S. Appl. No. 11/205,316.
Amendment to Non-Final Rejection dated Jul. 18, 2007 for U.S. Appl. No. 11/205,316.
Final Rejection dated Jun. 9, 2008 for U.S. Appl. No. 11/205,316.
Non Final Rejection dated Oct. 19, 2007 for U.S. Appl. No. 11/272,042.
Amendment to Non-Final Rejection dated Oct. 19, 2007 for U.S. Appl. No. 11/272,042.
Final Rejection dated Jun. 6, 2008 for U.S. Appl. No. 11/272,042.
Non-Final Rejection dated Jun. 8, 2010 for U.S. Appl. No. 12/583,562.
Amendment to Non-Final Rejection dated Jun. 8, 2010 for U.S. Appl. No. 12/583,562.
Official Notification dated Dec. 3, 2008 for Israeli Patent Application No. 171311.
First Office Action dated Mar. 10, 2006 for Chinese Patent Application No. 200480012575.X.
Second Office Action dated Nov. 2, 2007 for Chinese Patent Application No. 200480012575.X.
Official Notification regarding clarification of claims dated Sep. 19, 2002 for PCT Patent Application No. PCT/US02/26627.
Request for Rectification of Obvious Errors in the International Patent Application and Submission of Copy of Request to Record Change of Agent's Address dated Sep. 27, 2002 for PCT Patent Application No. PCT/US02/26627.
International Search Report dated May 16, 2003 for PCT Patent Application No. PCT/US02/26627.
Written Opinion dated Feb. 5, 2004 for PCT Patent Application No. PCT/US02/26627.
International Search Report dated May 8, 2003 for PCT Patent Application No. PCT/US02/35839.
International Preliminary Examination Report dated Oct. 7, 2003 for PCT Patent Application No. PCT/US02/35839.
First Statement of Proposed Amendments dated Oct. 27, 2005 for Australian Patent Application No. 2002326716.
Examiner's Report dated Mar. 22, 2007 for Australian Patent Application No. 2002326716.
Office Action dated Aug. 2, 2006 for Canadian Patent Application No. 2457590.
Response to Office Action dated Aug. 2, 2006 for Canadian Patent Application No. 2457590.
Office Action dated Apr. 30, 2007 for Canadian Patent Application No. 2457590.
Response and Amendment to Office Action dated Apr. 30, 2007 for Canadian Patent Application No. 2457590.
Office Action dated Jan. 31, 2008 for Canadian Patent Application No. 2457590.
Request for Reinstatement for Failure to Respond to Office Action dated Jan. 31, 2008 for Canadian Patent Application No. 2457590.
Office Action dated Oct. 2, 2009 for Canadian Patent Application No. 2457590.
Response to Office Action dated Oct. 2, 2009 for Canadian Patent Application No. 2457590.
Office Action dated Dec. 30, 2010 in Canadian Patent Application No. 2,457,590.
Office Action dated May 6, 2010 in Canadian Patent Application No. 2,457,590.
Response to Office Action dated May 6, 2010 in Canadian Patent Application 2,457,590.
Office Action dated Aug. 25, 2006 for European Patent Application No. 02761449.4-1216.
Response to Office Action dated Aug. 25, 2006 for European Patent Application No. 02761449.4-1216.
Office Action dated Jul. 31, 2007 for European Patent Application No. 02761449.4-1216.
Response to Office Action dated Jul. 31, 2007 for European Patent Application No. 02761449.4-1216.
Heikkila, H., Stubb, S., & Kiistala, U. (1996). "Nail growth measurement employing nail indentation—an experimentall follow-up study of nail growth in situ," Clinical and Experimental Dermatology, 21(2). pp. 96-99.
Zimny, S. & Pfohl M. (2005). "Healing tmes and predicton of wound healing in neuopathic diabetic ulcers: a prospective study," Experimental and Clinical Endocrinology & Diabetes, 113(2). pp. 90-93.
Martinez, D., et al. "Wound healing response of the medial collateral ligament during hindlimb unweighting in young rats."
Rosenburg, L. (2003). "Wound healing, growth factors," Emedicine.
Mitragotri, S. (2000). "Synergistic effect of enhancers for transdermal drug delivery," Pharmaceutical Research, 17(11). pp. 1354-1359.
Mitragotri, G. et al. (2000). "Analysis of ultrasonically extracted interstitial fluid as a predictor of blood g levels," Journal of Applied Physiology, 89(3). pp. 961-966.
Anvar M.D., et al. (2000). "Vascular and stromal features in the skin of the lower limb in patients with critical limb ischaemia," European Journal of Vascular and Endovascular Surgery, 20(2). pp. 125-131.
Eichler, W., et al. (2000). "Changes of interstitial fluid volume in superficial tissues detected by a miniature ultrasound device," Journal of Applied Physiology. 89)1). pp. 359-363.
Mitragotri. S., et al. (2000). "Transdermal extraction of analytes using low-frequency ultrasound," Pharmaceutical Research, 17(4). pp. 466-470.
Mali. M., et al, (2000). "Two children with suspected primary messenteric vessels—a case report," Nihon Rinsho Meneki Gakkai Kaishi, 23(2) pp. 148-155.
Mitragotri, S. (2000). "Synergistic effect of low-frequency ultrasound and sodium lauryl sulfate on transdermal trasport," Journal of Pharmaceutical Science, 89(7). pp. 892-900.
Mitragotri, S., & Kost, J. (2000). "Low-frequency sonophoresis: A noninvasive method of drug delivery and diagnostics," Biotechnology in Progress, 16(3). pp. 488-492.
Tayor, B.K., et al. (2000). "Opioid inhibition of formalin-induced changes in plasma extravasation and bood flow in rats," PAIN, 84(2-3). pp. 263-270.
Fang, J., et al. (1999). "Effect of low-frequency ultrasound on the in vitro percutaneous absorption of clobetasol 17-propionate," International Journal of Pharmaceutics, 191(1). pp. 33-42.
Shoab, S.S., et al. (1999). "Plasma VEGF as a marker of therapy in patients with chronic venous diseases with oral micronised flavonoid fraction—a pilot study," European Journal of Vascular and Endovascular Surgery, 18(4). pp. 334-338.
Meidan, V.M., et al. (1999). "Ultrasound -enhanced diffusion into coupling gel during phonophoresis of 5-fluorouracil," International Journal of Pharmaceutics, 185(2). pp. 205-213.
Terai, M., et al. (1999). "Vascular endothelia growth factor in acute Kawasaki disease," American Journal of Cardiology, 83(3). pp. 337-339.
Singer, A.J., et al. (1999). "The effects of low-frequency ultrasound on *Staphylococcus epidermidis*," Current Microbiology, 38(3). pp. 194-196.
Foldvari, M., et al. (1998) "Liposome encapsulated postaglandin E1 in erectile dysfunction: Correlation in vitro delivery through foreskin and efficacy in patients," Urology, 52(5). pp. 838-843.
Wu, J., et al. (1998). "Defects generated in human stratum corneum specimens by ultrasound," Ultrasound in Medicine and Biology, 24(5). pp. 705-710.
Li, J., Lewis, T.N., & Prausnitz, M.R. (1998) "Non-invasive assessment and control of ultrasound-mediated membrane permeabilization," Pharmaceutical Research, 15(6). pp. 918-924.

(56) References Cited

OTHER PUBLICATIONS

Pedder, V.V., et al. (1998). "Rationale of noninvasive method of drug administration at the prelymphatic," MED TEKH, 2 pp. 18-23.

Sigfridsson et al. (1995), "Electrogenetic light reactions in photsystem I: resolution of electron-transfers rates between the iron-sulfer centers," Proc. National Acadamy of Science U.S.A., pp. 3456-3462. (Abstract).

Voigt et al. (2002), "Spectral Substructure and Excitonic Interactions in the Minor Photosystem II Antenna Complex CP29 Revealed by Nonlinear Polarization Spectroscopy in Frequency Domain," Biochemistry, pp. 3049-3056. (Abstract).

Dacher et al. (2001), "Combinded NPLC-MS and HPLC-NMR on-line coupling for the separation and determination of lutein and zeaxanthin stereoisomers in spinach and in retina," Analytical Chemistry, pp. 667-674. (Abstract).

Varani et al. (2001), "Inhibition of type I procollagen synthesis by damages collagen in photoaged skin and by collagenase-degraded collagen in vitro," American Journal of Pathology, pp. 931-941. (Abstract).

Yu et al. (1997), "Photomodulation of oxidative metabolism and electron chain enzymes in rat liver mitochondria," Photochem. Photobiol., pp. 866-871. (Abstract).

Quan et al. (2002), "Connective tissue growth factor: expression in human skin in vivo and inhibition by ultraviolet radiation," Journal of Investigative Dermatology, pp. 402-408. (Abstract).

Boudjelal et al. (2002), "Retinoid Signaling Is Attenuated by Protassome-Mediated Degradation of Retinoid Receptors in Human Keratinocyte HaCaTCells," Exp. Cell. Res., pp. 130-137. (Abstract).

Loschinger et al. (1998), "Stimulation of protein kinase A activity and induced terminal differentiation of human skin fibroblasts in culture by low-frequency electromagnetic fields," Toxicol. Lett., pp. 369-76. (Abstract).

Bourguignon, GJ. and Bourguignon, LY. (1987), "Electric stimulation of protein and DNA synthesis in human fibroblasts," FASBERS J., pp. 398-402. (Abstract).

Bourguignon et al. (1989), "Electric stimulation of human fibroblasts causes an increase in Ca2+influx and the exposure of additional insulin receptors," Journal of Cellular Physiology, pp. 379-385. (Abstract).

Quan et al. (2001), "Ultraviolet irradiation blocks cellular responses to transforming growth factor-beta by down-regulating its type-II receptor and inducing Smad7," Journal of Biological Chemistry, pp. 26349-26356. (Abstract).

Neudecker, B.A., et al. (2004) "Abberant Serum Hyaluronan and Hyaluronidase Levels In Scleroderma," The British Journal of Dermatology pp. 469-476.

Formby, Bent, et al. (2002) "Lactate Stimulates Hyaluronan and CD44 Expression in Cultured Fibroblasts: the Warburg Effect Revisited," Experimental Cell Research May 15, 2002;276(1):24-31.

Stern, Robert. (2001) "Minireview The Mammalian Hyaluronidases: Introductory Remarks" pub. by Elsevier Science B.V., Matrix Biology p. 497.

Csoka, Antonei, B. (2001) "Minireview The Six Hyaluronidase-like Genes in Human and Mouse Genomes" pub. by Elsevier Science B.V., Matrix Biology pp. 499-508.

Boh, Erin E. (2001) "Free Radicals and Aging Skin" Cosmetic Dermatology vol. 14 No. 12 Dec. 2001 pr. 37-40.

Lubart, R. et al. (1992) "Effect of Light on Calcium Transport in Bull Sperm Cells" Journal of Photochemuistry Photobiology B. Sep. 15, 1992;15(4):337-41.

Webster, Guy (2001) "Acne Pathogenesis & update on Therapy" Jujisawa Healthcare, Inc. Lectureship Series IN Dermatology [pamphlet] pp. 1-24.

Loschinger, Monika (1998) "Stimulation of Protein Kinase A Activity and Induced Terminal Differentiation of Human Skin Fibroblasts in Culture by Low-Frequency Electromagnetic Fields" Toxicol Lett. Aug. 1998; pp. 96-97;369-76.

Bedi, Monika K. (2002) "Herbal therapy in dermatology" Archives of Dermatology Feb. 2002 pp 138(2).232-42.

Yu, Wei. (1997) "Photomodulation of Oxidative Metabolism and electron Chain Enzymes in Rat Liver Mitochondria" Photochemistry and Photobiology, Dec. 1997;66(6):866-71.

Barber, James (2002) "Short communication: P680 What is it and Where is it?" Bioelectrochemistry, vol. 55, No. 1, Jan. 2002, pp. 135-138(4).

Matsuad, Tatsuru et al. (2002) "Biosynthesis and distribution of Chlorophyll Among the Photosystems During recovery of the Green Alga *Dunaliella Salina* From Irradiance Stress" Plant Physiology. Feb. 2002;128(2):603-14.

De Mattei, M, et al. (2001) "Effect of Pusled Electromagnetic Fields on human Articular Chodrocyte Proliferation" Connective Tissue Research 2001:42(4):269-79.

Krishtalik, LI et al. (2000) "Effects of Medium Polarization and Pre-Existing Field on Activation Energy of Enzymatic Charge-Transfer Reactions" Biochimica Biophysica Acta. Jul. 20, 2000;1459(1):88-105.

Edwards, AM, Silva, E. "Effect of Visible Light On Selected Enzymes, Vitamins and Amino Acids" Journal of Photochemistry Photobiology B. Oct. 2001;63(1-3):126-31.

Sommer, Andrei P. "Abstracts From the 1st International workshop on Nearfield Optical Analysis, Reisenberg, Germany, Nov. 2000" Journal of Clinical Laser Medicine & Surgery vol. 19 No. 2 2001.

Ishigaki, Y., et al. (1999). "Development and Characterization of a DNA Solar Dosimeter," Journal of Photochemistry and Photobiolgy, 50. pp, 184-188.

Gross, A. (1999). "Entering the Japanese Medical Device Market: The latest trends mean even better opportunities for foreign medical technology manufacturers," Medical Devicelink, Accessed: Dec. 15, 2001.

Gross, A., & Dyson, P. (1996). "Changing Regulatory Climate Improves Korean Market of U.S. Companies," Medical Device and Diagnostic Industry.

LeDoux, S.P., & Wilson, G.L. (2001). "Base Excision Repair of Mitochondrial DNA Damage in Mammalian Cells," Progress in Nucleic Acid Research and Molecular Biology, 66. pp. 273-284.

Turnbull, D., & Lightowlers, R. (2001). "Might Mammalian Mitochondria Merge?" Nature Medicine, 7(6). pp. 895-896.

Nakada, K., et al. (2001). "Inter-mitochondrial complementation: Mitochondria-specific system preventing mice from expression of disease phenotypes by mutant mtDNA," Nature Medicine, 7(8). pp. 934-940.

Vogel, W.F. (2001) "Collagen-receptor signaling in health and disease," European Journal of Dermatology, 11(6). pp. 506-514.

Curat, C., et al. (2001) "Mapping of eptiopes in discoidin domain receptor 1 critical for collagen binding," Journal of Biological Chemistry, 6(49).

Hou, G., Vogel, W., & Bendeck, M.P. (2001), "The discoidin domain receptor tyrosine kinase DDR1 in arterial wound repair," Journal of Clinical Investigation, 107(6). pp. 727-735.

Chin, G.S., et al. (2000). "Cellular signaling by tyrosine phosphorylation in keloid and normal human dermal fibroblasts," Plastic Reconstructive Surgery, 106(7). pp. 1532-1540.

Weiner, H.L., et al. (2000). "Consistent and selective expression of the discoidin domain receptor-1 tyrosine kinase in human brain tumors," Neurosurgery, 47(6). pp. 1400-1409.

Chin, G.S., et al. (2000). "Differential expression of receptor tyrosine kinases and Shc in fetal and adult rat fibroblasts: Toward defining scarless versus scarring fibroblast phenotypes," Plastics Reconstructive Surgery, 105(3). pp. 972-979.

Vogel, W., et al. (2000). "Discoidin domain receptor 1 is activated independently of beta 1 integrin," Journal of Biological Chemistry 275(8). pp. 5779-5784.

Vogel, W. (1999). "Discoidin domain receptors: Structural relations and functional implications, " FASEB Journal, 13. pp. 77-82.

Norman, J.T., & Fine, L.G. (1999). "Progressive renal disease: Fibroblasts, extracellular matrix, and integrins," Experimental Nephrology, 7(2). pp. 167-177.

Shrivastava, A., et al. (1997). "An orphan receptor tyrosine kinase family whose members serve as nonintegrin collagen receptors," Molecular Cell, 1(1). pp. 25-34.

Vogel, W., et al. (1997). "The discoidin domain receptor tyrosine kinases are activated by collagen," Molecular Cell, 1 (1). pp. 13-23.

(56) References Cited

OTHER PUBLICATIONS

Sakuma, S., et al. (1996). "Receptor protein tyrosine kinase DDR is up-regulated by p53 protein," FEBS Letters, 2. pp. 398, 165-169.
Hardell, L. et al. (2001). "Ionizing radiation, cellular telephones and the risk for brain tumors," European Journal of Cancer Prevention, 10(6). pp. 523-529.
Seishima M., Oyama Z., & Yamamura, M. (2002), "Cellular phone dermatitis," Archives of Dermatology. 138(2), pp. 272-273.
Di Carlo, A., et al. (2002). "Chronic electromagnetic field exposure decreases HSP70 levels and lowers cytoprotection, " Journal of Cellular Biochemistry, 84(3). pp. 447-454.
French, P.W., et al. (2001). "Mobile phones, heat shock proteins and cancer," Differentiation, 67(4-5), pp. 93-97.
Frumkin, H., et al. (2001). "Cellular phones and risk of brain tumors," CA: A Cancer Journal for Clinicians, 51(2). pp, 137-141.
Moustafa, Y.M., et al. (2001). "Effects of acute exposure to the radiofrequency fields of cellular phones on plasma lipid peroxide and antioxidase activities in human erythrocytes," Journal of Pharmaceutical and Biomedical Analysis, 26(4). pp. 605-608.
Chiladakis, J.A., et al. (2001). "In-vivo testing of digital cellular telephones in patients with implantable cardioverter-defibrillators," European Heart Journal, 22(15). pp. 1337-1342.
Santini, R., et al. (2001). "Symptoms reported by mobile cellular telephone users." Pathological Biology, 49(3). pp. 222-226.
Roti, J.L., et al. (2001). "Neoplastic transformation in C3H 10T(1/2) cells after exposure to 835.62 MHz FDMA and 847.74 CDMA radiations," Radiation Research, 155(1-2). pp. 239-247.
Wainwright, P. (2000). "Thermal effects of radiation from cellular telephones," Physics in Medicine and Biology, 152 (3). pp. 293-302.
Adey, W.R., et al. (1999). "Spontaneous and nitrosourea-induced primary tumors of the central nervous system in Fischer 344 rats chronically exposed to 836 MHz modulated microwaves," Radiation Research, 152(3). pp. 293-302.
Robert, E. (1999). "Intrauterine effects of electromagnetic fields— (low frequency, mid-frequency RF, and microwave): A review of epidemiologic studies," Teratology, 59(4). pp. 292-298.
De Seze, R., Fabbro-Peray, P., & Miro, L. (1998). "GSM radiocellular telephones do not disturb the secretion of antepituitary hormones in humans," Bioelectromagnetics, 19(5). pp. 271-278.
Malyapa, R.S., et al. (1997). "Measurement of DNA damage after exposure to electromagnetic radiation in the cellular phone communication frequency band (835.62 and 847.74 MHz)," Radiation Research, 148(6). pp. 618-627.
Litovitz, T.A, et al. (1997). "Bioeffects induced by exposure to microwaves are mitigated by superposition of ELF noise," Bioelectromagnetics, 18(6). pp. 422-430.
Omura, Y., & Losco, M. (1993). "Electro-magnetic fields in the home environment (color TV, computer monitor, microwave oven, cellular phone, etc) as potential contributing factors for the induction of oncogen C-fos Ab1, oncogen C-fos Ab2, integrin alpha 5 beta 1 and development of cancer, as well as effects of microwave on amino acid composition of food and living human brain," Acupuncture and Electro-Theraputics Research, 18(1). pp. 33-73.
Knave, B. (2001). "Electromagnetic fields and health outcomes," Annals Academy of Medicine Singapore, 30(5). pp. 489-493.
De Seze, R., et al. (1999). "Evaluations in humans of the effects of radiocellular telephones on the circadian patterns of melatonin secretion, a chronobiological rhythm marker," Journal of Pineal Research, 27(4). pp. 237-242.
Fluhr, J.W., et al. (1999). "In-vitro and in-vivo efficacy of zinc acetate against propionibacteria alone and in combination with erythromycin," Zentralbl Bakteriol, 289(4). pp. 445-456.
Itoh, Y., et al. (2001). "Photodynamic therapy of acne vulgaris with topical delta-aminolaevulinic acid and incoherent light in Japanese patients," British Journal of Dermatology, 144(3). pp. 575-579.
Lang, K., et al. (2001). "Aminolevulinic acid: Pharmacological profile and clinical indication," Expert Opinion on Drug Discovery, 10(6). pp. 1139-1156.
Van Remmen, H. & Richardson, A. (2001). "Oxidative Damage to Mitochondria and Aging," Experimental Geology 36, pp. 957-968.

Rice B.W., et al. (2001), "In Vivo Imaging of Light-emitting Probes," Journal of Biomedical Optics 6(4) pp. 432-440.
Moretti, M. (2001). "ICN Develops Integrated Skin Treatment Package," Aesthetic Buyers Guide Nov. 2001.
Leyden, J., et al. (1999). "Finasteride in the Treatment of Men with Frontal Male Pattern Hair Loss," Journal of the American Academy of Dermatology 40(6). pp. 930-937.
Sommer, A.P, et al. (2001). "Biostimulatory Windows in Low-Intensity Laser Activation: Lasers, Scanners, and NASA's Light-Emitting Diode Array System," Journal of Clinical Laser Medicine and Surgery 19(1). pp. 29-33.
Troy, T. (2002). "Fluorescent Pulsed Light Makes Foray," Dermatology Times Jan. 2002.
Panteleyev, A., Jahoda, C., & Christiano, A. (2001). "Hair Follicle Predetermination," Journal of Cell Science 114. pp. 3419-3431.
Yoon, J.H., et al. (2000). "The DNA Damage Spectrum Produced by Simulated Sunlight," Academic Press, pp. 681-693.
Draper, B., et al. (2002). "MNPs and TIMP-1 are Differentially Expressed Between Acute Murine Excisional and Laser Wounds," Lasers in Surgery and Medicine 30, pp. 106-116.
Takemura et al.(1998), "Enhanced Interleukin 6 Production by Cultured Fibroblasts from Patients with Systemic Sclerosis in Response to Platelet Derived Growth," The Journal of Rheumatology, pp. 1534-1539.
Czuwara et al. (2001), "Differential regulation of transforming growth factor-β receptors type I and II by platelet-derived growth factor in human dermal fibroblasts," British Journal of Dermatology, 569-575.
Loftsson et al. (1995), "Fatty acids from cod-liver oil as skin penetration enhancers," Die Pharmazie, pp. 271-773.
Stahl et al. (2000), "Carotenoids and carotenoids plus vitamin E protect against unltraviolet light-induced erythema in humans," The American Clinical Journal of Nutrition, pp. 795-798.
Gambichler et al. (2001), "Ultraviolet protection by summer textiles. Ultraviolet transmission measurements verified by termination of the minimal erythema dose with solar simulated radiation," British Journal of Dermatology, pp. 484-489.
Stahl et al. (2001), "Dietary Tomato Pasta Protects against Ultraviolet Light-Induced Erythema in Humans," Biochemical and Molecular Action of Nutrients Research Communication, pp. 1449-1451.
Lee et al. (2000), "Carotenoid Supplementation Reduces Erythema in Human Skin After Simulated Solar Radiation Exposure," Society of Experimental Biology and Medicine, pp. 170-174.
Moy et al. (2000), "Incresed Glycosaminolycans Production in Sclersoing Basal Cell Carcinoma-Derived Fibroblasts and Stimulation of Normal Skin Fibrolast Glycosaminoglycans Production by a Cytokine-Derived from Sclerosing Basal Cell Carcinoma," Dermatolgoic Surgery, pp. 1029-1035.
Takehara, K. (2000), "Grown regulation of skin fibroblasts," Journal of Dermatolgial Science, pp. 70-74.
Loftsson, T. (1989), "Effect of choline esters and oleic acid on the penetration of acyclovir, estradiol, hydrocortisone, nitroglycerin, retinoic acid and trifluorothymidine across hairless mouse skin in vitro," Acta. Pharm. Nord., pp. 279-286.
Masson et. al. (2000), "Marine lipids for prodrugs, soft compounds and other pharmaceutical applications," Pharmazie, pp. 172-177.
Gross et al. (1978), "Comprehensive compilation of empirical ultrasonic properties of mammalian tissues," Journal of the Acoustical Society of America, pp. 423-457.
Fei et al. (1986), "Ultrasonic backscatter from bovine tissues:Varation with pathology," Journal of the Acoustical Society of America, pp. 166-172.
Fei, D and Shung, K. (1986), "Ultrasonic backscatter from bovine tissues," Journal of the Acoustical Society of America, pp. 871-876.
Chivers, R. and Parry R.(1978), "Ultrasonic velocity and attenuation in mammal an tissues," Journal of the Acoustical Society of America, pp. 940-954.
de Weerd et al. (2002), "Pathways for Energy transfer in the Core Light Harvesting Complexes CP43 and CP 47 of Photosystem II," Biophysical Journal, pp. 1586-1597.
Fluhr et al. (1999), "In-vitro and in-vivo Efficacy of Zinc Acetate against Propionibacteria Alone and in Combination with Erythromycin," Zent. bl. Bakerologie, pp. 445-456.

(56) References Cited

OTHER PUBLICATIONS

Lang et al. (2001), "Aminolevulinic acid: pharmacological profile and clinical indication," Expert Opinion Investigative Drugs, pp. 1139-1156.
Yakushevska et al. (2001), "Supermolecular organization of photosystem II and its associated light-harvesting antenna in *Arabidopsis thalinana*," European Journal of Biochemistry, pp. 6020-6028.
Polivka et al, (2002), "Carotenoid Si State in a Recombinant Light-Harvesting Complex of Photosystem II," Biochemistry, pp. 439-450.
Vander Meulen et al. (2002), "Calcium Depletion Modifies the Structure of the Photosystem II O2-Evolving Complex," Biochemistry, pp. 958-966.
Park et al. (2000), "Epidremal Growth (EGF) Antagonizes Transforming Growth Factor (TGF)-β1-Induced Collagen Lattice Contraction by Human Skin Fibrolasts," Biological and Pharmaceuticals Bulleetin, pp. 1517-1520.
Diffey et al. (2000), "In vitro assessment of the broad-spectrum ultraviolet protection of sunscreen products," Journal of the American Academy of Dermatology, pp. 1024-1035.
Zhu et al. (1997), "Photo-Irradiation Improved Functional Preservation of the Isolated Rat Heart," Lasers in Surgery and Medicine, pp. 332-339.
Yu et al. (1997), "Improvement of Host Response to Sepsis by Photobiomodulation," Lasers in Surgery and Medicine, pp. 262-268.
Shapiro, J and Price, V. (1998), "Hair Regrowth: Therapeutic Agents," Dermatologic Therapy, pp. 341-356.
El Sayed, S and Dyson, M. (1990), "Comparision of the Effect of Multiwavelength Light Produced by a Cluster of Semiconductor Diodes and of Each Individual Diode on mast Cell Number and Degranulation in Intact and Injured Skin," Lasers in Surgery and Medicine, pp. 559-568.
Huang et al. (2002), "Two-Photon Fluorescence Spectroscopy and Microscopy of NAD(P)H and Flavoprotein," Biophysical Journal, pp. 2811-2825.
Yamazaki et al. (1992), "Sleeetive Chemical Modification of Amino Acid Residues in the Flavin Adrenie Dinucleotide Binding Site of Nadph-Ferredoxin Reductase," Internternational Journal of Biochemistry, pp. 223-228.
Andersson et al. (1998), "Autofluoresence of living cells," Journal of Microscopy, pp. 1-7.
Chen et al. (2002), "New Technology for Deep Light Distribution in Tissue for Phototherapy," The Cancer Journal, pp. 154-163.
Baena-Gonzalez et al. (2001). "Cloroplast Transcription at Different Light Intensities. Glutathione-Mediated Phosphorylation of the Major RNA Polymerase Involved in Redox-Regulated Organellar Gene Expression," Plant Physiology, pp. 1044-1052.
Cheng, K. and Goldman, R. (1998), "Electronic Field and Proliferanon in a Dermal wound Model: Cell Cycle Kinetics," Bioelectromagnetics, 68-74.
Stough et al. (2002), "Finasteride improves male pattern hair loss in a randomized study in indentical twins," European Journal of Dermatology, pp. 32-37.
Todd et al. (2001), "Electrical Stimulation of Transforming Growth Factor-β1 Secretion by Human Dermal Fibroblasts and the U937 Human Monocyctic Cell Line," pp. 693-701.
Unholzer, A and Korting, H. (2002), "High Frequency Ultrasound in the Evaluation of Pharmacological Effects on the Skin," Skin Pharmacology and Applied Skin Physiology, pp. 71-84.
Pelle et al. (2002), "Cigareete Smoke-Inducted Lipid Peroxidation in Human Skin and its Inhibition by Topically Applied Antioxidants," Skin Pharmacology and Applied Skin Physiology, pp. 63-68.
Garbaers et al. (2001), "Mössbauer study of iron centers in D1/D2/Cyt b 559 complexes isolated from photostem II of spinach," European Biophysics Journal, pp. 485-493.
O.Ishiawa et al. (1997), "Morphological and biochemical analyses on fibroblasts and self-produced collagens in a novel three dimensional culture," British Journal of Dermatology, pp. 6-11.

Harmon, C. and Nevins, T. (1994), Biophasic Effect of 1, 25-Dihyoxyvitamin D on Human Hair Follicle Growth and Hair Fiber Production in Whole Organ Cultures, Journal of Investigative Dermatology pp. 318-322.
Reiss, S. (2002), "Photodynamic Therapy: Reaching Beyond Cancer," Biophotonics International Journal; pp. 48-54.
Lahjomri et al. (1997). "Pulsed Photoacoustic Study of the Diffusion of Chromophores in Human Skin," Photochemistry and Photobiology, pp. 292-302.
Agramonte, A. (2001), "The Inside History of a Great Medical Discovery," Military Medicine, pp,66-78.
Tsukahara et al. (2001), "Dirunal variation affects age-related profile in skin thickness," Journal of Cosmetic Science, pp. 391-397.
Ernst, E. and Huntley, A. (2000), "Tea Tree Oil: A system Review of Randomized Clinical Trials," Research in Complementary Medicine, pp. 17-20.
Masuda et al. (2002), "Biosynthesis and distribution of chlorophyll among the photosystems during recovery of the green alga *Dunaliella salina* from irradiance stress," Plant Physiology, pp. 603-614. (Abstract).
Joet et al. (2002), "Cyclic Electron Flow around Photosystem I in C(C) Plants. In Vivo Control byu the Redox State of Chloroplasts and Involvement of the NADH-Dehydroense Complex," pp. 760-769. (Abstract).
Christen et al. (2000), "Delayed Fluorescence emitted from light harvesting complex II and photosystem II of higher plants in the 100 ns-5 mircos time domain," FEBS Lett., pp. 103-106. (Abstract).
de Wijn et al. (2001), "Secondary stabilization reactions and proton-coupled electron transport in photosytem II investigated by electroluminescence and fluorescence spectroscopy," Biochemistry, pp. 5821-5834.
Hou et al. (2001), "Thermodynamics of electron transfer in oxygenic photosystem reaction centers; a pulsed photoacoustic study of electron transfer in photosystem I reveals a similarity to bacertial reaction centers in both volume change and entropy," Biochemistry, pp. 7109-7016.
Response to Office Action dated Jun. 2, 2006 for Canadian Patent Application No. 2452408.
Office Action dated Mar. 2, 2007 for Canadian Patent Application No. 2452408.
Response to Office Action dated Mar. 2, 2007 for Canadian Patent Application No. 2452408.
Office Action dated Jan. 31, 2008 for Canadian Patent Application No. 2452408.
Response to Office Action dated Jan. 31, 2008 for Canadian Patent Application No. 2452408.
Office Action dated Nov. 10, 2008 for Korean Patent Application No. 7017182/2003.
First Statement of Proposed Amendments dated Feb. 17, 2006 for Australian Patent Application No. 2003220671.
Notices for Reasons of Rejection dated Mar. 26, 2008 for Japanese Patent Application 2003-508231.
Amendment to Notices for Reasons of Rejections dated Mar. 26, 2008 for Japanese Patent Application No. 2003-508231.
Response to Second Office Action dated May 23, 2008 for Chinese Patent Application No. 03813556.6.
Examination Report dated Feb. 22, 2008 for New Zealand Patent Application No. 530600.
Response to Examination Report dated Feb. 22, 2008 for New Zealand Patent Application No. 530600.
Examination Report dated Aug. 20, 2008 for New Zealand Patent Application No. 530600.
Second Official Letter dated Jul. 27, 2007 for Mexican Patent Application No. 2004/000187.
Response to Second Official Letter dated Jul. 27, 2007 for Mexican Patent Application No. 2004/000187.
Third Official Letter dated Jan. 3, 2008 for Mexican Patent Application No. 20041/000187.
Response to Third Official Letter dated Jan. 3, 2008 for Mexican Patent Application No. 2004/000187.
First Office Action dated Dec. 12, 2008 for Indian Patent Application No. 1590/KOLNP/2004.

(56) References Cited

OTHER PUBLICATIONS

Withdrawal Petition dated Nov. 20, 2009 for Indian Patent Application No. 1590/KOLNP/2004.
Official Letter dated Mar. 21, 2008 for Chinese Patent Application No. 02816794.5.
Response to Official Letter dated Mar. 21, 2008 for Chinese Patent Application No. 02816794.5.
Official Letter dated Jul. 22, 2009 regarding Second Office Action for Chinese Patent Application No. 02816794.5.
Response to Official Letter dated Jul. 22, 2009 regarding Second Office Action for Chinese Patent Application No. 02816794.5.
Official Letter dated Jan. 5, 2010 regarding Third Office Action for Chinese Patent Application No. 02816794.5.
Response to Official Letter dated Jan. 5, 2010 regarding Third Office Action for Chinese Patent Application 02816794.5.
Rejection Decision dated Oct. 30, 2009 for Chinese Patent Application No. 03813556.6.
Response to Rejection Decision dated Oct. 30, 2009 for Chinese Patent Application No. 03813556.6.
Examiner's First Report dated Oct. 4, 2007 for Australian Patent Application No. 2003220671.
Voluntary Amendment dated Apr. 25, 2007 for Canadian Patent Application No. 2482934.
Office Action dated Jun. 15, 2007 for Canadian Patent Application No. 2482934.
Response to Office Action dated Jun. 15, 2007 for Canadian Patent Application No. 2482934.
Office Action dated Feb. 21, 2008 for Canadian Patent Application No. 2482934.
Response to Office Action dated Feb. 21, 2008 for Canadian Patent Application No. 2482934.
Office Action dated Oct. 17, 2008 for Canadian Patent Application No. 2482934.
Response to Office Action dated Oct. 17, 2008 for Canadian Patent Application No. 2482934.
Office Action dated Jun. 3, 2010 for Canadian Patent Application No. 2482934.
Response to Office Action dated Jun. 3, 2010 for Canadian Patent Application No. 2482934.
Office Action dated Feb. 1, 2011 for Canadian Patent Application No. 2482934.
First Office Action dated Mar. 10, 2006 for Chinese Patent Application No. 03813556.6.
Response to First Office Action dated Mar. 10, 2006 for Chinese Patent Application No. 03813556.6.
Second Office Action dated May 23, 2008 for Chinese Patent Application No. 03813556.6.
Response to Office Action dated Jul. 2, 2007 for European Patent Application No. 02792232.7.
Office Action dated Jun. 22, 2009 for European Patent Application No. 02792232.7.
Response to Office Action dated Jun. 22, 2009 for European Patent Application No. 02792232.7.
Office Action dated Oct. 18, 2010 for European Patent Application No. 02792232.7.
Response to Office Action dated Oct. 18, 2010 for European Patent Application No. 02792232.7.
First Examination Report dated Jul. 12, 2007 for Indian Patent Application No. 620/KOLNP/2004.
Office Action dated Feb. 14, 2008 for Israeli Patent Application No. 161865.
Response to Office Action dated Feb. 14, 2008 for Israeli Patent Application No. 161865.
Office Action dated Sep. 15, 2010 for Israeli Patent Application No. 161865.
Response to Office Action dated Sep. 15, 2010 for Israeli Patent Application No. 161865.
Office Action dated May 14, 2008 for Japanese Patent Application No. 2003-541770.
Report of Final Decision of Refusal dated Feb. 2, 2009 for Japanese Patent Application No. 2003-541770.
Office Action dated Oct. 10, 2012 for European Patent Application No. 02792232.7.
Office Action dated Sep. 23, 2009 for Korean Patent Application No. 7007060/2004.
Response to Office Action dated Sep. 23, 2009 for Korean Patent Application No. 7007060/2004.
Response to Office Action dated Jul. 27, 2010 for Korean Patent Application No. 7007060/2004.
Appeal Brief dated Oct. 26, 2010 for Korean Patent Application No. 7007060/2004.
Office Action dated Dec. 9, 2010 for Korean Patent Application No. 7007060/2004.
Response to Office Action dated Dec. 9, 2010 for Korean Patent Application No. 7007060/2004.
Office Action dated Jan. 17, 2012 for Korean Patent Application No. 70007060/2004.
Official Letter dated May 21, 2008 for Mexican Patent Application No. 2004/004463.
Response to Official Letter dated May 21, 2008 for Mexican Patent Application No. 2004/004463.
Examination Report dated Mar. 13, 2006 for New Zealand Patent Application No. 533303.
Search Report dated May 22, 2008 for PCT Patent Application No. PCT/US07/02958.
Search Report dated May 27, 2008 for PCT Patent Application No. PCT/US07/05288.
Search Report dated Mar. 2, 2008 for PCT Patent Application No. PCT/US07/05288.
Examiner's first report dated Aug. 5, 2010 for Australian Patent Application No. 2007212519.
Office Action dated Feb. 22, 2012 for Japanese Patent Application No. 2008-553383.
Response to Office Action dated Feb. 22, 2012 for Japanese Patent Application No. 2008-553383.
Office Action dated Aug. 26, 2011 for European Patent Application No. 07763561.3.
Voluntary Amendment dated Dec. 4, 2008 for European Patent Application No. 07763561.3.
Search Report and Opinion dated Apr. 23, 2009 for European Patent Application No. 07763561.3.
First Examination Report dated Aug. 19, 2009 for European Patent Application No. 07763561.3.
Response to First Examination Report dated Aug. 19, 2009 for European Patent Application No. 7763561.3.
Response to Office Action dated Mar. 21, 2012 for Japanese Patent Application No. 2008-557382.
Office Action dated Mar. 21, 2012 for Japanese Patent Application No. 2008-557382.
Invitation to Correct Defects dated Jul. 22, 2002 for PCT Patent Application No. PCT/US02/20706.
Response to Invitation to Correct defects dated Jul. 22, 2002 for PCT Patent Application No. PCT/US02/20706.
Written Opinion dated Jul. 31, 2003 for PCT Patent Application No. PCT/US02/20706.
Response to Written Opinion dated Jul. 31, 2003 for PCT Patent Application No. PCT/US02/20706.
Preliminary Examination Report dated Oct. 27, 2005 for PCT Patent Application No. PCT/US02/20706.
International Search Report dated Aug. 11, 2003 for PCT Patent Application No. PCT/US03/10509.
Preliminary Examination Report dated Jun. 17, 2004 for PCT Patent Application No. PCT/US03/10509.
Official Action dated Jul. 28, 2010 for Israeli Patent Application No. 159579.
Official Action dated Sep. 8, 2008 for Israeli Patent Application No. 159579.
Response to Official Action dated Sep. 8, 2008 for Israeli Patent Application No. 159579.
Voluntary Amendment dated Apr. 19, 2006 for Canadian Patent Application No. 2452408.

(56) References Cited

OTHER PUBLICATIONS

Office Action dated Jun. 2, 2006 for Canadian Patent Application No. 2452408.
Result of Consultation by Telephone with Applicant/Representative dated Aug. 28, 2008 for European Patent Application No. 027614494-1216.
Decision to Refuse a European Application dated Mar. 31, 2009 for European Patent Application No. 02761449.4-1216.
Office Action dated May 13, 2008 for Israeli Patent Application No. 160505.
Response to Office Action dated May 13, 2008 for Israeli Patent Application No. 160505.
Office Action dated Mar. 1, 2007 for Indian Patent Application No. 00332/KOLNP/2004.
Response to Office Action dated Mar. 1, 2007 for Indian Patent Application No. 00332/KOLNP/2004.
Office Action dated Nov. 10, 2008 for Korean Patent Application No. 7002677/2004.
Office Action dated Feb. 22, 2012 for Japanese Patent Application No. 2009-236857.
Office Action dated Sep. 12, 2012 for Japanese Patent Application No. 2009-236857.
Response to Office Action dated Sep. 12, 2012 for Japanese Patent Application No. 2009-236857.
Official Letter dated Sep. 3, 2007 for Mexican Patent Application No. 2004/001710.
2nd Official Action dated Sep. 19, 2008 for Mexican Patent Application No. 2004/001710.
3rd Official Action dated Dec. 8, 2010 for Mexican Patent Application No. 2004/001710.
Response to 3rd Official Action dated Dec. 8, 2010 for Mexican Patent Application No. 2004/001710.
Examination Report dated Apr. 28, 2005 for New Zealand Patent Application No. 531491.
First Statement of Proposed Amendments dated Dec. 21, 2005 for Australian Patent Application No. 2002357695.
Official Report dated Jun. 28, 2007 for Australian Patent Application No. 2002357695.
Response to Official Report dated Jun. 28, 2007 for Australian Patent Application No. 2002357695.
Official Report dated Dec. 19, 2007 for Australian Patent Application No. 2002357695.
Office Action dated Aug. 9, 2006 for Canadian Patent Application No. 2465906.
Response to Office Action dated Aug. 9, 2006 for Canadian Patent Application No. 2465906.
Office Action dated Mar. 27, 2007 for Canadian Patent Application No. 2465906.
Response and Amendment to Office Action dated Mar. 27, 2007 for Canadian Patent Application No. 2465906.
Office Action dated Nov. 23, 2007 for Canadian Patent Application No. 2465906.
Response to Office Action dated Nov. 23, 2007 for Canadian Patent Application No. 2465906.
Office Action dated Oct. 5, 2010 for Canadian Patent Application No. 2465906.
Response to Office Action dated Oct. 5, 2010 for Canadian Patent Application No. 2465906.
Office Action dated Jun. 30, 2011 for Canadian Patent Application No. 2465906.
Response to Office Action dated Jun. 30, 2011 for Canadian Patent Application No. 2465906.
Office Action dated Mar. 3, 2010 for Canadian Patent Application No. 2465906.
Response to Office Action dated Mar. 3, 2010 for Canadian Patent Application No. 2465906.
Office Action dated Oct. 14, 2005 for Canadian Patent Application No. 028247698.
Second Office Action dated Apr. 11, 2008 for Chinese Patent Application No. 028247698.
Response to Second Office Action dated Apr. 11, 2008 for Chinese Patent Application No. 028247698.
Third Office Action dated Aug. 15, 2008 for Chinese Patent Application No. 028247698.
Office Action dated Sep. 11, 2006 for European Patent Application No. 02792232.7.
Response to Office Action dated Sep. 11, 2006 for European Patent Application No. 02792232.7.
Office Action dated Jul. 2, 2007 for European Patent Application No. 02792232.7.
Office Action dated Feb. 29, 2012 for Japanese Patent Application No. 2003-522355.
Response to Official Report dated Dec. 19, 2007 for Australian Patent Application No. 2002357695.
Office Action dated May 16, 2010 for Israeli Patent Application No. 160505.
Response to Office Action dated May 16, 2010 for Israeli Patent Application No. 160505.
Response to Office Action dated Oct. 14, 2005 for Chinese Patent Application No. 028247698.
Kemmatp, et al. (May 2001), "What Color is my LED?" Photonics Spectra.
Laakso, et al. (1997), "Pain Scores and Side Effects in Response to Low Level Laser Therapy (LLLT) for Myofascial Trigger Points", Laser Therapy 9:67-72.
Labbe et al., (1990), "Laser Phobioactivation Mechanisms: In Vitro Studies Using Ascorbic Acid Uptake and Hydroxyproline Formation as Biochemical Markers of Irradiation Response", Lasers in Surgery and Medicine 10, pp. 201-207.
Liberman et al. (1996), "Light Years Ahead", pp. 277-283.
Lieb, Linda, et al. (1992), "Topical Delivery Enhancement with Multilamellar Liposomes into Pilosebaceous Units: I. In Vitro Evaluation Using Fluorescent Techniques with the Hamster Ear Model", The Journal of Investigative Dermatology 99(1).
Li, Lingna, et al. (1992), "Product-Delivering Liposomes Specifically Target Hair Follicles in Histocultured Intact Skin", In Vitro Cell Dev. Biol. 281, pp. 679-681.
Liu et al. (2002), "Inhibition of AP-1 Transcription Factor Causes Blockade of Multiple Signal Transduction Pathways and Inhibits Breast Cancer Growth", Oncogene 21:7680-7689.
Loevschall, (1994), "Effect of Low Level Diode Laser Irradiation of Human Oral Mucosa Fibroblasts In Vitro", Lasers in Surgery and Medicine 14, pp. 347-354.
Logdberg-Anderson et al. (1997), "Low Level Laser Therapy (LLLT) of Tendonitis and Myofascial Pains: a Randomized, Double-blind, Controlled Study", Laser Therapy 9:79-86.
Kloth, Luther, et al. (1996), "Promotion of Wound Healing with Electrical Stimulation", The Journal for Prevention and Healing Advances 9(5).
Coldman, M.F., et al. (1969), "Enhancement of Percutaneous Absorption by the Use of Volatile: Nonvolatile Systems as Vehicles", Journal of Pharmaceutical Sciences vol. 58, #9.
Hrnjak, M., et al. (Nov. 1995), "Stimulatory Effect of Low-Power Density He-Ne Laser Radiation on Human Fibroblast in . Vitro", Vojnosanit Pregl. 52(6), pp. 539-546.
Callam, M. J., et al. (Jul. 1987) ,"A Controlled Trial of Weekly Ultrasound Therapy in Chronic Leg Ulceration", the Lancet, pp. 204-206.
Pogrel, M., et al. (1997) ,"Effects of Low-Energy Gallium-Aluminum-Arsenide Laser Irradiation on Cultured Fibroblasts and Keratincytes", Lasers in Surgery and Medicine 20, pp. 426-432.
Suzuki, M., et al. (1978), "Autoradiographic Study on Percutaneous Absorption of Several Oils Useful for Cosmetics", J. Soc. Cosmet Chem. 29, pp. 265-282.
Weiner, M., et al. (1994), "Liposomes: a Novel Topical Delivery System for Pharmaceutical and Cosmetic Applications", Journal of Drug Targeting 2, pp. 405-410.
Dyson, Mary (Sep. 1982), "Stimulation of Tissue Repair by Therapeutic Ultrasound", Infections in Surgery 1(2), Pp. 37-44.
Dyson, Mary, et al. (Apr. 1978), "Stimulation of Tissue Repair by Ultrasound: A Survey of the Mechanisms Involved", Physiotherapy 64(4), pp. 105-108.

(56) References Cited

OTHER PUBLICATIONS

McDaniel (May 2001), "Nonablative Skin Rejuvenation-The Wave of the Future", Cosmetic Surgery Times.

McDaniel, D. H., et al. (1996), "Treatment of Stretch Marks With the 585-nm Flashlamp-Pumped Pulsed Dye Laser", Dermatological 22(4), pp. 332-337.

Menezes et al. (Oct. 1998), "Non-Coherent Near Infrared Radiation Protects Normal Human Dermal Fibroblasts from Solar Ultraviolet Toxicity", The Journal of Investigative Dermatology 111(4):629-633.

Monfrecola, G., et al (1987), "Topical Hematoporphyrin Plus Uva for Treatment of Alopecia Areata", Photodermatology 4:305-306.

Lehman, P. et al. (1991), "Effects of Ultraviolet A and B on the Skin Barrier: A Functional Electron Microscopic and Lipid Biochemical Study", Photodermatol Photoimmunol Photomed. 8, pp. 129-134.

Morganti, P., et al. (1997), "Enhancing the Glycolic Acid Efficacy by Piezoelectric Vibrations," J. Appl. Cosmotol. vol. 15, pp. 147-159.

Singh, Parminder, et al. (1993), "Iotophoretic Transdermal Delivery of Salicylic Acid and Lidocaine to Local Subcutaneous Structures", Journal of Pharmaceutical Sciences 82(2), pp. 127-131.

Parrish et al. (1981), "Action Spectrum for Phototherapy of Psoriasis," Journal of Investigative Dermatology 76 (5):359-362.

De Deyne, Patrick G., et al. (711995), "In Vitro Effects of Therapeutic Ultrasound on the Nucleus of Human Fibroblasts", Physical Therapy 75(7), pp. 629-634.

Scheuplein, Robert, et al. (1971), "Permeability of the Skin", Physiological Review, vol. 51, No. 4.

Polo, et al. (1999), "Role of Ground and Excited Singlet State Ozygen in the Red Light-Induced Stimulation of *Escherichia coli* Cell Growth", Biochemical and Biophysical Research Communications 257, pp. 753-758.

Potinen et al. (1996), "Comparative Effects of Exposure to Different Light Sources (He-Ne Laser, InGaAl Diode Laser, A Specific Type of Noncoherent LED) On Skin Blood Flow for the Head", Res. Int. J., vol. 21, pp. 105-118.

Brucks, Richard, et al. (1989), "The Effect of Ultrasound on the In Vitro Penetration of Ibuprofen Through Human Epidermis", Pharmaceutical Research 6(8), pp. 697-701.

Borelli, S. (1955), "Chlorophyll in the Treatment 1-27 of Acne Vulgaris", Dematologie, Venerologie, and Verwandte Gebiete 6(7), pp. 320-324.

Mordon, S., et al (1997), "Thermal Damage Assessment of Blood Vessels in a Hamster Skin Flap Model by Fluorescence Measurement of a Liposome-Dye System", Lasers in Surg. & Med. 20, pp. 131-141.

Mordon, S., et al. (1997), "Selective Laser Photocoagulation of Blood Vessets in a Hamater Skin Flip Model using a Specific ICG Formulation", Lasers Surg. Med. 21(4), pp. 365-373.

Sakurai et al. (2000), "Inhibitory effect of low-level laser irradiation on LPS-stimulated prostaglandin E2 production and cyclooxygnase-2 in human gingival fibroblasts", in Er. J. Oral. Sci., Issue 108:pp. 29-34.

Schindl et al. (Sep. 2000), "Low-Intensity Laser Therapy: A Review", Journal of Investigative Medicine, 48(5).

Schul et al. (2002), "Enhanced repair of cyclobutane pyrimidine dimers and improved UV resistance in photolyase transgenic mice", The European Molecular Biology Organization (EMBO) Journal 21(17):4719-4729.

ScienceDaily "2002 Nobel Price in Physiology Or Medicine: Programmed Cell Death," dated Oct. 8, 2002, located at http://www.sciencedaily.com/releases/2002/10/021008064740.htm Retrieved on Oct. 24, 2007. (5 pages).

Shalita et al., (2001), "Acne PhotoClearing (APC) Using a Novel, High-Intensity, Enhanced, Narrow-Band, Blue Light Source", Clinical Application Notes 9(1).

Pinnell, Sheldon (1985), "Regulation of Collagen Biosynthesis of Ascorbic Acid: A Review" The Yale Journal of Biology and Medicine 58, pp. 553-559.

Tajima, Shingo, et al. (1996) "Ascorbic Acid Preferentially Enhances Type I and III Collagen Gene Transcription in Human Skin Fibroblasts", J. Dermatol. Sci. 11(3), pp. 250-253.

Skinner et al., (1996), "A Preliminary Study of the Effects of Laser Radiation on Collagen Metabolism in Cell Culture", Australian Dental Journal 41(3), pp. 188-192.

Sommer et al. (2001), "Biostimulatory Windows in Low-Intensity Laser Activation: Lasers, Scanners and NASA's Light Emitting Diode Array System", Journal of Clinical Laser Medicine & Surgery 19(1), pp. 29-33.

Sroka et al. (1999), "Effects on the Mitosis of Normal and Tumor Cells Induced by Light Treatment of Different Wavelengths", Lasers in Surgery and Medicine 25, pp. 263-271.

Melo, T. B. (1987), "Uptake of Protoporphyrin and Violet Light Photodestruction of Propionibacterium acnes", Journal of Biosciences 42(1-2), pp. 123-128.

Phillips, Charlotte, et al. (1994), "Effects of Ascorbic Acid on Profileration and Collagen Synthesis in Relation to the Donor Age of Human Dermal Fibroblasts", The Journal of Investigative Dermatology, vol. 103, No. 2.

Srinivasan, V., et al. (1989), "Transdermal Iontophoretic Drug Delivery: Mechanistic Analysis and Application to Polypeptide Delivery", Journal of Pharmaceutical Sciences 78(5).

Srinivasan, V., et al. (1990), "Ionotphoresis of Polypeptides: Effect of Ethanol Pretreatment of Human Skin", Journal of Pharmaceutical Sciences 79(7), pp. 588-591.

Van Breugel et al. (1992), "Power Density and Exposure Time of He-Ne Laser Irradiation are More Important than Total Energy Dose in Photo-Biomodulation of Human Fibroblasts in Vitro", Lasers in Surgery and Medicine 12, pp. 528-537.

Vreman et al. (Nov. 1998), "Light-Emitting Diodes: A Novel Light Source for Phototherapy", vol. 44, Issue 5, pp. 804-809.

Vuillaume, et al. (2001), "Real Time RT-PCR Shows Correlation between Retinoid-Induced Apoptosis and NGF-R mRNA Levels", Biochemical and Biophysical Research Communications 289(3):647-652.

Harvey, W., et al. (1975), "The Stimulation of Protein Synthesis in Human Fibroblasts by Therapeutic Ultrasound," Rheumatology and Rehabilitation 14, 237.

Yu, W., et al. (1997), "Effects of Photostimulation on Wound Healing in Diabetic Mice", Lasers in Surgery and Medicine, 20(1), pp. 56-63.

Webb, et al., (1998), "Stimulatory Effect of 660 nm Low Level Laser Energy on Hypertrophic Scar-derived Fibroblasts: Possible Mechanisms for Increase in Cell Counts", Lasers in Surgery and Medicine 22, pp. 294-301.

Yu, Wei, et al. (1997), "Improvement of Host Response to Sepsis by Photobiomodulation", Lasers in Surgery and Medicine 21, pp. 262-268.

Wei, Li-Na (2004), "Retinoids and Receptor Interacting Protein 140 (RIP140) in Gene Regulation", Current Medicinal Chemistry 11(12):1527-1532.

Westerhof et al., "Treatment of Vitiligo with UV-B Radiation vs Topical Psoralen Plus UV-A", Arch Dermatol, vol. 133, Dec. 1997, pp. 1525-1528.

Whelan et al., "NASA Light Emitting Diode Medical Applications From Deep Space to Deep Sea", CP552, Space Technology and Applications International Forum 2001, p. 35-45.

Ritschel, Wolfgang, et al. (1989), "Percutaneous Absorption of Coumarin, Griseofulvin and Propranolol Across Human Scalp and Abdominal Skin", Meth and Find Exp. Clin. Pharmacol. 11(10), pp. 643-646.

Joachims, Z. et al. (1987), "Noise-Induced Hearing Loss in Humans as a Function of Serum Mg Concentration", Magnesium Bulletin No. 3, pp. 130-131.

Zelickson, et al. (1999), "Pulsed Dye Laser Therapy for Sun Damaged Skin", Lasers in Surgery and Medicine 25, pp. 229-236.

Goldman, Erik L. (Oct. 1999), "FotoFacial is a Pulsed Light Patient Pleaser", Skin and Allergy News, p. 34.

Newman Joseph T., et al. (Aug. 1992), "Hydrocortisone Phonophoresis, A Literature Review", Journal of the American Podiatric Medical Association, vol. 82, No. 8, 432-435.

Mitragotri, Samir, et al. (Aug. 11, 1995), "Ultrasound-Mediated Transdermal Protein Delivery", Science, vol. 269, pp. 850-852.

(56) References Cited

OTHER PUBLICATIONS

Office Action dated Jun. 20, 2013 for U.S. Appl. No. 12/583,578.
Final Office Action dated Jun. 14, 2007 for U.S. Appl. No. 10/903,483.
European Office Action dated Jul. 21, 2008, directed to EP Application No. 02761449.4.
European Search Report dated Sep. 16, 2005, directed to EP Application No. 02761449.4.
Third-Party Observations dated Sep. 12, 2007, directed to EP Application No. 02749720.5.
International Preliminary Examination Report dated Aug. 6, 2004 directed toward Patent Application PCT/US02/26627.
Office Action dated Feb. 25, 2013 directed towards Japanese Patent Application 2008-553383.
Office Action dated Feb. 6, 2013 directed towards Japanese Patent Application 2008-557382.
Office Action dated May 16, 2013 directed towards European Patent Application No. 04779826.9.
Search Report dated Sep. 16, 2005 directed towards European Patent Application 02761449.4.
Office Action dated Nov. 16, 2012 directed towards Chinese Patent Application 201110210275.4.
Search Report dated Oct. 6, 2010 directed towards European Patent Application 07752016.1.
Application to Amend a Complete Specification dated Jul. 24, 2012 directed towards South African Patent Application 2004/1528.
Yano, K., Lawrence, B.F., & Detmar, M. (2001). "Control of hair growth and follicle size by VEGF-mediated angiogensis." The Journal of Clinical Investigation, 107(4), pp. 409-417.
Wei, Y.H., et al. (2001). "Mitochondrial theory of aging matures—Roles of mtDNA mutuation and oxidative stress in human aging." Chinese Medical Journal, 64, pp. 259-270.
Hoffman, J.W., et al (2004). "Myocardial reperfusion injury: Etiology, mechanisms, and therapies." The Journal of the American Society of Extra-Corporeal Technology, 36, pp. 391-411.
Chwirot, W.B. (1986). "New indications of possible role of DNA in ultraweak photon emission from biological systems." Journal of Plant Physiology, 122, pp. 81-86.
Albrecht-Buehler, G. (1994). "Cellular infrared detector appears to be contained in the centrosome." Cell Motility and the Cytoskeleton 27, pp. 262-271.
Kiang, J.G. (2004). "Inducible heat shock protein 70kD and inducible nitric oxide synthase in hemorrhage/resuscitation-induced injury." Cell Research, 14(6), pp. 450-459.
Yu, W., et al (1997). "Improvement of host response to sepsis by photobiomodulatio." Lasers in Surgery and Medicine, 21(3), pp. 262-268.
Byrnes, K.R., et al. (2004). "Photobiomodulation improves cutaneous wound healing in an animal model of type II diabetes." Photomedicine and Laser Surgery, 22(4), pp. 281-290.
Byrnes, K.R., et al. (2005). "Light promotes regeneration and functional recovery and alters the immune response after spinal cord injury." Lasers in Surgery and Medicine, Feb. 9, (online).
Wong-Riley, M.T., et al. (2005). "Photobiomodulation directly benefits primary neurons functionally inactive by toxins: role of cytochrome c oxidase." Journal of Biological Chemistry, 280(6), pp. 4761-4771.
El Hindi, T., et al. (2004). "Determination of the antioxidant capacity of an antioxidant combination using the fluoroscan assay in vitro and visualization of its effects using histological methods." Archives of Dermatological Research, 296(6), pp. 258-264.
Elmets, C.A., Vargas, A., & Oresajo, C. (1992). "Photoprotective effects of sunscreens in cosmetics on sunburn and Langerhans cell photodamage." Photodermatology, Photoimmunology, and Photomedicine, 9(3), pp. 113-120.
Stein, R. (2005). "Fat found to accelerate aging process." Washington Post, Jun. 14, 2005.

Block, G., et al. (2004). "Plasma-C reactive protein concentrations in active and passive smokers: influence of antioxidant supplementation." Journal of the American College of Nutrition, 23(2), pp. 141-147.
Noda, Y., et al. (2002). "Antioxidant activities of pomegranate fruit extract and its anthocyanindins: delphindin, cyaniding, and pelagronidin." Journal of Agricultural and Food Chemistry, 50(1), pp. 166-171.
Monaco, J.L. & Lawrence, W.T. (2003). "Acute wound healing an overview." Clinics in Plastic Surgery, 30, pp. 1-12.
Hinz, B., et al. (2001). "Apha-smooth muscle actin expression upregulates fibroblast contractile activity." Molecular Biology of the Cell, 12, pp. 2730-2741.
Azevedo, L.H., et al. (2005). "Evaluation of low intensity laser effects on the thyroid gland of male mice." Photomedicine and Laser Surgery, 23(6), pp. 567-570.
Tuby, H., Maltz, L., & Oron, U. (2006). "Modulations of VEGF and iNOS in the rat heart by low level laser therapy are associated with cardioprotection and enhanced angiogensis." Lasers in Surgery and Medicine, 38, pp. 682-688.
Fratelli, M., et al. (2005). "Gene expression in profiling reveals a signaling role of gluthathione in redox regulation." PNAS, 102(39), pp. 13998-14003.
Hymes, S.R., Strom, E.A., & Fife, C. (2006). "Radiation dermatitis: Clinical presentation, pathophysiology, and treatment 2006." Journal for the American Academy of Dermatology, 54, pp. 28-46.
Omura, Y. (2004). "Special sunrise & sunset solar energy stored papers and their clinical applications for intractable pain, circulatory disturbances & cancer: Comparison of Beneficial effects between special solar energy stored paper and quigong energy stored paper." Acupuncture & Electro-therapeutics, 29, pp. 1-42.
Stoica, E. & Enulescu, O. (1988). "Catecholamine response to light in migraine" Cephalalgia, 8, pp. 31-36.
Kowluru, R.A. (2005). "Diabetic retinopathy: mitochondrial dysfunction and retinal capillary cell death." Antioxidants & Redox Signaling, 7(11,12), pp. 1581-1587.
McDaniel, D., et al. (1998). "Body contouring: A preliminary report on the use of the silhouette® device for treating cellulite." Aesthetic Surgery Journal, 18(3), pp. 177-182.
Noton, D. (2000). "Migraine and photic stimulation: Report on a survey of migraineurs using flickering light therapy." Complementary Therapies in Nursing & Midwifery, 6, pp. 138-142.
Alstadhaug, K.B., Salvesen, R., & Bekkelund, S.I. (2005). "Seasonal variation in migraine." Cephalalgiai, 25, pp. 811-816.
Claustrat, B., et al. (2004). "Melatonin secretion is supersensitive to light in migraine." Cephalalgia, 24, pp. 128-133.
Passache, G., et al. (2000). "Mitochondria of retinal muller (glial) cells: The effects of aging and of application of free radical scavengers." Opthalmic Research, 32, pp. 229-236.
Liang, F.Q. & Godley, B.F. (2003). "Oxidative stress-induced mitochondrial DNA damage in human retinal pigment epithelial cells: A possible mechanism for RPE aging and age-related macular degeneration." Experimental Eye Research, 76, pp. 397-403.
Anderson, D.J., et al. (1997). "Preliminary trial of photic stimulation for premenstrual syndrome." Journal of Obstetrics and Gynaecology, 17(1), pp. 76-79.
Main, A., et al. (2000). "The wavelength of light causing photophobia in migraine and tension-type headache between attacks." Headache, 40, pp. 194-199.
Eells, J.T. et al. (2004). "Mitochondrial signal transduction in accelerated wound and retinal healing by near-infrared light therapy." Mitochondrion, 4, pp. 559-567.
"Thiol" From Wikipedia page: http://en.wikipedia.org/wiki/Thiol Accessed: May 6, 2007.
"Disulfide Bond" From Wikipedia page: http://en.wikipedia.org/wiki/Disulfide_bond Accessed: May 6, 2007.
"Permanent Wave" From Wikipedia page: http://en.wikipedia.org/wiki/Permanent_wave Accessed: May 6, 2007.
Martin, K. (2007). "Infrared and ramen studies of skin and hair: A review of cosmetic spectroscopy." The Internet Journal of Vibrational Spectroscopy, 3(2), online Accessed: Apr. 24, 2007.

(56) References Cited

OTHER PUBLICATIONS

Jarrousse, F., et al. (2001). "Identification of clustered cells in human hair follicle responsible for MMP-9 gelatinolytic activity: Consequences for the regulation of hair growth." International Journal of Dermatology, 40(6), pp. 385-392.
Langbein, et al. (2001). "Figure 8." Journal of Biological Chemistry, 276(37), pp. 35123.
King, A., et al. (2004). "Mitochondria-derived reactive oxygen species mediate blue light-induced death of retinal pigment epithelial cells." Photochemistry and Photobiology, 79(5), pp. 470-475.
"The EpiOcular™ Model." http://www.mattek.com/pages/products/epiocular. Mattek Corporation. Accessed: Apr. 27, 2005.
"Folliquanta® : A range of in vivo assays of hair follicle damage and alopecia." EpiStem® LTD. Copyright 2003 Epistem Ltd.
Davis, S.C., et al. (2004). "To examine the effect of GentleWaves LED photomodulation device on deep partial thickness wound healin." Preliminary Protocol: Deep Partial thickness wound study. Department of Dermatology and Cutaneous Surgery, University of Miami School of Medicine.
"Virulite CS® . . . The ORIGINAL Cold Sore Machine." http://www.virulite.com/technical_information.html Date accessed: Jan. 26, 2008.
Christensen, B. (2008). "Forced resonance ultra-short pulse laser kills viruses dead." Technovelogy.com Where Science Meets Fiction, http://www.technovelogy.com/ct/Science-Fiction-News.asp?NewsNum=1311. Date Accessed: Jan. 26, 2008.
"Visual Signal Transduction." Biocarta http://www.biocarta.com/pathfiles/h_rhodospinPathway.asp Date Accessed: Aug. 29, 2005.
Epstein, P. (2007). "Trials that matter: Two faces of progress in the treatment of age-related macular degeneration." Annals of Internal Medicine, 146(7), pp. 532-534.
Ostler, E.L. et al. (2000) "Telomerase and the cellular lifespan: Implications of the aging process." Journal of Pediatric Endocrinology and Metabolism, 13(6), pp. 1467-1476.
Lou, H. J. et al.(2002). "Lighting the way: Molecular beacons offer a highly sensitive, flexible method for DNA analysis." Spie's OEMagazine, Feb., pp. 23-25.
"The Relief Light: A sensible alternative to 'soft' laser technology." Retrieved: http://www.fredomunlimited.net/relief%20light.htm Date Accessed: Feb. 9, 2002.
Stern, R. et al. (2001)."Hyaluronidase can modulate expression of CD44." Experimental Cell Research, 265, pp. 1-10.
Mio, K. et al. (2000). "Evidence that the serum inhibitor of hyaluronidase may be a member of the inter-a-inhibitor family." Journal of Biological Chemistry, 275(42), pp. 32413-32421.
Mortimer, A.J., & Dyson, M. (1988). "The effect of therapeutic ultrasound on calcium uptake in fibroblasts." Ultrasound in Medicine and Biology, 14(6), pp. 499-506.
Official Action dated Oct. 25, 2006 for Canadian Patent Application No. 2531099.
First Office Action dated May 22, 2009 for Chinese Patent Application No. 200480021576.0.
Office Action dated Dec. 7, 2010 for Japanese Patent Application No. 2006-509834.
Response to Office Action dated Dec. 7, 2010 for Japanese Patent Application No. 2006-509834.
Office Action dated May 11, 2010 for Japanese Patent Application No. 2006-509834.
Response to Office Action dated May 11, 2010 for Japanese Patent Application No. 2006-509834.
Written Opinion of the International Search Authority dated Oct. 19, 2006 for PCT Patent Application No. PCT/US04/24879.
Office Action dated Feb. 28, 2012 for Canadian Patent Application No. 2533129.
Response to Office Action dated Feb. 28, 2012 for Canadian Patent Application No. 2533129.
Office Action dated Jun. 17, 2011 for European Patent Application No. 4779826.9.
Response to Office Action dated Jun. 17, 2011 for European Patent Application No. 4779826.9.
First Office Action dated Jul. 15, 2009 for European Patent Application No. 04779826.9.
Response to First Office Action dated Jul. 15, 2009 for European Patent Application No. 04779826.9.
Office Action dated May 31, 2010 for Israeli Patent Application No. 173123.
Response to Office Action dated May 31, 2010 for Israeli Patent Application No. 173123.
Office Action dated Apr. 7, 2010 for Japanese Patent Application No. 2006-522123.
Response to Office Action dated Apr. 7, 2010 for Japanese Patent Application No. 2006-522123.
Office Action dated Apr. 28, 2011 directed towards Korean Patent Application 10-2006-7002207.
Response to Office Action dated Apr. 28, 2011 for Korean Patent Application 10-2006-7002207.
Office Action dated Aug. 12, 2011 for Korean Patent Application 10-2006-7002207.
Response to Office Action dated Aug. 12, 2011 for Korean Patent Application 10-2006-7002207.
"Apoptosis," dated Sep. 19, 2005, located at http:www.neuro.wustl.edu/NEUROMUSCULAR/mother/apoptosis. htm> retrieved on Oct. 24, 2007 (5 pages).
"Chlorophyll," from Wikipedia located at http://de.wikipedia.org/wiki/Chlorophyll, visited on Jul. 18, 2007 (4 pages).
"Phorphin," from Wikipedia located at <en.wikipedia.org/wiki/Porphine, visited on Jul. 18, 2007 (2 pages).
Doukas, A. et al. (1996) "Physical Characteristics and Biological Effects of Laser-Induced Stress Waves", Ultrasound in Med. & Biol. 22(2), pp. 151-164.
Abergel et al., (Feb. 1987) "Biostimulation of Wound Healing by Lasers: Experimental Approaches in Animal Models and in Fibroblast Cultures", J. Dermatol. Surg. Oncol. 13/(2) pp. 127-133.
Drastichova, V. et al., (1973), "Strengthening of Sutured Skin Wound with Ultrasound in Experiments on Animals", Acta Chirurgiae Plasticae 15, pp. 114-119.
Guffey, Stephen et al., "More Than a Thermal Modality: Ultrasound", Advance Rehabilitation, Jul./Aug. 1994.
Rolland, Alain et al. (1993) "Site-Specific Drug Delivery to Pilosebaceous Structures Using Polymeric Microspheres", Pharmaceutical Research 10(12), pp. 1738-1744.
Enwemeka, Chukuka S. (Dec. 1989), "The Effects of Therapeutic Ultrasound on Tendon Healing", Am. J. Phys. Med. Rehabil., vol. 68 No. 6, pp. 283-287.
Tachibana, Katsuro et al. (Jun. 1993), "Use of Ultrasound to Enhance the Local Anesthetic Effect of Topically Applied Aqueous Lidocaine", Anesthesiology, V. 78 No. 6.
Lyons, R.F. et al. (Jan. 1987), "Biostimulation of Wound Healing in Vivo by a Helium-Neon Laser", Ann Plast Surg; 18 (1):47-50.
Wester, Ronald et al. (1980), "Variations in Percutaneous Absorption of Testosterone in Rhesus Monkey Due to Anatomic Site of Application and Frequency of Application", Arch Dermatol Res., 267, 229-235.
Franz, Thomas (Feb. 1985), "Percutaneous Absorption of Minoxidil in Man", Arch Dermatol, vol. 121.
Menon, Gopinathan K. et al. (Jan. 1991), "Ultrasound Localization of Calcium in Psoriatic and Normal Human Epidermis", Arch Dermatol, vol. 127.
Byl, Nancy N. et al. (Jul. 1992), "Low Dose Ultrasound Effects of Wound Healing: A Controlled Study with Yucatan Pigs", Arch Phys Med Rehabil., vol. 73.
Phillips, Charlotte, et al. (1992), "Ascorbic Acid and Transforming Growth Factor-B1 Increase Collagen Biosynthesis via Different Mechanisms: Coordinate Regulation of Proal(I) and Proal(III) Collagens", Archives of Biochemistry and Biophysics, vol. 295, No. 2, pp. 397-403.
Darr, Douglas, et al. (1993), "Ascorbic Acid and Collagen Synthesis: Rethinking a Role for Lipid Peroxidation", Archives of Biochemistry and Biophysics, vol. 307, No. 2, pp. 331-335.
Menezes, Salatiel, et al., (1998) "Non-Coherent Near Infrared Radiation Protects Normal Human Dermal Fibroblasts from Solar Ultraviolet Toxicity".

(56) References Cited

OTHER PUBLICATIONS

Morrone, G., et al. (Jul. 1998), "In Vitro Experimental Research of Rabbit Condrocytes Biostimulation with Diode Laser Ga-Al-As: a Preliminary Study", Artif Cells Blood Substit Immobil Biotechnol; 26(4):437-439 (Abstract).
Asawanonda et al. (May 2000), "308-nm Excimer Laser for the Treatment of Psoriasis", Arch Dermatol, vol. 136, pp. 619-624.
Krammer, B. et al. (Feb. 1993) "Photodynamic Effects on the Nuclear Envelope of Human Skin Fibroblasts", Journal of Photochem Photobiol. B: Biol. 17(2), pp. 109-114.
Bommannan et al. (1992) "Sonophoresis I. The Use of High Frequency Ultrasound to Enhance Transdermal Drug Delivery", Pharmaceutical Research 9(4), pp. 559-564.
Bommannan et al. (1992) "Sonophoresis II. Examination of the Mechanisms of Ultrasound-Enhanced Transdermal Drug Delivery", Pharmaceitcal Research 9(8), pp. 1043-1047.
Response to Office Action dated Jan. 17, 2012 for Korean Patent Application 7000706012004.
Response to Examiner's First Report dated Aug. 5, 2010 for Australian Patent Application 2007212519.
Office Action dated Feb. 29, 2012 for Japanese Patent Application 2008-553383.
Response to Office Action dated Feb. 29, 2012 for Japanese Patent Application 2008-553383.
Official Letter dated Nov. 17, 2006 for Mexican Patent Application 2004/000187.
Written Opinion of the International Search Authority dated Apr. 12, 2005 for Patent Application PCT/US04/10915.
Stables, G. I., et al. (1995), "Photodynamic Therapy", Cancer Treatment Reviews, vol. 21, pp. 311-323.
Katsumi, Toichiro A., et al. (1996), "Photodynamic Therapy With a Diode Laser for Implanted Fibrosarcoma in Mice Employing Mono-L-Aspartyl Chlorin E6", Photochemistry and Photobiology, 64(4), pp. 671-675.
J. Pospisilova et al. (1977) "Ultrasonic Effect on Collagen Synthesis and Deposition in Different Localized Experimental Granulomas," Acta Chirurgiae Plasticae 19, pp. 148-157.
Doan et al, (1999), "In Vitro Effects of Therapeutic Ultrasound on Cell Proliferation, Protein Synthesis, and Cytokin Production by Human Fibroblasts, Osteoblasts, and Monocytes" J. Oral Maxillofac Surg. 57, pp. 409-419.
Suzuki, M., et al. (May 1978), "Autoradiographic Study on Percutaneous Absorption of Several Oils Useful for Cosmetics", J. Soc, Cosmet. Chem., 29, 265-282.
Decision of Rejection dated Feb. 2, 2009 for Japanese Patent Application 2003-508231.
Preliminary Amendment filed Feb. 15, 2001 for U.S. Appl. No. 09/819,083.
Response to Official Notification dated Dec. 3, 2008 for Israeli Patent Application 171311.
Response to First Office Action dated Mar. 10, 2006 for Chinese Patent Application 200480012575.X.
Response to Second Office Action dated Nov. 2, 2007 for Chinese Patent Application 200480012575.X.
Decision of Rejection dated Dec. 1, 2008 for Japanese Patent Application 2003-522355.
Reply to Official Action for Mexican Patent Application 2004/001710.
Search Report dated Apr. 26, 2006 for European Patent Application 02792232.7.
Response to Office Action dated Oct. 18, 2010 for European Patent Application 02792232.7.
First Examination Report dated Feb. 8, 2007 for European patent application 02749720.
Response to First Examination Report dated Feb. 8, 2007 for European patent application 02749720.
Office Action dated Sep. 21, 2011 for Chinese Patent Application 03813556.6.
Response to Office Action dated Sep. 21, 2011 for Chinese Patent Application 03813556.6.
European Search Report dated Oct. 6, 2010 for European patent application 04759316.5.
Office Action dated Feb. 2, 2011 for European patent application 04759316.5.
Chen, Huxiong, et al. (1995) "Chemical Generation of Acoustic Waves: A Giant Photoacoustic Effect," Science 270.
Jean-Paul Ortonne (1989) "Psoralen Therapy In Vitiligo", Clinics in Dermatology, vol. 7, No. 2, Apr.-Jun.
Tsai, Jui-Chen, et al. (1992) "Drug and Vehicle Deposition from Topical Applications: Use of Vitro Mass Balance Technique with Minoxidil Solutions", Journal of Pharmaceutical Sciences, vol. 81, No. 8.
De Bie, R., et al. (1998). "Low-level laser therapy in ankle sprains: A randomized clinical trial," Archives of Physical Medication and Rehabilitation, 79, pp. 1415-1420.
Kostenyuk, I., Oh, B.J., & So, S. (1999). "Induction of early flowering in cymbidium niveo-marginatum mak in vitro." Plant Cell Reports, 19(1) (abstract).
Schindl, A, et al (1999) "Diabetic neuropathic foot ulcer: Successful treatment by low-intensity laser therapy." Dermatology, 198(3), pp. 314-316.
Schindl, A., et al. (1999) "Increased dermal angiogensis after low-intensity laser therapy for a chronic radiation ulcer determined by a video measuring system." Journal of the American Academy of Dermatology, 40(3), pp. 481-484.
Schindl, A., et al. (1999) "Low-intensity laser therapy is an effective treatment for recurrent herpes simplex infection. Results from a randomized double-blind placebo-controlled study." Journal of Investigative Dermatology, 113(2), pp. 221-223.
Schindl, A., et al. (1997) "Successful treatment of a persistent radiation ulcer by low power laser therapy," Journal of the American Academy of Dermatology, 37(4), pp. 646-648.
Schindl, M., et al. (1999) "Induction of complete wound healing in recalcitrant ulcers by low-intensity laser irradiation depends on ulcer cause and size." Photodermatology, Photoimmunology, and Photomedicine, 15(1), pp. 18-21.
Zugaro, A., et al. (1992) "Applicazione del laser infrarosso a colture in vitro di fibroblasti: efftii del parametro tempo di esposizione." Annali Italiani di Chirurgia, 63(2), pp. 193-195.
Newman, J.T., Nellermoe. M.D., & Carnett, J.L. (1992). "Hydrocortisone phonophoresis: A literature review," Journal of the American Podiatric Medical Association, 82(8). pp. 432-435.
Menon, G.K., Bommannan, D.B., & Elias, P.M. (1993). "High-frequency sonophoresis: Permeation pathways and structural basis for enhanced permeability," Skin Pharmacol, 7. pp. 130-139.
Mitragotri, S., Blankschtein, D., & Langer, R. (1995). "Ultrasound-mediated transdermal protein delivery," Science, 269. pp. 850-853.
Draper, D.O., Castel, J.C., & Castel, D. (1995). "Rate of temperature increase in human muscle during 1 MHz and 3 MHz continuous ultrasound," JOSPT, 22(4). pp. 142-150.
Rougier, A., et al. (1983). "In vivo correlation between stratum corneum reservoir function and percutaneous absorption," The Journal of Investigative Dermatology, 81. pp. 275-278.
Zabel, K. (1999). "Wrinkle removal without the wound," Dermatology Times, 20(6).
Zabel, K. (1999). "Future of laser surgery: Unexplored benefits await," Dermatology Times, 20(6).
Gniadecka, M., et al. (1994). "Ultrasound structure and digital image analysis of the subepidermal low echogenic band in aged human skin: Diurnal changes and interindividual variability," The Journal for Investigative Dermatology, 102(3), pp. 362-365.
Mitragotri, S., et al. (1995). "A mechanistic study of ultrasonically-enhanced transdermal drug delivery," Journal of Pharmaceutical Science; 84(6). pp, 697-706.
Meidan. V.M., et al. (1998). "Low intensity ultrasound as a probe to elucidate the relative follicular contribution to total transdermal absorption," Pharmaceutical Research, 15(1), pp. 85-92.
Mitragotri, S., Blankschtein, D., & Langer, R. (1996), "Transgermal drug delivery using low-frequency sonophoresis," Pharmaceutical Research, 13(3), pp. 411-420.

(56) References Cited

OTHER PUBLICATIONS

Mitragotn, S., Blankschtein, D., & Langer, R. (1986). "An explanation for the variation of the sonophoretic transdermal transport enhancement from drug to drug," Journal of Pharmaceutical Science, 86(10). pp. 1190-1192.

Hippius, M., et al. (1998). "In vitro investigations of drug release and penetration—enhancing effect of ultrasound on transmembrane transport of flufenamic acid," International Journal of Clinical Pharmacological, Therapy, and Toxicology, 36(2). pp. 107-111.

Miyazaki, S., et al. (1992). "External control of drug release and penetration. VI. enhancing effect of ultrasound on the transdermal absorption of indomethacin from an ointment in rats," Chemical and Pharmaceutical Bulletin, 40(10). pp. 2826-2830.

Asano, J., et al. (1997). "Effect of pulsed output ultrasound on the transdermal absorption of indomethacin from an ointment in rats," Biological and Pharmaceutical Bulletin, 20(3). pp. 288-291.

Miyazaki, S., et al. (1991). "External control of drug release and penetration: Enhancement of the transdermal absorption of indomethacin by ultrasound irradiation," Journal of Pharmaceutical Pharmacology, 43(2). pp. 115-116.

Bommannan, D., et al. (1992). "Sonophoresis.I. The use of high-frequency ultrasound to enhance transdermal drug delivery," Pharmaceutical Research, 9(4). pp. 559-564.

Tachibana, K., Tachibana, S. (1998). "Application of ultrasound energy as a new drug delivery system," Nippon Rinsho, 56(3). pp. 584-588.

Byl, N.N. (1995). "The use of ultrasound as an enhancer for transcutaneous drug delivery: phonophoresis," Physical Therapy, 75(6). pp. 539-553.

Hikima, T., Hirai, Y., & Tojo, K. (1998). "Effect of ultrasound application on skin metabolism of prednisolone 21-acetate," Pharmaceutical Research, 15(11). pp. 1680-1683.

Yata, N. (1998). "Enhancement of drug absorption by iontophoresis and phonophoresis and clinical application," Nippon Rinsho, 56(3). pp. 608-612.

Kimura, I.F., et al, (1998), "Effects of two ultrasound devices and angles of application on the temperature of tissue phantom," Journal of Orthopedic and Sports Physical Therapy, 27(1). pp. 27-31.

Mikulak, S.A., Vangsness, C.T., & Nimmi, M.E. (1998). "Transdermal delivery and accumulation of indomethacin in subcutaneous tissues in rats," Journal of Pharmaceutical Pharmacology, 50(2). pp. 153-158.

Murakami, T., et al. (1998). "Topical delivery of keloid therapeu c drug, trailast, by combined use of oleic acid and propylene glycol as a penetration enhancer: Evaluation by skin microdialysis in rats," Journal of Pharmaceutical Pharmacology, 50(1). pp. 49-54.

Stott, P.W., Williams, A.C., & Barry, B.W. (1998). "Transdermal delievery from eutictic systems: Enhanced permeation of a model drug, ibuprofen." Journal of Controlled Release, 50(1-3). pp. 297-308.

Morimoto, Y., & Fujimoto, S. (1985). "Albumin microspheres as drug carriers," Critical Review of Therapeutic Drug Carrier Systems, 2(1). pp. 19-63.

Johnson, M.E., et al. (1996). "Synergistic effects of chemical enhancers and therapeutic ultrasound on transdermal drug delivery," Journal of Pharmaceutical Science, 85(7). pp. 670-679.

Illel, B. (1997). "Formulation for transfollicular drug administration: some recent advances," Critical Review of Therapeutic Drug Carrier Systems, 14(3). pp. 207-219.

Frenkel, V., Kimmel, E., & Iger, Y. (2000), "Ultrasound-facilitated transport of silver chloride (AgCI) particles in fish skin." Journal of Controlled Release, 68(2). pp. 251-161.

Mitragotri, S. (2001). "Effect of therapeutic ultrasound on partition and diffusion coefficients in human stratum corneum," Journal of Controlled Release, 71(1) pp. 23-29.

Tan, H.S., & Pfister, W.R. (1999). "Pressure-sensitve adhesives for transdermal drug device systems," PSTT, 2(2). pp. 60-69.

Tajima, S., & Pinnel, S.R. (1996). "Ascorbic acid preferentially enhances type I and III collagen gene transcription inhuman skin fibroblasts." Journal of Dermatological Science, 11(3). pp. 250-253.

Castro, D.J., et al. (1987). "Biost mulative effects of Nd: YAG Q-switch dye on normal human fibroblast cultures: Study of a new chemosensitizing agent for the Nd:YAG laser," Laryngoscope, 97(12). pp. 1454-1459.

Omura, T., et al. (1984). "Hemoprotein H-450 identified as a form of cytochrome P-450 having an endogenous ligand at the 6th coordination position of the heme," Journal of Biochemistry, 96(5). pp. 1491-1500.

Hrnjak, M., et al. (1995). "Stimulatory effect of low-power density He-Ne laser radiation on human fibroblasts in vitro," Vojnosanit Pregl, 52(6). pp. 539-546.

Krammer, B., Hubmer, A., & Hermann, A. (1993). "Photodynamic effects on the nuclear envelope of human skin fibroblasts," Journal of Photochemistry and Photobiology, 17(2). pp. 109-114.

Lyons, R.F., et al. (1987). "Biostimulation of wound healing in vivo by a helium-neon laser," Annals of Plastic Surgery, 18(1). pp. 47-50.

Yu, W., Naim, J.O., & Lanzafame, R.J. (1997). "Effects of photostimulation on wound healing in diabetic mice," Lasers in Surgery and Medicine, 20(1). pp. 56-63.

Morrone, G., et al. (1998). "In vitro experimental research of rabbit condrocytes biostimulation with diode laser Ga-Al-As: a preliminary study," Artificial Cells, Blood Substitutes, and Biotechnology, 26(4). pp. 437-439.

Van Breugel, H.H., & Bar, P.R. (1992). "Power density and exposure time of He-Ne laser irradiation are more important than total energy dose in photo-biomodulation of human fibroblasts in vitro," Lasers in Surgery and Medicine, 12(5). pp. 528-537.

European Office Action dated Oct. 3, 2013 issued in European Patent Application No. 02792232.7.

Japanese Office Action dated Dec. 2, 2013 issued in Divisional Japanese Patent Application No. 2009-236857.

Canadian Office Action dated Oct. 8, 2013 issued in Canadian Patent Application No. 2640203.

\* cited by examiner

PHOTOMODULATION METHODS AND DEVICES FOR REGULATING CELL PROLIFERATION AND GENE EXPRESSION

CROSS REFERENCE TO RELATED APPLICATIONS

This application is a continuation of U.S. application Ser. No. 10/821,193, filed Apr. 4, 2005, now abandoned, which claims the priority of U.S. Provisional Application Ser. No. 60/461,412, filed Apr. 10, 2003. Each of these applications is incorporated by reference herein in their entirety.

BACKGROUND OF THE INVENTION

1. Field of the Invention

This invention relates to method and devices for the regulation of cell proliferation and gene expression. In particular, the invention relates to the inhibition of photoaging of the skin.

2. Description of the Background

Chronological aging brings about a group of changes in the appearance of human and mammalian as well as changes in the structure and function of the skin. All living cells, tissues and organs also undergo changes associated with chronological aging. Since the human skin is an organ that is highly visible, the changes associated with chronological aging are readily apparent and visible. These changes are reflections of the underlying structural and functional changes.

The phenotype associated with chronological aging of the skin is an outward reflection and expression of the genotypic changes, which occur within the cells of the skin. The most widely appreciated form of skin aging is that which is produced by over exposure and repeated chronic exposure to sunlight and is generally termed photoaging. More specifically certain portions of the ultraviolet A (UVA) and ultraviolet B (UVB) and have been determined to be the principal causative factors of what are associated with photoaging.

For many years it was thought that photoaging occurred through a different mechanism of action and was somehow different than chronological aging. However, more recently it appears that photoaging and chronological aging may share similar, if not identical pathways.

Solar radiation is composed of ultraviolet (UV), visible and infrared, light. Current conventions divide UV radiation into UVA (320-400 nm), UVB (290-320 nm) and UVC (<290 nm). UVC radiation is blocked by ozone in the stratosphere and does not reach the earth's surface, but can be generated by germicidal lamps and other machinery. UVA and UVB sunlight do reach the earth and are believed to be the principal agents of photoaging. UVA radiation is further subdivided into UVA 1 and UVA 2. While UVB has been believed to be the primary agent for photoaging, it is now appreciated that certain wavelength ranges within the UVA rays also contribute to changes associated with photoaging.

UVA and UVB light exposure to human skin triggers a series of molecular events including the induction of reactive oxygen species (ROS) in the skin. Through a series of cell signaling events collagen production is down-regulated and various enzymes known to degrade structural proteins in the skin up-regulated. The net result of this is a decrease in collagen and the production of wound. The skin's reaction to UVA or UVB (or combined) wounding is to repair the wound through the skin's wound healing mechanism. Typically these wound repair mechanisms are imperfect which is considered by many to be a solar scar. After many years of the UVA or UVB wounding of the skin, chronic solar scarring develops which manifests itself in the visible phenotypic changes termed photoaging, which might also be considered the visible outward evidence of solar scars.

Photoaging of the skin may occur through acute injury at higher levels, such as what one associates with sunburn. This triggers an inflammatory process in the skin and the associated cellular mechanisms. There is also a more chronic low-level type of injury that does not produce a sunburn reaction, but which produces the changes of chronic photoaging. Other processes, which are known to decrease collagen production and increase collagen-dissolving enzymes, such as tobacco smoking, also are associated with changes that visibly appear, similar to the photoaging from UVA/UVB light. This can be seen strikingly in photographs of identical twins wherein only one twin smoked tobacco for many years.

UVB radiation in sufficient doses produces reddening or sun burning of the skin. The threshold level is typically described as minimal erythemal dose (MED), typically produced by 290-300 nm UVB wavelengths. As the wavelengths increase they become much less likely to produce the redness and burning reactions and indeed wavelengths of 320 nm are about 100 times as powerful as wavelengths of 340 nm approximately 100 times less powerful than the 290-300 nm range of producing erythema and sunburns. The total UVB exposure is more related to the appearance of photoaging and sunburns are more likely to trigger malignant changes in the skin such as malignant melanoma. In contrast, UVA radiation can produce redness, but also produced tanning and these are the wavelengths typically used for the so-called tanning beds. UVA radiation is a longer wavelength and is proportionately greater in the early morning and late afternoon than the UVB rays, which are typically most predominant and intense at the midday summer sun time exposure period. UVA radiation may also penetrate certain sun blocks and certain sunscreens and also window glass on automobiles, thus accounting for the frequently observed greater wrinkling, brown pigmentation and redness and overall aged appearance on the left side of the face than the right in patients who occupationally or recreationally spend considerable time driving a left hand drive motor vehicle.

In sunny countries with fair complexioned populations, such as Australia, where right hand drive motor vehicles are used, these changes are typically seen on the right side of the face. The patterns of photoaging are determined by which areas of the body are anatomically more chronically exposed to sunlight. Thus, the face, neck, back of hands, upper chest, lower arms, lower legs and depending on hair styling and density, ears and balding areas manifest the greatest photoaging changes.

The chronological changes and photoaging changes typically are manifest by fine lines and wrinkling of the skin, a coarser, crepey texture to the skin, skin laxity and skin sagging, uneven pigmentation, brown splotchy pigment, loss of skin tone, texture and radiancy, bruising and sallowness. The skin is composed of several layers, the outermost layer is called the stratamocornium (SC), the next layer is the epidermis (EPI), and underneath the epidermis lies the dermis (DER). The outer SC serves primarily a barrier function to protect the skin from environmental exposure and also to help minimize water loss from the skin. The epidermis serves many important and diverse roles as does the dermis. The dermis contains the principal structural proteins of the skin. These proteins are collagen, elastin and ground substance. They are manufactured by the fibroblast cells within the dermis. Fibroblast cells control the activity to produce these proteins as regulated by a complex and relatively well defined series of cell receptors and cell signaling mechanisms.

The proliferation of these cells is also an important activity. For example, the dermis also contains blood vessels, nerve fibers, oil and sweat glands, hair follicles and many other important components. There is a remarkably complex inner communication through cell signaling in the cells of the skin. Fibroblasts produce what are termed pro-collagen fibers, which are then insymmetrically assembled into collagen fibers, and form bundles within the dermis. Other molecules, such as decorin affect the function of the collagen. There are various sub-types of collagen fibers such as Collagen I, III, etc., within the body. Collagen I comprises approximately 85% of the skin and Collagen III approximately 10%. However, in photoaged skin the amount of Collagen I decreases so the ratio of Collagen III/I is altered.

There are also a variety of enzymes termed matrix metalloproteinases (MMP) which play important roles in aging skin. Fibroblasts also have important functions in wound healing with the removal of damaged structural ECM and the repair and production of ECM. The Collagen I is degraded principally by MMP 1 (collagenase). There are a variety of MMP enzymes, which degrade one or more of the structural proteins in the skin. While these degrading MMP enzymes serve an important role in removing damaged skin (for example, in wound healing), their activation and synthesis in increased quantities in normal skin helps contribute to the changes seen in both chronological and photoaging. Likewise, if the production of Collagen I is decreased or diminished, this results in changes which are associated with chronologically or photoaged skin. Aging or senescent fibroblasts may exhibit decreased synthesis of Collagen I and increased synthesis of MMP 1. Similar changes are seen with UVA/UVB exposure. Other environmental agents may produce similar changes.

Certain drugs, therapies, chemicals, active agents have been demonstrated to reverse the appearance of or phenotype of a chronologically aging or photoaging skin. Some topically applied agents serve as a physical or optical barrier either by reflection or absorption of ultraviolet light thus protecting the skin. There are also enzymes that have been shown to actually repair the DNA dimers which are produced from UV damage. Other topically applied or oral or systemically applied agents have been shown to improve the appearance of the skin. One of the classic and well-known agents is a topical Vitamin A derivative termed Retinoids. Numerous studies have demonstrated the ability to improve the appearance or phenotype of photoaged skin with the use of all-trans retinoic acid (RA). Many of the cell signaling pathways involve the mechanism of action of RA and also Retinol (RO). Much of the mechanism of action of RA in the cell signaling pathways appears to produce anti-aging effects.

One of the goals of some current anti-aging therapies is to increase production of collagen in the ECM and the dermis of the skin. Some believe collagen I is the more desirable form of collagen to increase. There is some support for this since photoaged skin has less desirable visco elastic properties and this is thought in part to be due to the increased proportion of collagen III to collagen I. Other anti-aging approaches indicate that reducing the activity or production of the degrading enzymes in the ECM will similarly produce an anti-aging effect in the appearance of the skin. Doing a combination of both is even more beneficial. An analogy one might make is the production of new collagen I and that of freshly newly fallen snow. The amount of accumulation of the fresh snowfall is dependent both on the amount of snow that is fallen as well as the amount of the freshly fallen snow which then melts. Thus one could envision an anti-aging therapy which stimulated new collagen production (newly fallen snow). When a piece of black asphalt in a parking lot abuts a piece of warmer black asphalt adjoining a colder piece of concrete or frozen ground, while the amount of new snowfall is equal in both areas, the amount of accumulated snow melted by the warmer asphalt is more than the amount of snow melted by the frozen concrete. If an anti-aging therapy stimulates collagen I production, but does not diminish MMP 1 activity, the net increase in collagen I will be smaller than if the MMP 1 activity is also decreased.

Historically there have been many approaches to restoring a youthful appearance to human skin for achieving anti-aging or age reversal therapies. Most methods utilize some form of triggering the body's own wound healing mechanism. The more destructive and traumatic methods use chemicals to peel off the stratum cornium epidermis and often a portion of the dermis or mechanically abrade the skin by sand papering or dermabrating or more recently use high-energy thermal lasers to vaporize or coagulate the skin. These methods have a prolonged and painful wounding period and require wound care. Patients typically must limit their daily social and business activities during the wound-healing phase. Subsequently the skin undergoes months or years of an ongoing wound healing and wound remodeling process, whereby damage is repaired and new structural proteins in skin are generated. These treatments typically amount to trying to produce a controlled entry to the skin and providing the wound care environment that minimizes the risk of scarring. These methods are notoriously known for producing many problems and sometimes even disfiguring scarring or catastrophic pigment changes in the skin. However, properly performed and with good wound care, many people achieved significant and sometimes dramatic anti-aging effects. Other gentler methods have become more popular in recent years which involve the classic plastic surgery lifting procedures and newer procedures termed non-ablative, where the outer stratum cornium and epidermis are not removed or blated from the skin, but are by various means and methods protected and left in tact. Non-ablative methods have typically been thermal in nature and through various means of laser light, intense pulsed light, radio frequency or microwave energy delivery then produced a thermal injury to the dermis. The theory behind these therapies is that this injury will result in a net increase in the desirable structural proteins, while not triggering, worsening, scarring or other complications. Results are occasionally traumatic but have been extremely variable with this therapy. The variability in individual wound healing repair mechanisms, overall health of body and skin, and many other factors contribute to this variability in results.

There are various topical agents that have been developed for anti-aging purposes such as Retinoic acid, topical Vitamin C, topical Vitamin E and other antioxidant and other anti-wrinkle creams and lotions. Many of these are well defined.

There is a need to improve the appearance of chronologically aged, photoaged, or environmentally damaged skin, but without producing the risk, complications, recovery time, pain, discomfort, wound care or other side effects traditionally associated with surgical, chemical, electromagnetic radiation and other types of therapies.

SUMMARY OF THE INVENTION

As embodied and broadly described herein, the present invention is directed to method and devices for improving the appearance of photoaged or damaged skin. Methods and devices involve the regulation of cell proliferation and gene expression of skin and other cells.

One embodiment of the invention is directed to methods for both inhibiting, as well as reversing the appearance of photoaging (beauty maintenance) or chronological or environmentally damaged induced aging of human skin by application of photomodulation by, for example LED or other electromagnetic radiation treatment. Preferably, the invention is directed to the regulation of cell proliferation of cells of the skin, and/or the regulation of gene expression in such cells.

Another embodiment of the invention is directed to the various genotypes that characterize different phenotypes of aging skin and also a database comprising a collection or library of such phenotypes. The database may comprise a plurality of genotypes identified from a variety of different individuals with the same disorder, or a variety of individuals with different disorders.

Another embodiment of the invention is directed to photomodulation by light or electromagnetic radiation so as to effect cell proliferation and/or gene expression. Examples of different types of electromagnetic radiation include ultrasound, radiowaves, micro rays, magnetic fields, any electrical stimulation that produces changes in the genotype or phenotype of aging skin, and combinations thereof.

Other embodiments and advantages of the invention are set forth in part in the description, which follows, and in part, may be obvious from this description, or may be learned from the practice of the invention.

BRIEF DESCRIPTION OF THE DRAWING FIGURES

DESCRIPTION OF THE INVENTION

Figure 1:
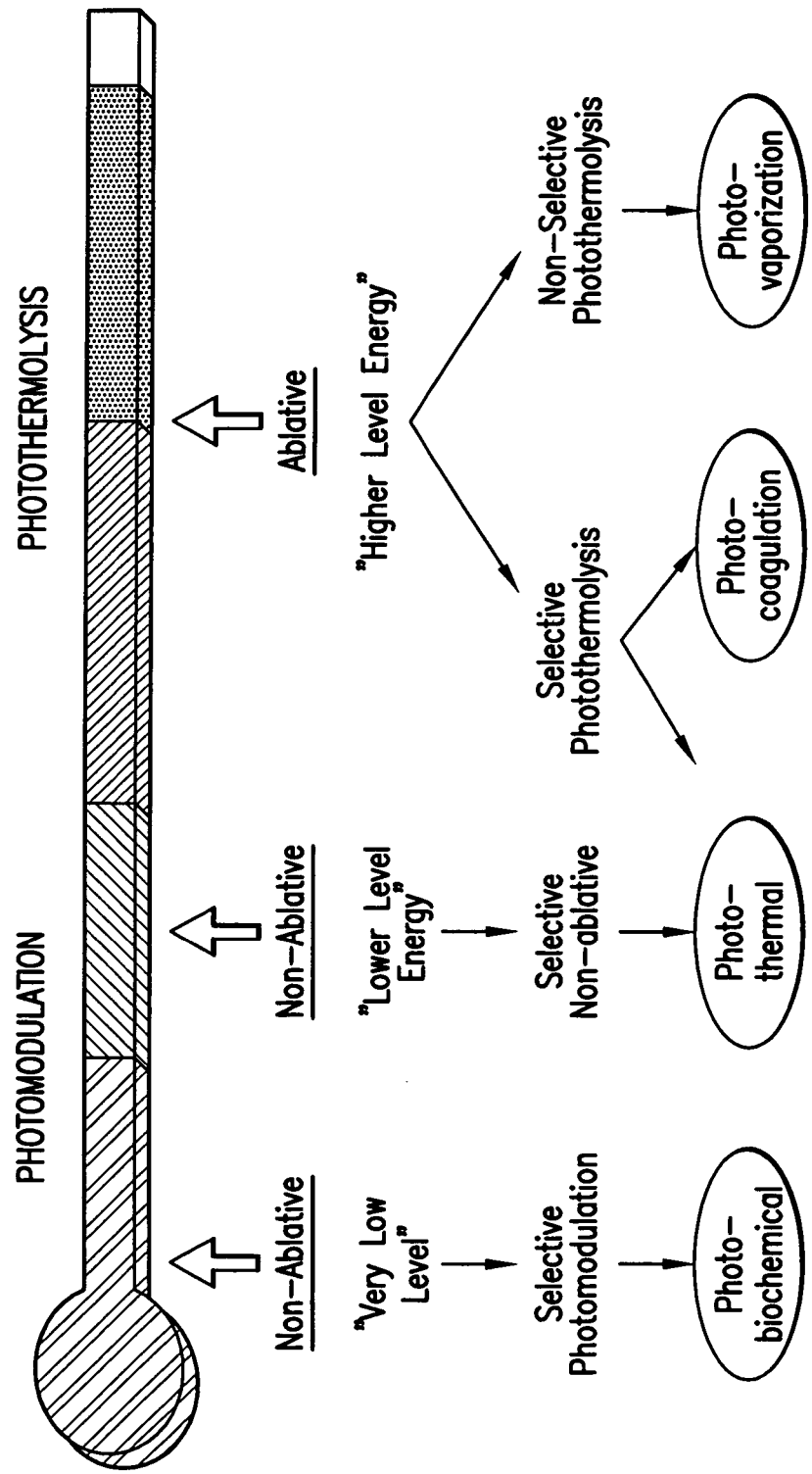
FIG. 1 illustrates light intensity levels and nomenclature for light therapy regimes.
Figure 2:
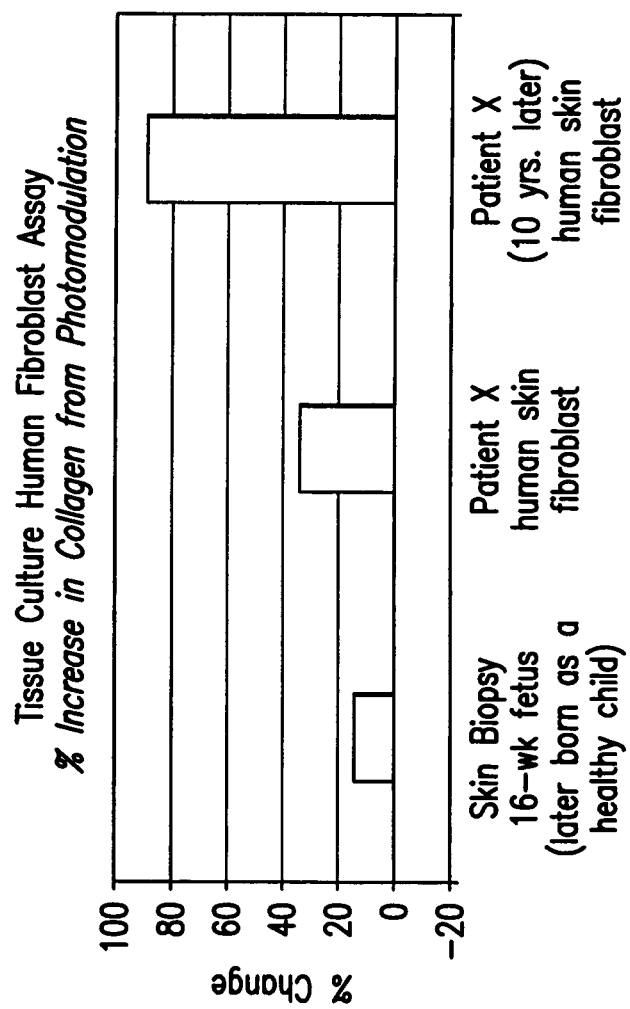
FIG. 2 shows a tissue culture human fibroblast assay.
Figure 3:
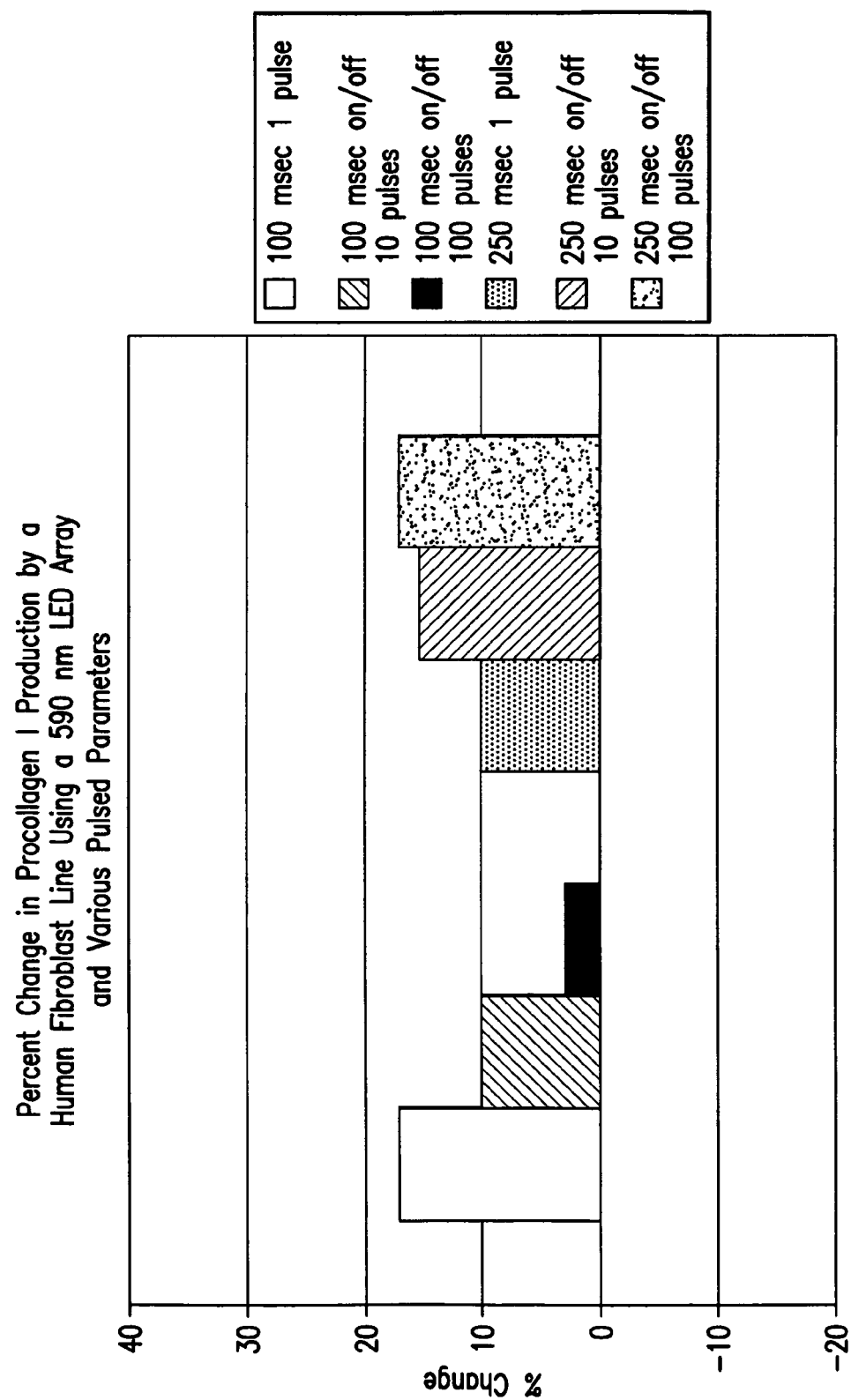
FIG. 3 shows an illustrative effect of light therapy on procollagen I production.
Figure 4:
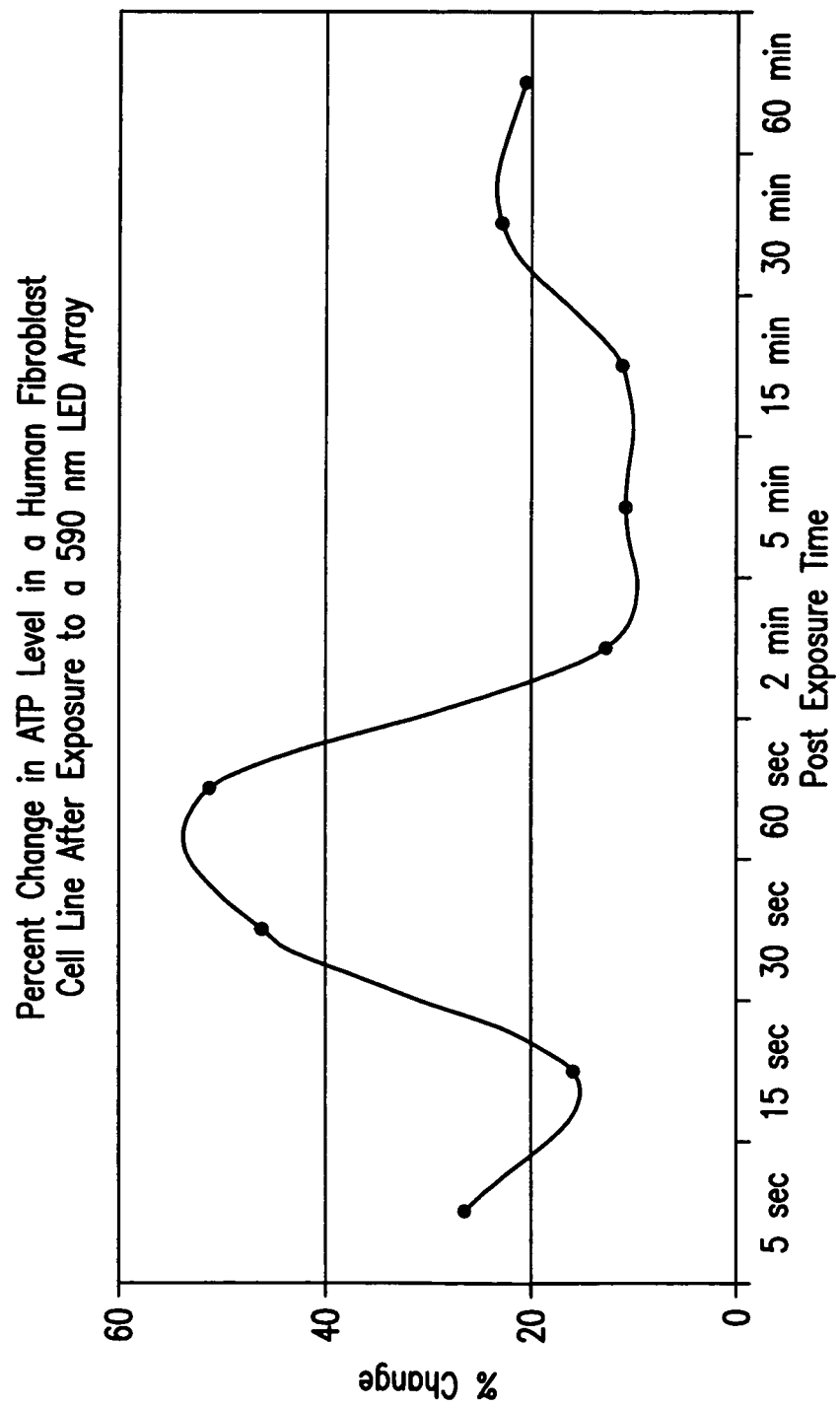
FIG. 4 shows a change in ATP level in human fibroblast after exposure to light therapy.
Figure 5:
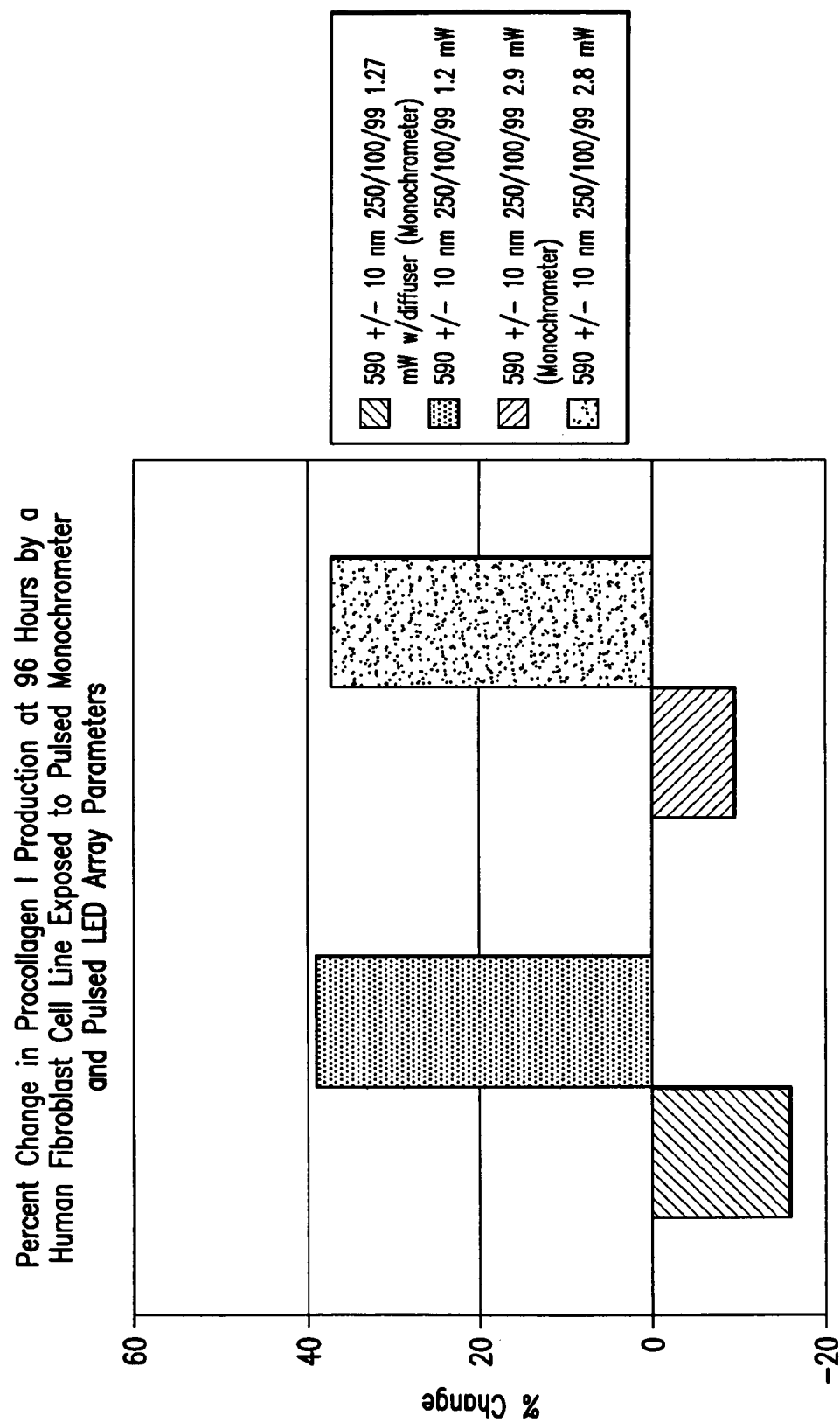
FIG. 5 shows an illustrative effect of light therapy on procollagen I production.
Figure 6:
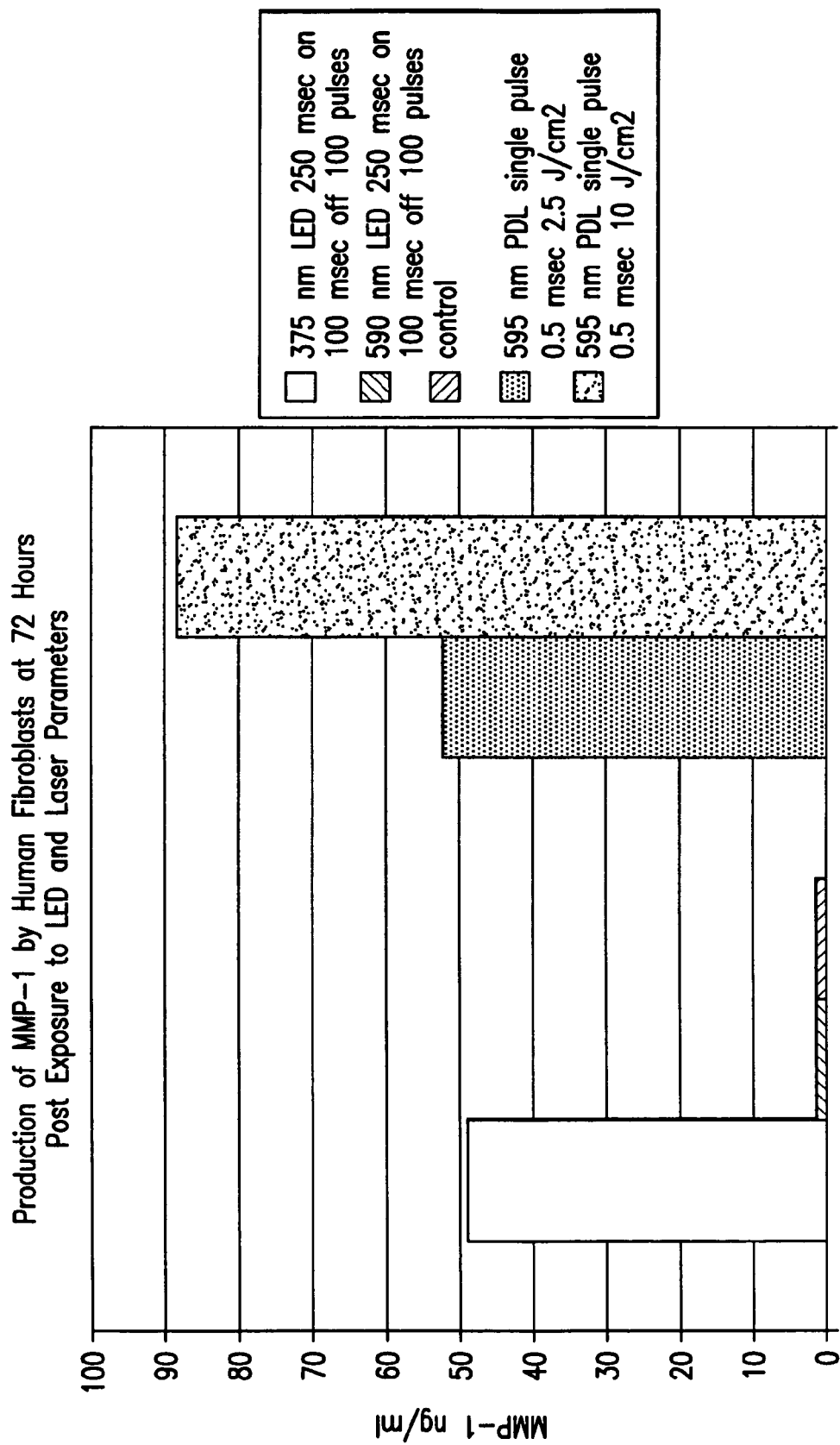
FIG. 6 shows an illustrative effect of light therapy on MMP-1 production.
Figure 7:
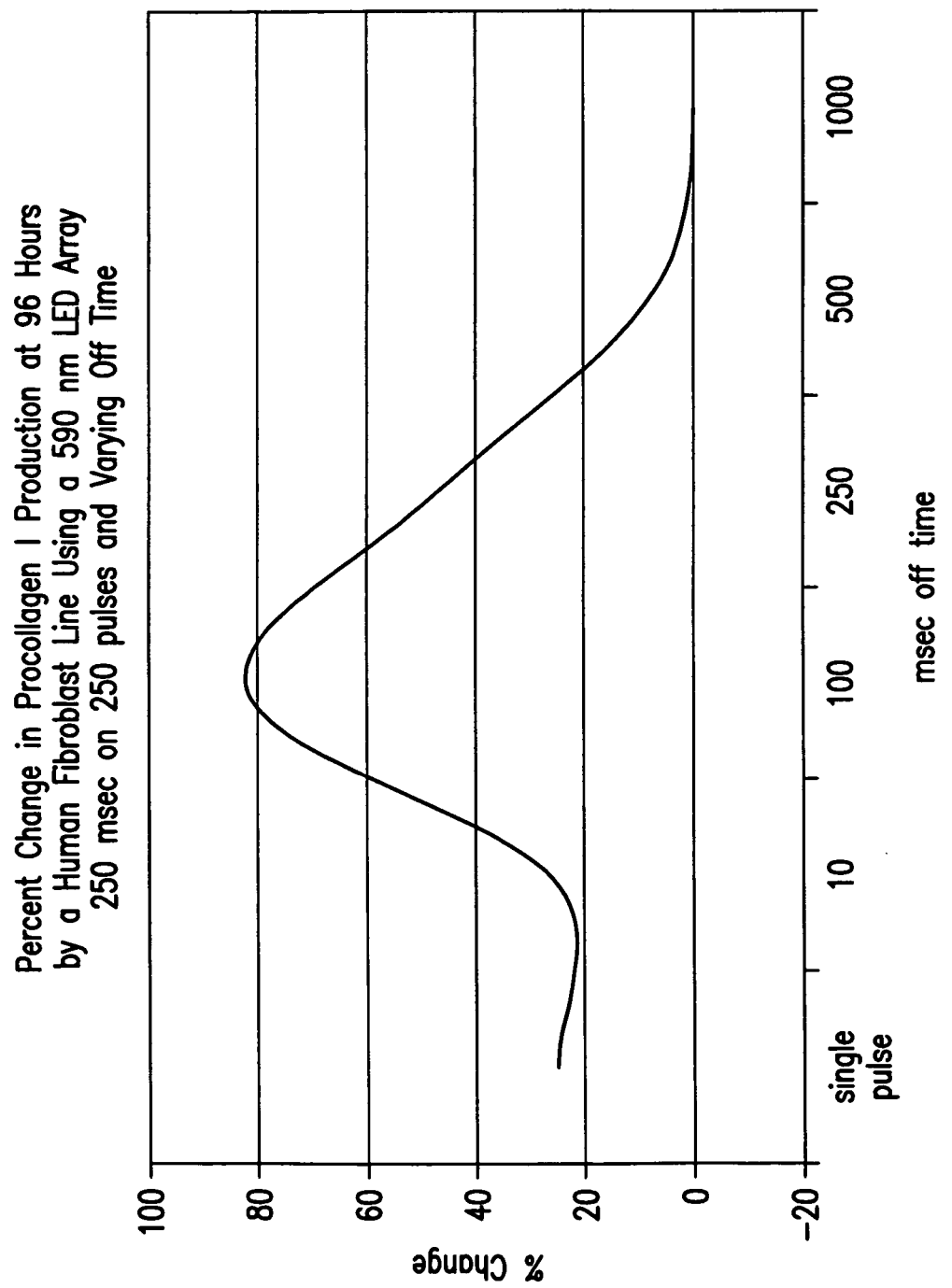
FIG. 7 shows another illustrative effect of light therapy on procollagen I production.
Figure 8:
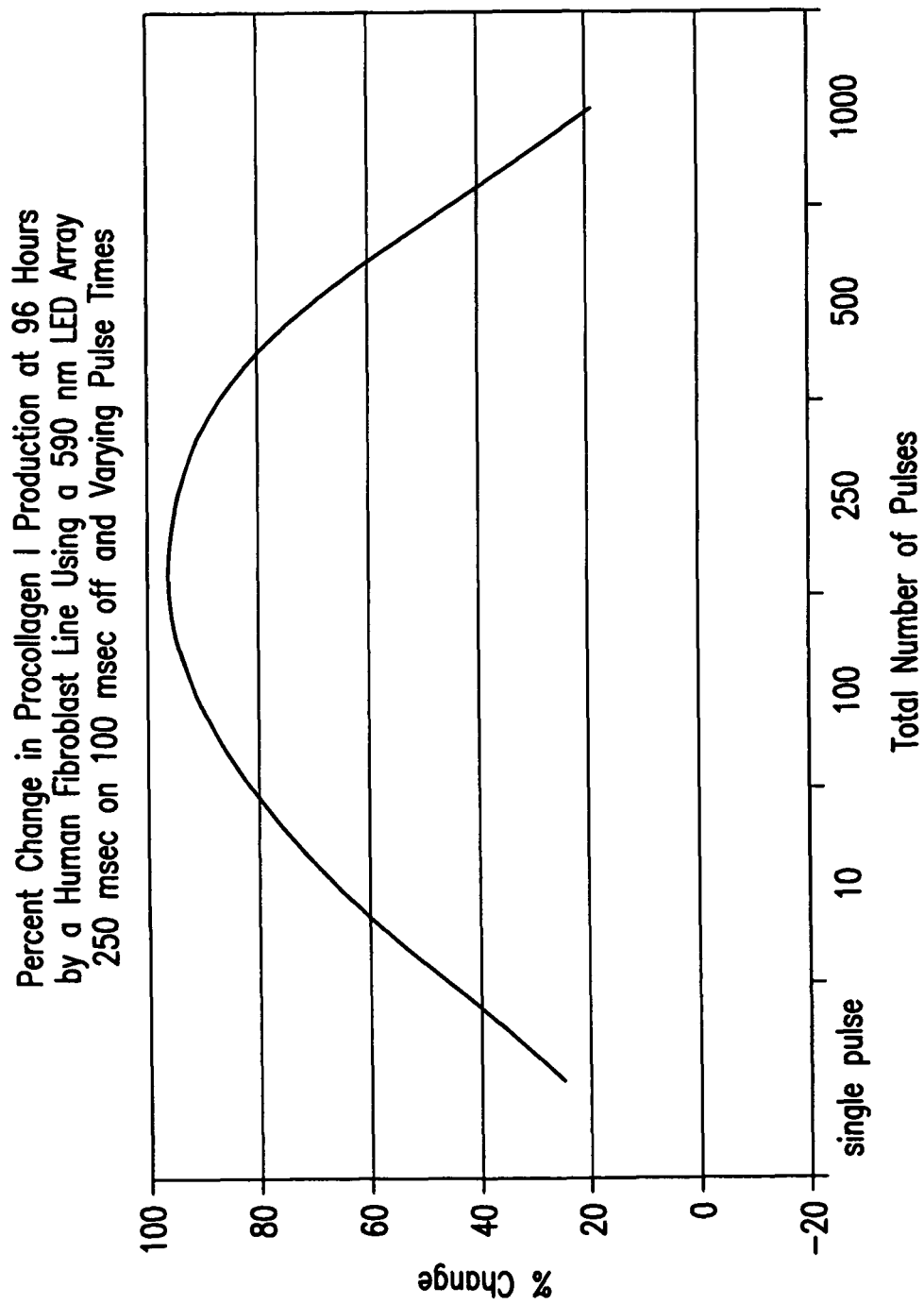
FIG. 8 shows another illustrative effect of light therapy on procollagen I production.
Figure 9:
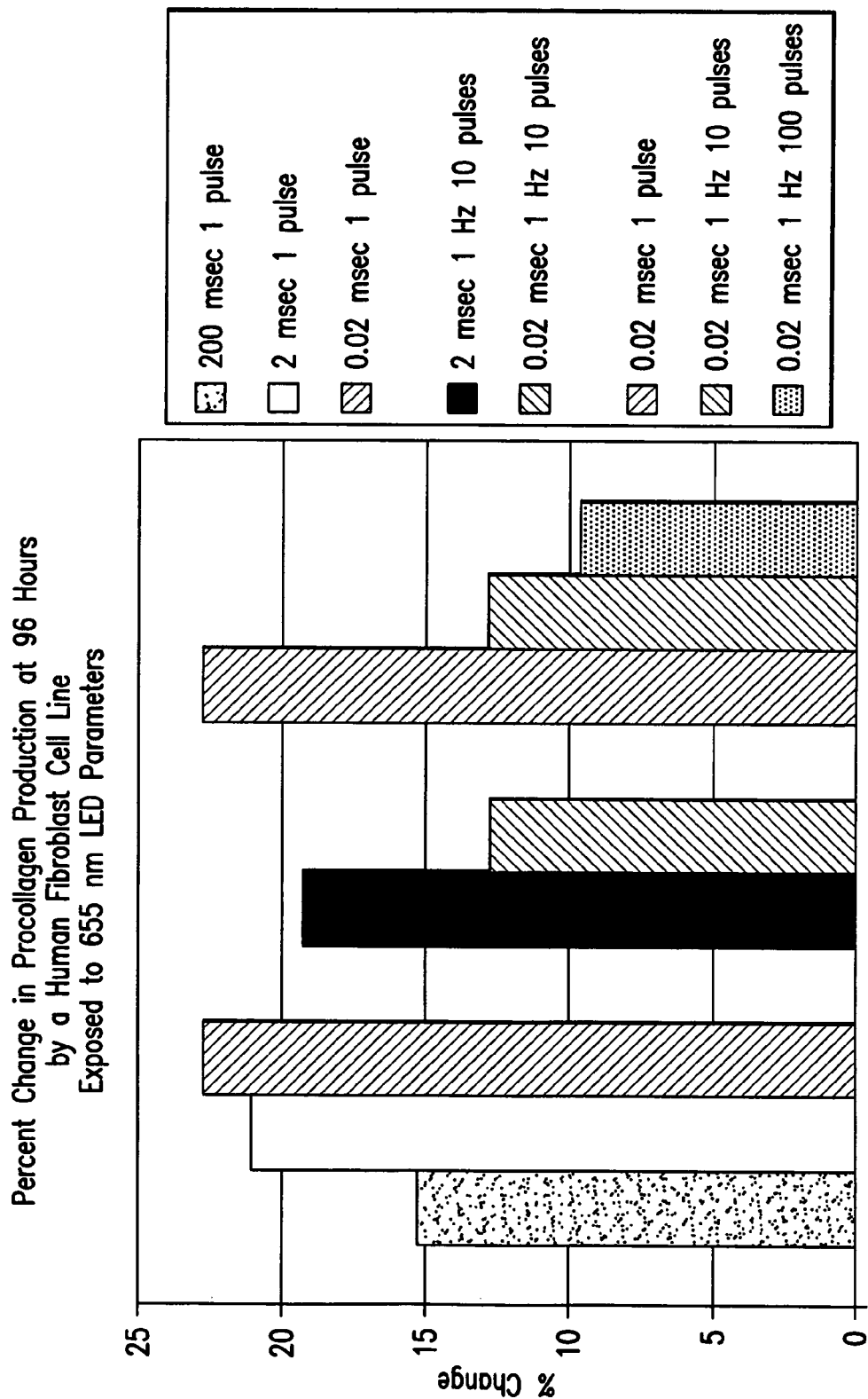
FIG. 9 shows an illustrative effect of light therapy on procollagen production with varying light exposure patterns.
Figure 10:
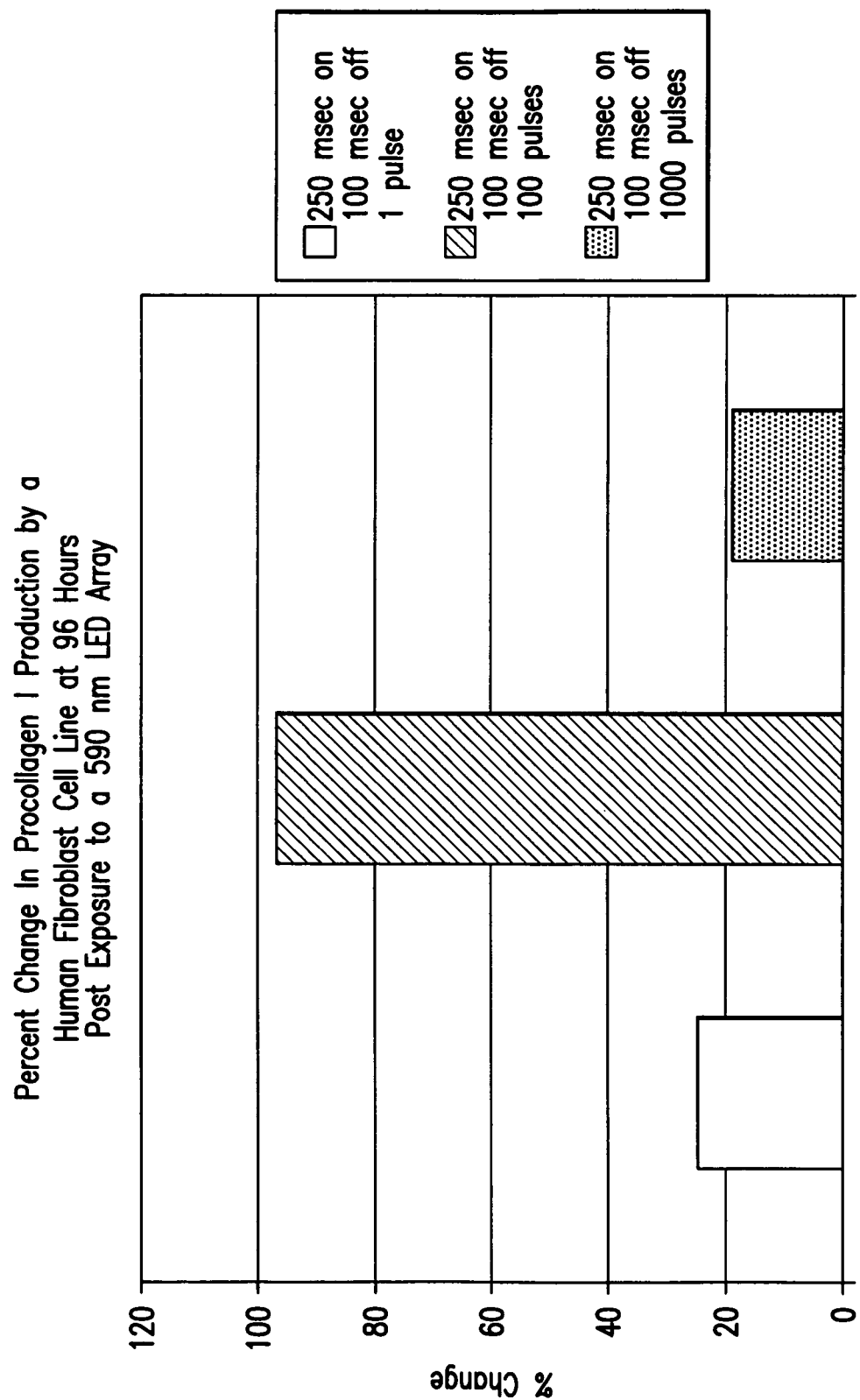
FIG. 10 shows an illustrative effect of light therapy on procollagen I production with varying light pulse patterns.
Figure 11:
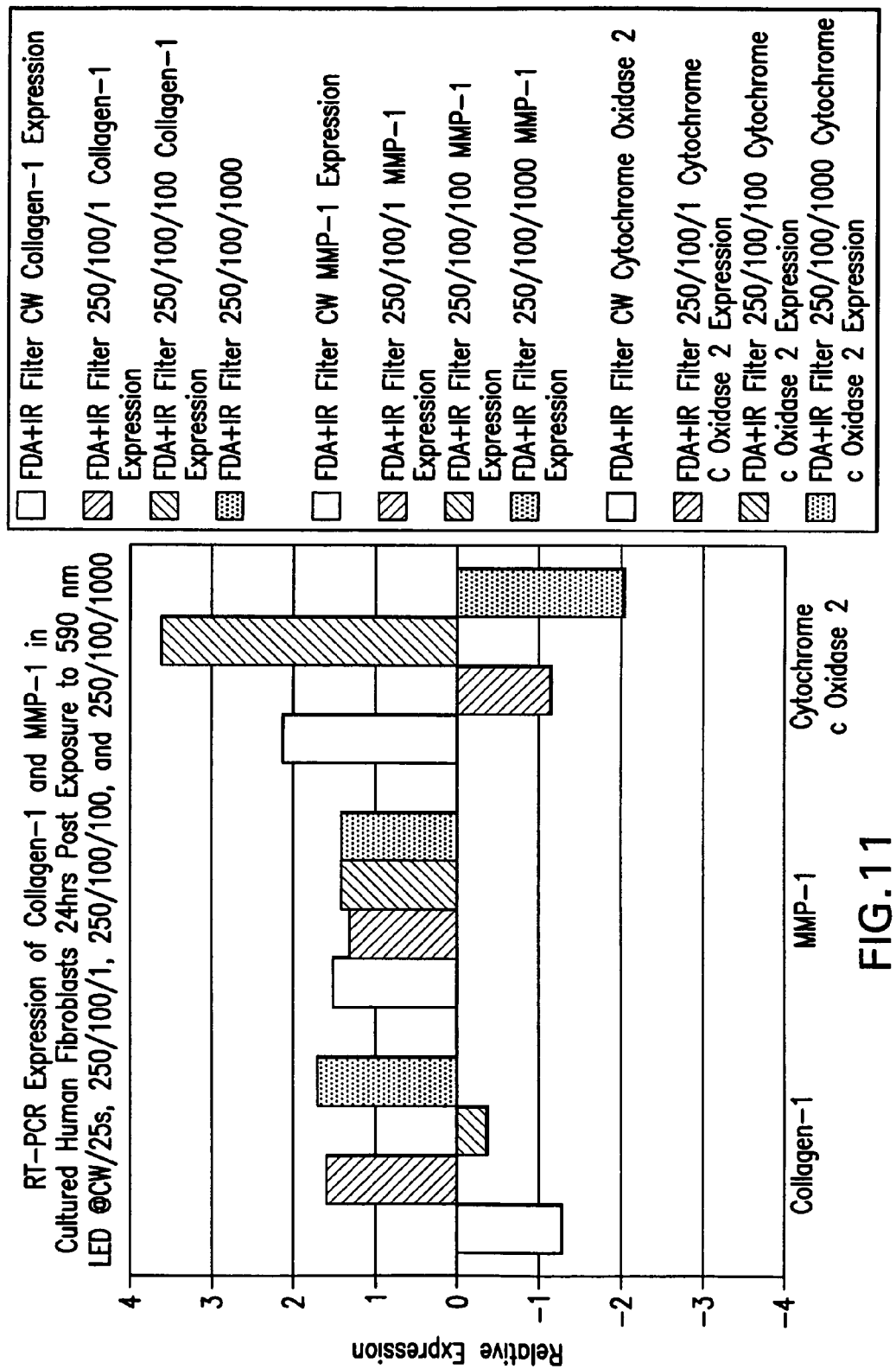
FIG. 11 shows an illustrative effect of light therapy on RT-PCR expression of procollagen I and MMP-1 in cultured human fibroblasts.
Figure 12:
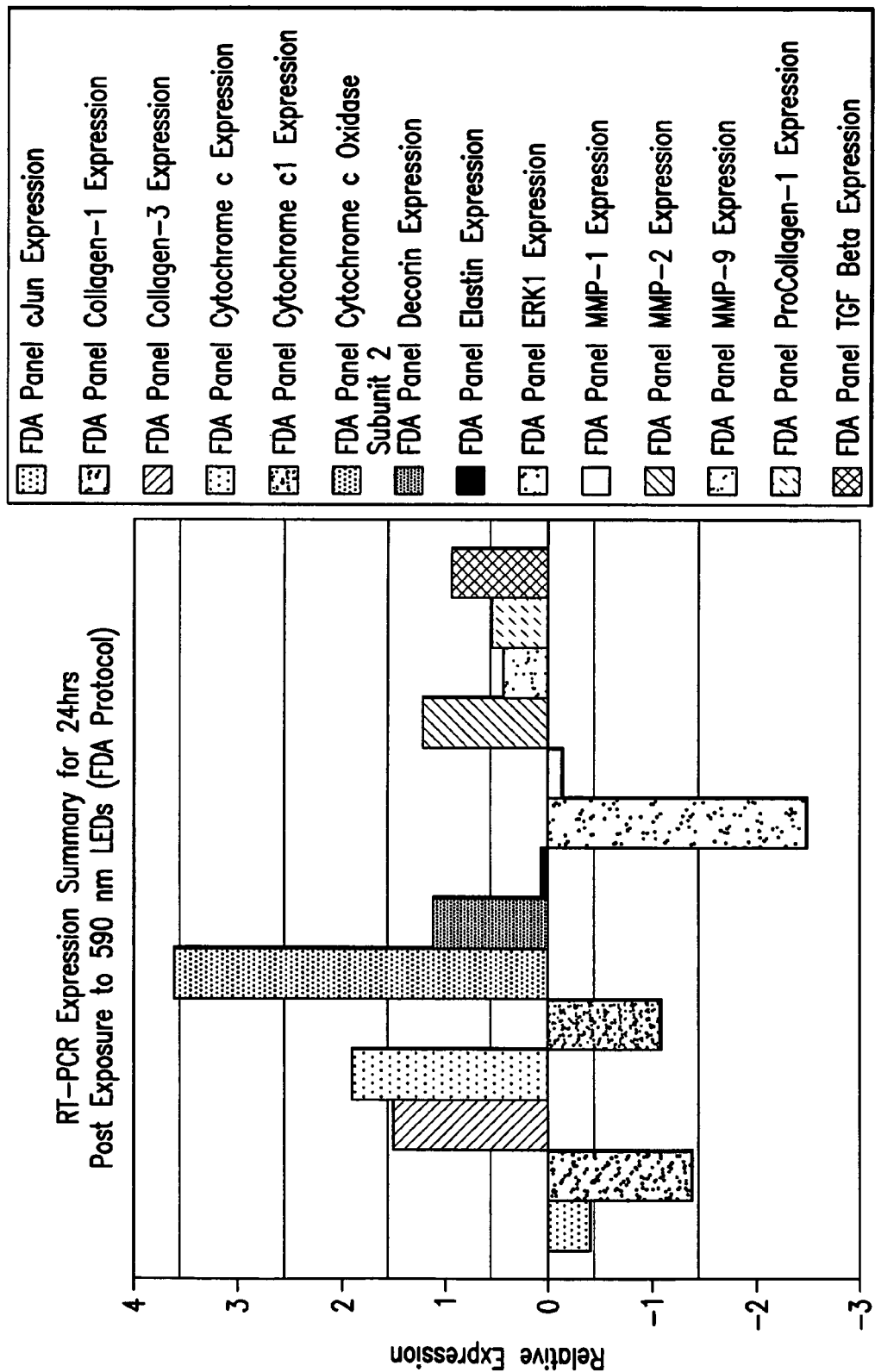
FIG. 12 shows an example of RT-PCR expression summary 24 hours after exposure to light therapy.
Figure 13:
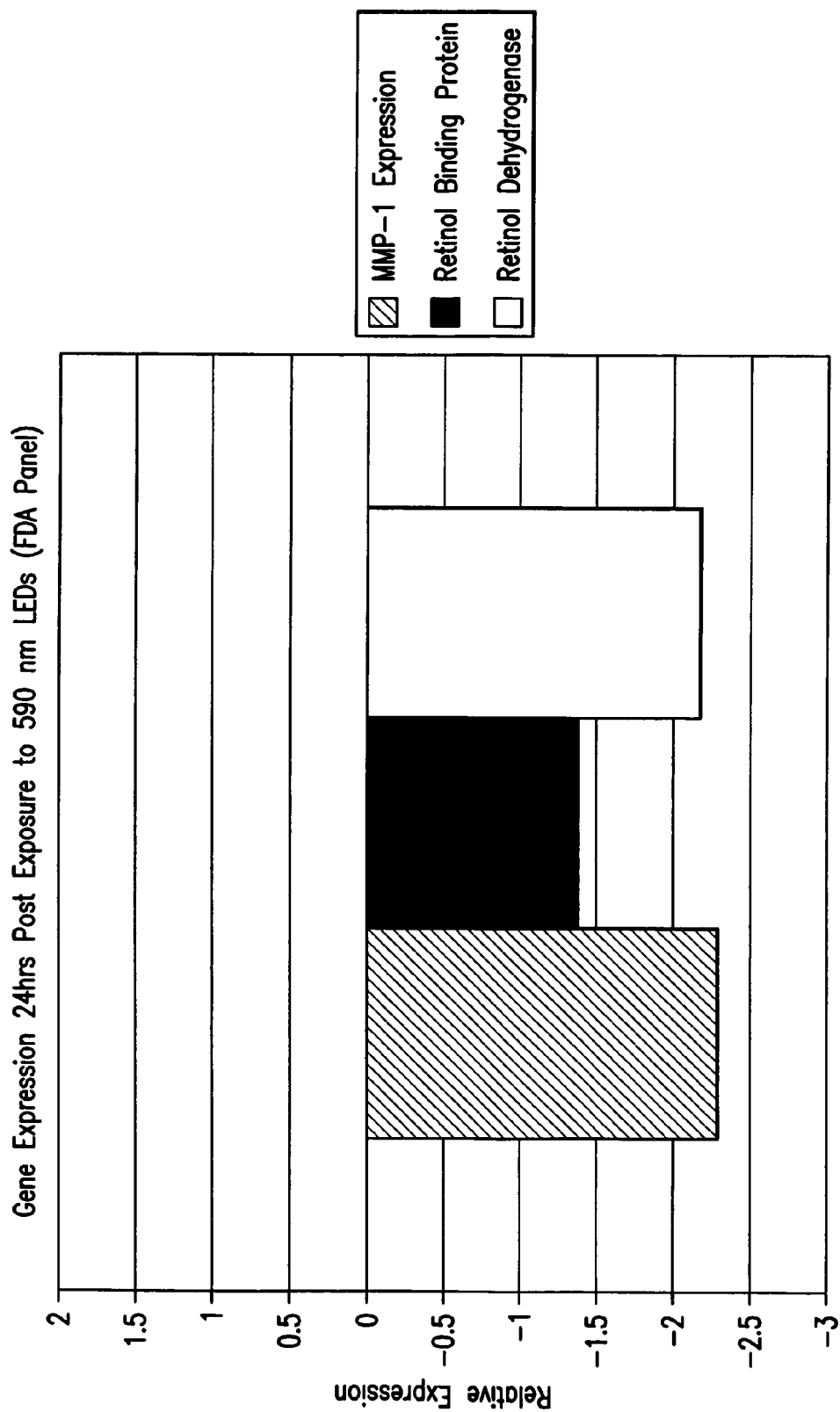
FIG. 13 shows an example of gene expression 24 hours after exposure to light therapy.
Figure 14:
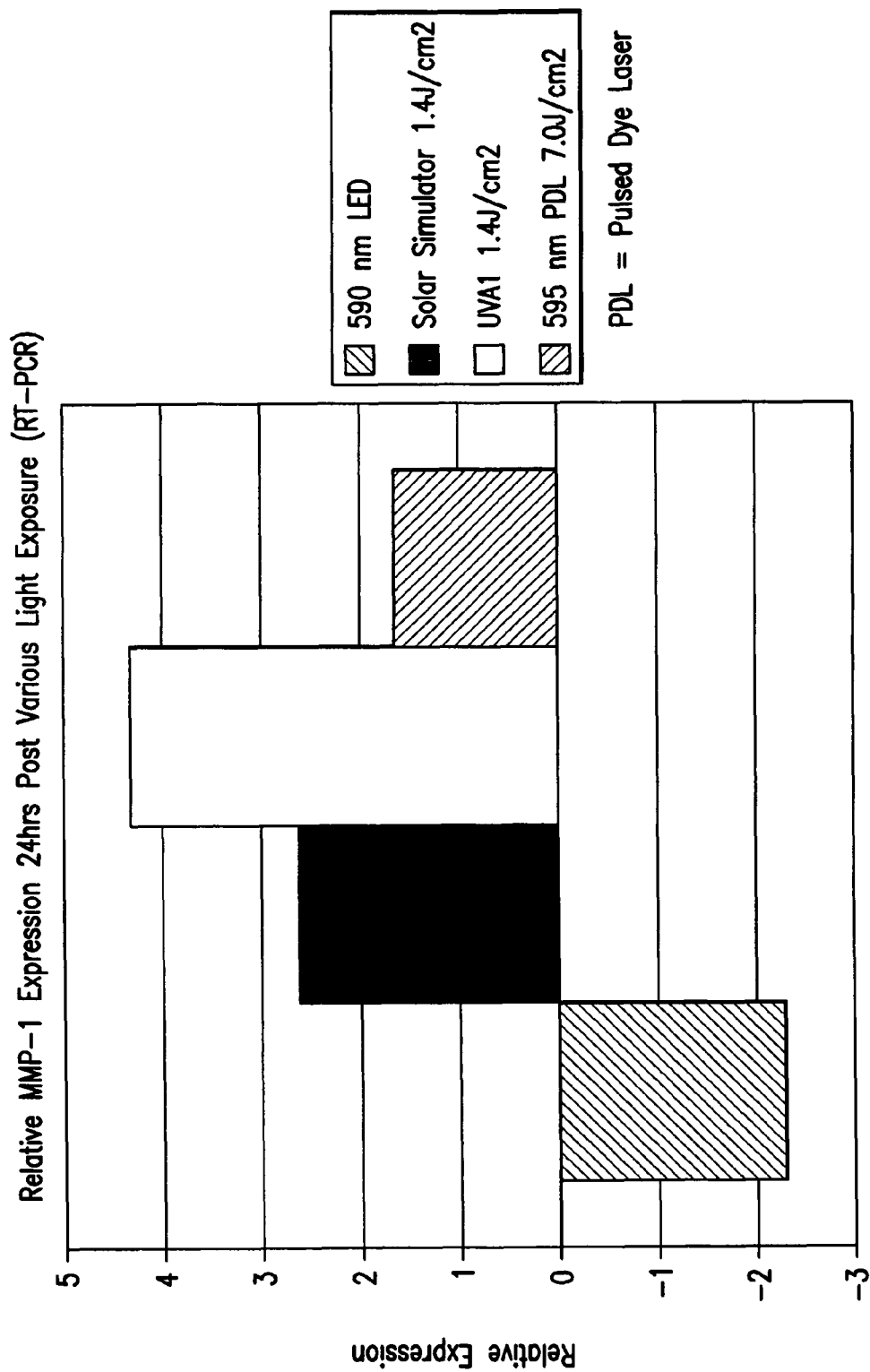
FIG. 14 shows an example of relative MMP-1 expression 24 hours after exposure to light therapy.
Figure 15:
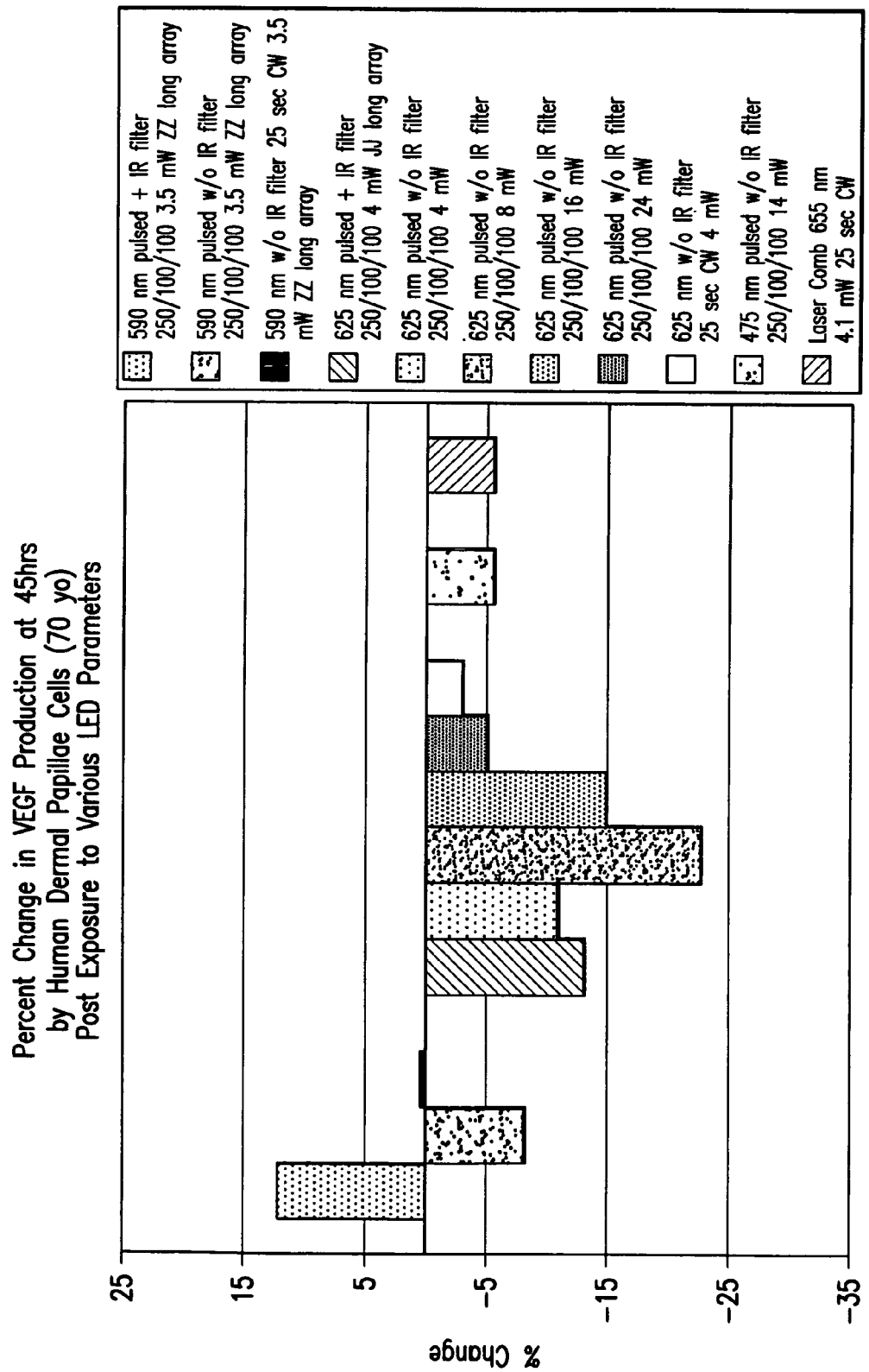
FIG. 15 shows an example of the effect of light therapy on VEGF production by human dermal papillae cells.
Figure 16:
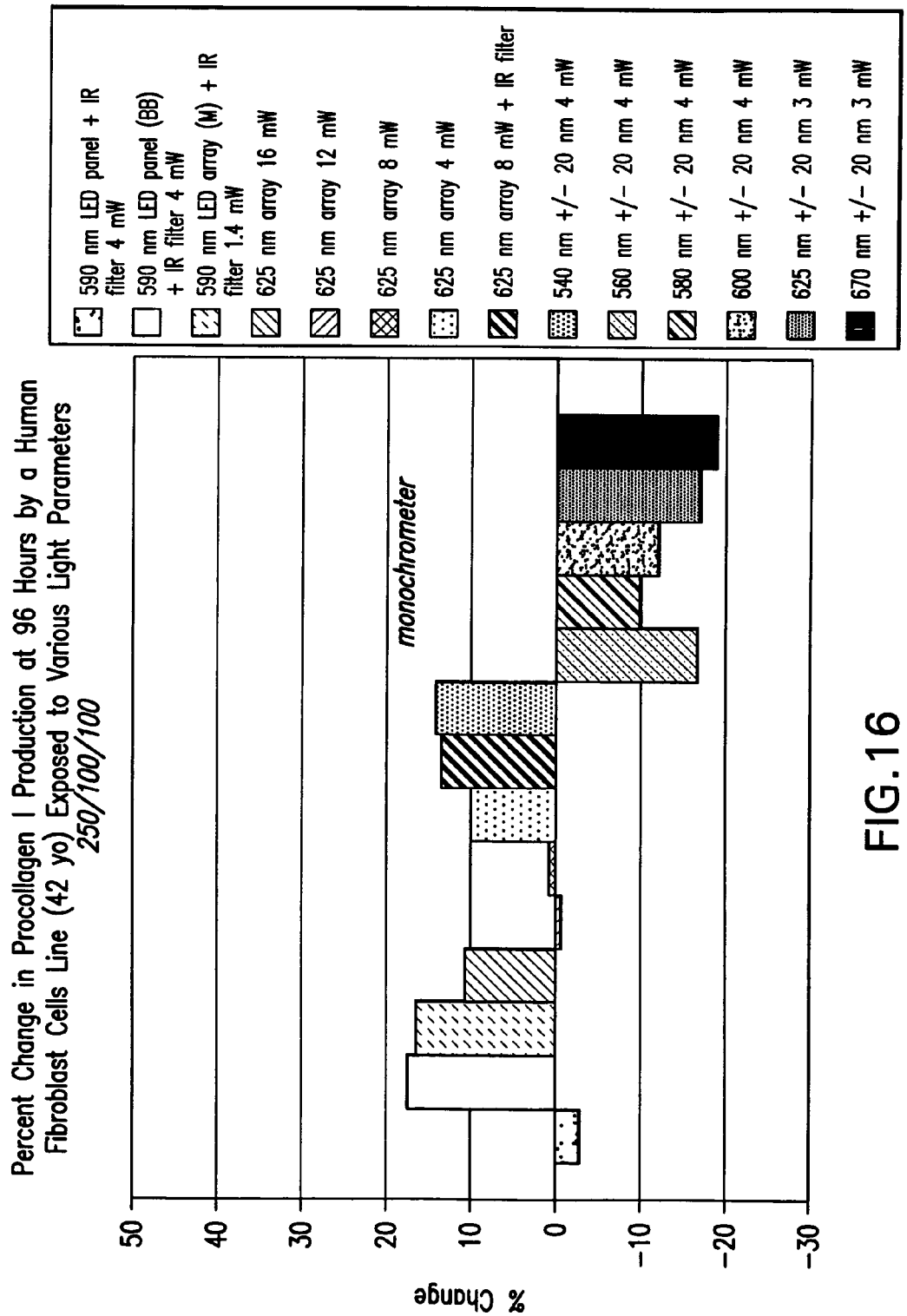
FIG. 16 shows an illustrative effect of light therapy on MMP-1 production at various treatment parameters.
Figure 17:
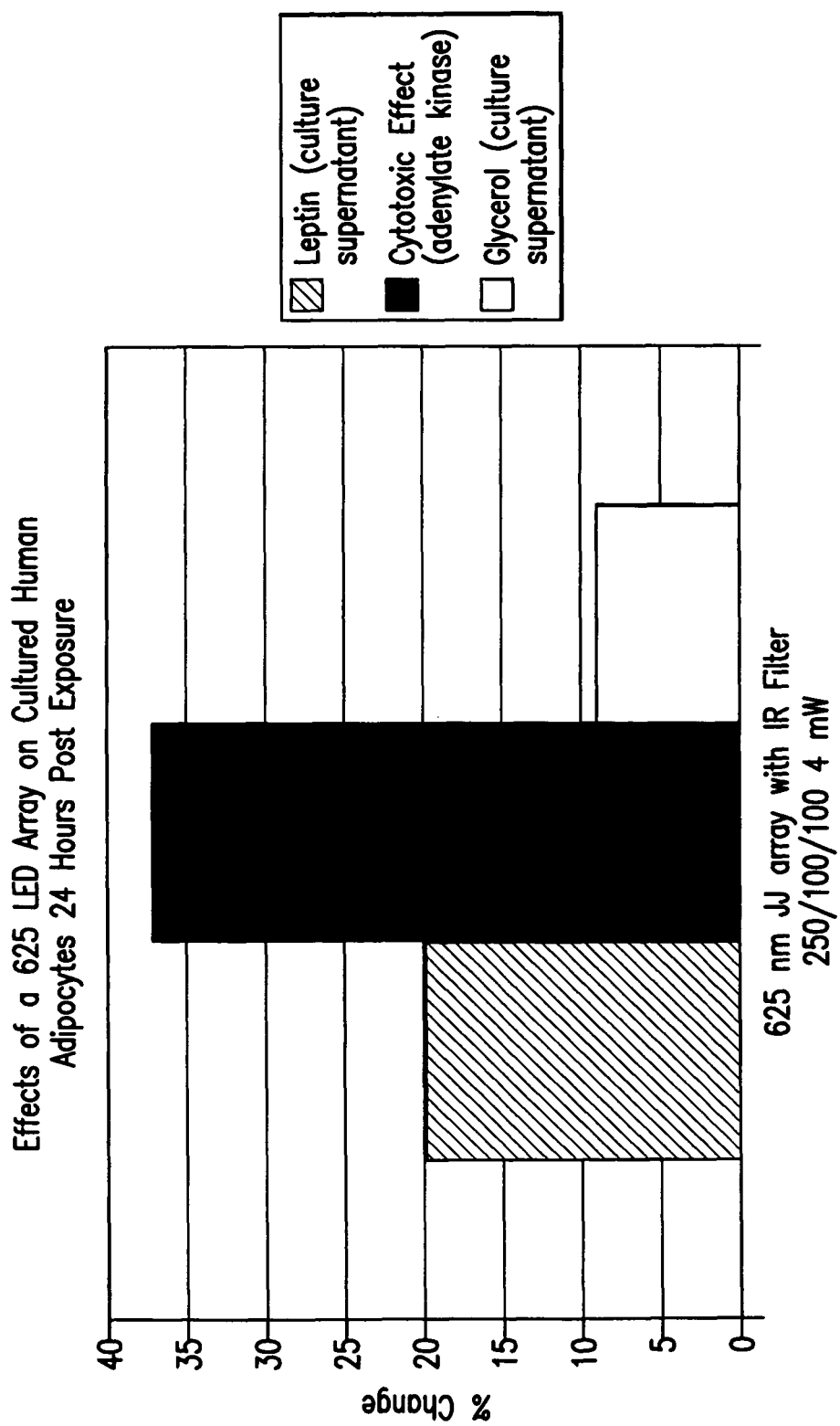
FIG. 17 shows an example of the effect of LED therapy on cultured human adipocytes.
Figure 18:
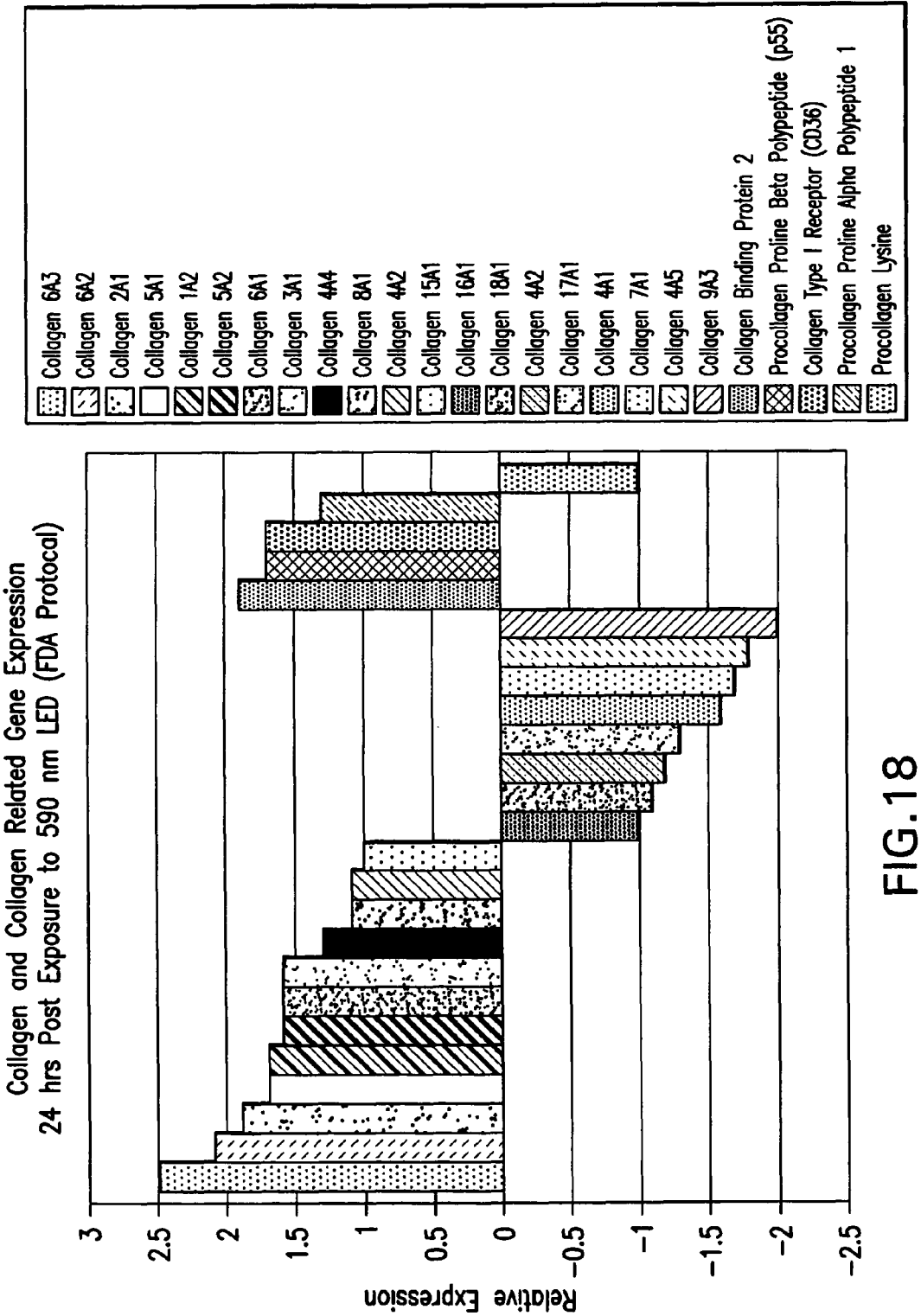
FIG. 18 shows an example of the effect of 590 nm LED therapy on collagen and collagen related gene expression.
Figure 19:
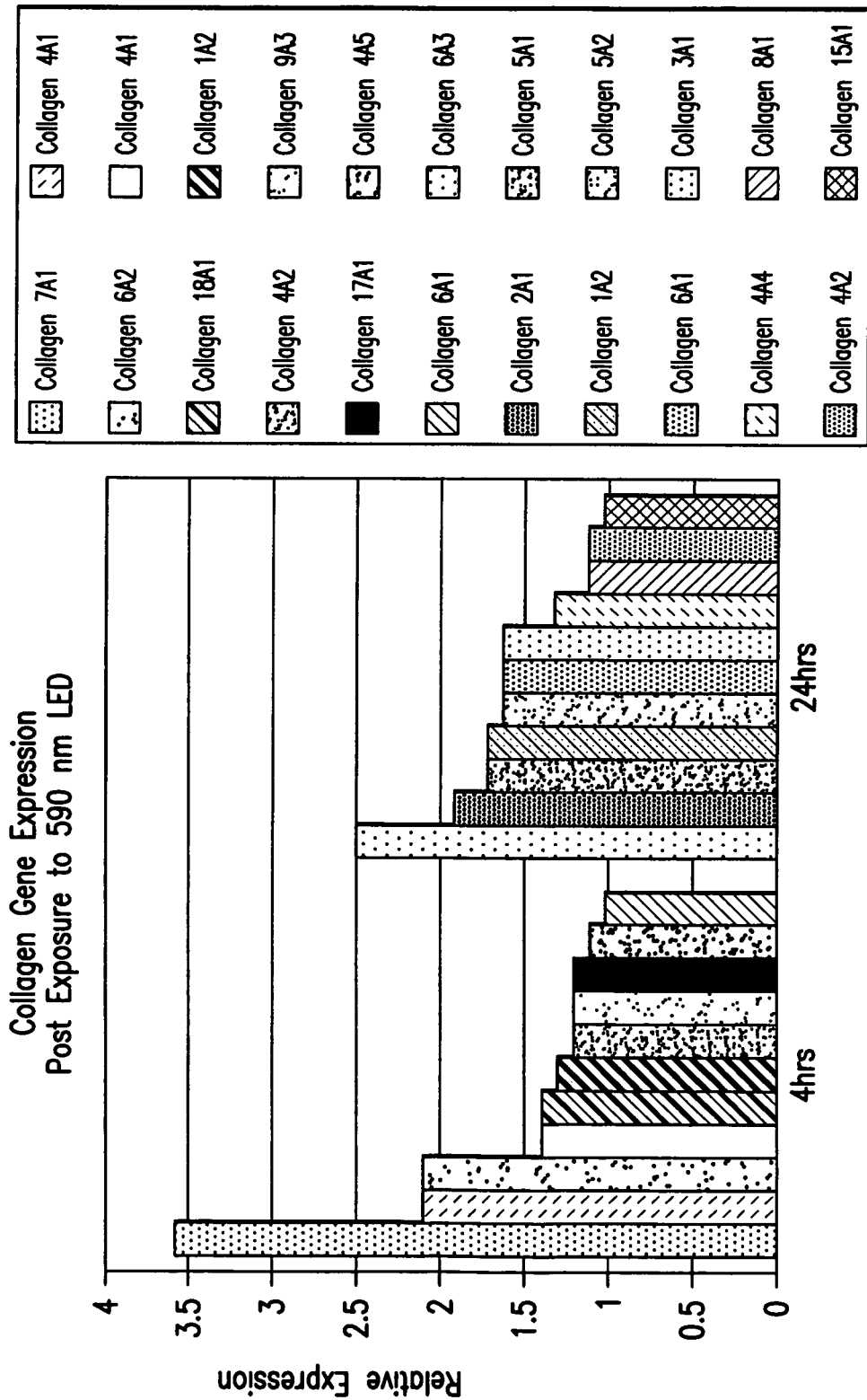
FIG. 19 shows an example of the effect of 590 nm LED therapy on collagen and collagen related gene expression after 24 hours.

As embodied and broadly described herein, the present invention is directed to methods and devices for the regulation of cell proliferation and gene expression and, in particular, the inhibition of photoaging of the skin.

Photoaging of the skin occurs through many mechanisms, including, for example, environmental factors such as tobacco smoke, exposure to the sun, and poor health, to name a few. These events can trigger an inflammatory process in the skin and the associated cellular mechanisms. There is also a more chronic low-level type of injury that does not produce a sunburn reaction, but which produces the changes of chronic photoaging. Chronological aging of the skin and photoaging and other environmentally induced changes share many or in some cases, all of the same pathways as UV induced photoaging of the skin. These pathways involve up and/or down regulation of cell proliferation and also alterations in the level of expression of many different types of genes.

It was surprisingly discovered that this combination of regulation of cell proliferation and regulation of gene expression is responsible for photoaging of the skin and other cells and tissues. Thus, photoaging could be reversed or at least ameliorated by affecting these same processes. Accordingly, one embodiment of the invention is directed to identifying and correlating the phenotypic and genotypic expression characteristics of photoaging and other skin and cell-associated disorders. Once identified, correlated maps can be compiled and collected into a data base to allow for the rapid and efficient identification of similar disorders and conditions for the purpose of tailoring appropriate treatment. Further, once identified, treatment and appropriate intervention and prevention methods can be used to halt or even reverse the appearance and genotypic characteristics of photoaging. Thus, the invention is not directed to artificially hiding or covering up aspects associated with aging, but actually reversing the processes and mechanisms associated with aging-related phenomena.

A further embodiment of the invention is directed to applying these same mechanisms and tools to other cells such as stem cells (completely undifferentiated cells) and progenitor cells (partially differentiated cells). By altering the cell cycle, cell proliferation, and/or gene expression characteristics of these cells along defined parameters, it is possible to determine differentiation pathways and to create or recreate cells, tissues and other cell structures for disease therapy and prevention, and wound healing.

Methods to modulate cell proliferation and gene expression include exposure to electromagnetic radiation in an amount or dose that is sufficient to stimulate the desired effect (e.g. see U.S. Pat. Nos. 6,398,753, 5,837,224, and 6,130,254; and U.S. Patent Application Nos. 2002/0028185, 2001/0053347, 2003/0004556, 2003/0004499, and 2002/0123746, all of which are specifically and entirely incorporated by reference). For example, exposure of skin to the radiation of an LED can stimulate or inhibit the expression of various gene products. These same methods can be used to cause stimulation or inhibition of cell proliferation and cell cycle modulation in these cell populations. Further, photomodulation can be used in combination with certain oral agents (for systemic affects) or topical agents (for localized affects) (e.g. vitamin A, retin A, retinol), for a desired effect unachievable with either stimulant used individually.

The types of cells that can be affected include, but are not limited to skin cells (reversal of photoaging), nerve cells (disease prevention and treatment), stem cells (tissue reconstruction), cells of hair follicles (hair growth or inhibition), cells of the immune system including cells intimately involved with the process of inflammation (due to disease, infection, or congenital disorder), wound repair, and combinations thereof. Modulation can be achieved by exposing cells to electromagnetic radiation (e.g. photomodulation) such as, preferably, visible light, (e.g. purple, blue, green, yellow, orange, red), infrared radiation, ultraviolet light (UVA, UVB, UVA1, UVA2, or combinations thereof), or combinations of any. Preferred exposure strengths and exposure times are as set forth in the attachments hereto, but may include pulsed exposures, continuous and periodic exposures.

Modulation of Gene Expression

Ultraviolet light injury triggers reactive oxygen species and a series of cell signaling events called kinase cascades. One of the final common pathway in the up and down regulation of fibroblast activity is through AP-1 which up regulates and increases the production of various MMP's including MMP 1 (collagenase 1 or interstitial collagenase synthesis), MMP 9 (gelatinaises B) and MMP 3 (stromelysins 1). The production of these MMP enzymes results in the breakdown of collagen, elastin and ECM in the dermis of the skin. Simultaneously the actual production of collagen I and other structural proteins may be diminished or down regulated thus further accelerating the process.

The aging of living cells, tissues and organs may be related to free radical exposure and oxidative stress. To apply this model to aging skin, chronological aging results from a decrease in antioxidant defense mechanisms, while UV photoaging and other environmental stresses can be thought of as increasing oxidative stress. The net result of decreased antioxidant defense or increased oxidative stress is increase production of ROS or free radicals.

Modulation of Gene Activity

Increased ROS production in the skin stimulates cell signaling or signal transduction pathways, which produce altered gene activity. Damage to structural proteins (e.g. damage, disruption and fragmentation of collagen caused by UV light) alters proteins, structure and function, which in turn changes cell signaling and may alter gene activity. Another possible outcome of increased ROS production is the production of DNA mutations, which then alter gene structure and thus may alter the normal structure and function of cells. Much of the variation in the human state, as far as disease and response to environmental insults, may be mediated by relatively small differences in the genetic make-up from one individual to the next. Single nucleotide polymorphisms (SNPs) are currently being very actively investigated as a means of identifying and potentially predicting the differences in biological responses of humans and other animals. For example, characterization of SNPs may allow prediction of whether a patient is more or less likely to develop a specific disease or tumor and thus take known preventative measures. Another possible application is the use of SNPs to screen individuals before placing them on a prescription drug to identify those individuals who might be more likely to develop serious side effects and thus avoid the use of that drug. Another potential novel use of SNPs is to identify the haplotype or patterns of SNPs, which are associate with, for example, chronological aging of the skin. Some individuals and families have reduced risk of skin cancers or simply look younger than their peers of the same age group and like backgrounds. A profile of SNPs can be developed that characterizes common factors associated with the phenotypic changes of aging skin (e.g., define the SNP genotypic pattern that puts an individual at a greater risk of accelerated aging from increased oxidative stress from environmental agents). This allows for a treatment plan, which would have greater anti-aging benefits.

TGF-B is a major cytokine for cell signaling and inhibits the growth of epidermal keratinocytes and stimulates the growth of thermal fibroblasts. It also induces synthesis and secretion of the major collagen elastin and inhibits the expression of MMP 1 and MMP 3. There are multiple TGF-B's, TGF-B1, TBR I, TBR II, many of which are down regulated in aging skin cells. TGF-B is also activity altered in aging skin by binding with Decerin and, when this combines with collagen, affects the tinsel strength of skin as well as controlling the rate of collagen fiber formation. c-Jeun MRNA is doubled in activity in aging human skin compared to young skin. But c-fos is unchanged. MMP 2 is not regulated through AP 1. ERK activity is reduced in aging skin, but JNK activity is increased 3-4 times in aging skin. Environmental insults-damage can vary anatomically over a person's body. These methods allow for rejuvenating human skin, including the steps of simultaneously preventing collagen degradation while also stimulating the formation of new collagen in aging human skin.

Increased MMP's result in reduced levels of ERK, cyclin D2 and type I and III pro collagen. This is part of the core genotype, phenotype stimulating a number of keratinocytes as well as decreasing c-gen activity and increasing ERK activity.

A system of sunscreens, topical oil and antioxidants, topical oil and photomodulated ECM stimulation and MMP and MMP inhibition and various combinations and mixtures of the above may be used. Inhibiting c-gen formation also inhibits formation of AP-1 and thus diminishes MMP's, inducing the proliferation of keratinocytes and fibroblasts.

Modulation of Mitochondrial Activity

Mitochondria and ATP production mechanisms (e.g. cytochrome expression) can be modulated by electromagnetic radiation. LED light activates cell surface receptors via redox mediated in activation or a receptor type protein tyrosine phosphatase (RTPT). SAP (stress activated pathways) verses MAP (mitogen activated pathways) compare and contrast, where SAP increases MMP and decreases pro collagen 1 and 2 if c-gen goes up, which primarily has to do with the ECM production. Whereas, the MAP pathways activate IRK induced cyclins and promote cell growth so that PSAT's tend to increase or decrease protein production and the MAPS increase or decrease cell growth. The Ras/MAP/AP-1 pathway plays a key role in response to wounding. FGFR1 contains sites in the promoter region and the IL1 antagonist promoter. Antioxidant compounds also have an anti-erythema sunscreen effect. Although they may not inhibit the increased MMP after UV exposure, lycopene is one of these antioxidant compounds. LED photomodulation can also be used to diminish sunburn activity and MMP levels are at maximum about 24 hours later. A solar simulator may be used to cause a one-MAD minimal erythema dose on the arm in two places on volunteers and then treat the arm a couple times a day with a GentleWaves® (GW1 device. The solar simulator may also be used to reduce redness with the chromometer. A biopsy will show what happens when the volunteers are treated with the GW device after UV. Inhibiting cytocrome P-450 breakdown of retinoids increases retinoid strength concentration.

While not wishing to be constrained to a particular theory of operation, the invention includes the surprising discovery that multiple receptor-mediated pathways may be photomodulated in human or mammalian skin that lead to an expression of the genotype associated with a younger or more youthful or less aged skin both in appearance and structurally and functionally.

Reference is made to infrared-a radiation induced MMP 1. Infrared is capable of producing MMP 1 by way of up regulation or activation of a MAPK signaling pathway, that is, the activation of ERK 1/2 where the promoter region of the MMP 1 gene is activated by IRA without the production of heat, but where TIMP 1 is not increased. MMP-8 or elastinase is increased with inflammatory reaction, which also involves AP 1. And when NF-KB is increased, it activates more of IL-1 and TNFa that discontinues the presence of continued inflammation.

A denser matrix surrounds fibroblasts. When in contact with a matrix, the fibroblasts tend to be less active and produce little collagen. But when the presence of collagen breaks down products such as gelatin, the fibroblasts tend to produce more collagen if the inflammation persists. The collagen not only proliferates, but produces, less scarring.

Topical compounds that inhibit cytokines are indirect MMP inhibitors because if they block the pathway they block the signals for expression or production of MMP. The same is true for MMP regulation. Regarding nutraceuticals, Vitamin C can be topically applied to assemble stable collagen molecules. Collagen I and collagen III can be stimulated by topical application of Vitamin C, whereas elastin, Fibrilin 1/2, and MMP 1, 2, and 9 are not affected, TIMP is increased, and TIMP 2 is unchanged.

Modulation for Wound Healing and Therapy

Proteolytic degradation of ECM is an essential feature of repair and remodeling during continuous wound healing. Wound repair consists of narcotic or damaged tissue, cell and/or tissue migration, angiogenisis, remodeling of newly synthesized ECM, and cell growth factor regulations. During wound repair, MMP 1 and MMP 3 increase as well as MMP 2 and 9. MMP 13, in particular, increases for chronic wounds, and also for acute wounds. TIMP is also altered. MMP 1, 3, 9 are increased with UVB. Increased elastin and fibrilian verscian result in the formation of non functional elastin fibers and reduction in skin elasticity and aging or photoaged skin. Collagen I is reduced, and UVA shows increased expression of MMP 1, 2, 3.

Disease states-systemic sclaraderma skin fibroblasts produce less MMP 1 and MMP 3 and more TIMP 1 compared to normal. Skin cancers BCC produce more MMP 1, 2, 9 and 11. More signs of photoaging, bruising, skin hypopigmented areas, and fibrosis are seen. Methods and inventions for preventing the photoaging or chronological or environmental aging of unaged skin include retinoids that retard the effects of photoaging topical antioxidants to reduce presence of ROS in the skin. Environmental stresses include oxidants, heat, UV light. Thus, LED phototherapy is both an ECM protein/collagen stimulator, and an MMP inhibitor. Dose dependent UVB induction of AP 1 and NF-KB can induce MMP 2 and MMP 9. The formation of collagen bundles is responsible for the strength, resiliency and elasticity of the skin.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

What is claimed is:

1. A method of dermatological treatment comprising exposing human tissue to electromagnetic radiation having an energy fluence to modulate cell activity of the genotype that when expressed produces a phenotype of aging skin, wherein the bandwidth of the electromagnetic radiation is greater than +/− about 10 nm about a dominant emissive wavelength, and wherein the energy fluence of the electromagnetic radiation inhibits the production of a gene expression pattern that produces aging-related indications changes and/or stimulates the production and activity of a gene expression pattern that retards aging or produces youthful characteristics.

2. The method of claim 1 wherein exposing involves exposure of said skin to electromagnetic radiation having a wavelength of from about 400 nm to about 1600 nm.

3. The method of claim 1 wherein the electromagnetic radiation is emitted by an LED.

4. The method of claim 1 comprising the step of filtering the electromagnetic radiation to reduce wavelengths in the infra red portion of the spectrum.

5. The method of claim 1 further comprising the step of administering to the human tissue a topical agent selected from one or more of Retinoic acid, vitamin A, vitamin C, Vitamin E, retin A, retinol, and mixtures thereof.

6. The method of claim 1 wherein the bandwidth of the electromagnetic radiation is no greater than +/− about 100 nm about a dominant emissive wavelength.

7. The method of claim 1 further comprising exposing human tissue to electromagnetic radiation from two or more sources of electromagnetic radiation.

* * * * *